(12) United States Patent
Gordon et al.

(10) Patent No.: US 7,361,656 B2
(45) Date of Patent: Apr. 22, 2008

(54) PRENYL TRANSFERASE INHIBITORS

(75) Inventors: Thomas D. Gordon, Medway, MA (US); Barry A. Morgan, Franklin, MA (US)

(73) Assignee: Societe de Conseils de Recherches et d'Applications Scientifiques, S.A.S., Paris (FR)

( * ) Notice: Subject to any disclaimer, the term of this patent is extended or adjusted under 35 U.S.C. 154(b) by 0 days.

(21) Appl. No.: 11/353,518

(22) Filed: Feb. 14, 2006

(65) Prior Publication Data

US 2006/0142275 A1 Jun. 29, 2006

Related U.S. Application Data

(63) Continuation of application No. 09/868,356, filed as application No. PCT/US99/31302 on Dec. 30, 1999, now Pat. No. 7,084,135, which is a continuation-in-part of application No. 09/224,428, filed on Dec. 31, 1998, now abandoned.

(60) Provisional application No. 60/114,301, filed on Dec. 31, 1998.

(51) Int. Cl.
*A61P 35/00* (2006.01)
*A61K 31/495* (2006.01)
*A61K 31/50* (2006.01)
*C07D 487/02* (2006.01)

(52) U.S. Cl. ...................... 514/249; 544/350

(58) Field of Classification Search ................ 514/249; 544/350
See application file for complete search history.

(56) References Cited

U.S. PATENT DOCUMENTS

| | | | | |
|---|---|---|---|---|
| 5,488,109 A | | 1/1996 | Olmstead et al. | 544/263 |
| 6,544,995 B1 * | | 4/2003 | Prevost et al. | 514/249 |
| 6,673,927 B2 * | | 1/2004 | Gordon et al. | 544/350 |
| 6,699,871 B2 * | | 3/2004 | Edmondson et al. | 514/249 |

FOREIGN PATENT DOCUMENTS

| HU | 216 967 | 10/1999 |
|---|---|---|
| WO | WO 97 30053 A | 8/1997 |
| WO | WO 00 02881 A | 1/2000 |

* cited by examiner

*Primary Examiner*—Brenda L Coleman
(74) *Attorney, Agent, or Firm*—Fish & Richardson; Alan F. Feeney; Tony K. Uhm

(57) ABSTRACT

A family of imidazole compounds useful for inhibiting the activity of prenyl transferases. The compounds are covered by the following formula:

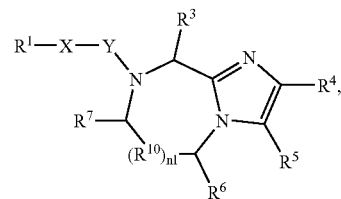

wherein X is $(CHR^{11})_{n3}(CH_2)_{n4}Z(CH_2)_{n5}$ where Z is O, $N(R^{12})$, S, or a bond; Y is CO, $CH_2$, CS, or a bond; $R^1$ is

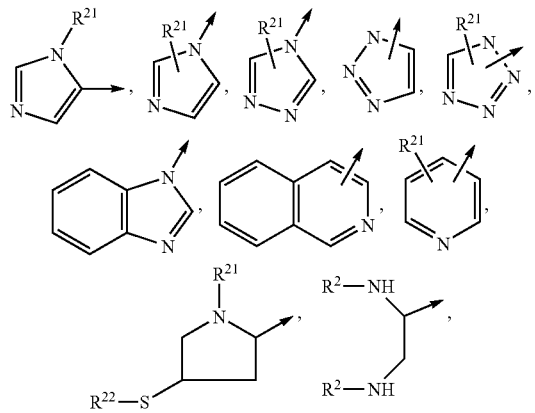

or $N(R^{24}R^{25})$; and the remaining substituents are as defined in the disclosure.

8 Claims, No Drawings

PRENYL TRANSFERASE INHIBITORS

CROSS-REFERENCE TO RELATED APPLICATIONS

This application is a continuation of U.S. application Ser. No. 09/868,356, filed Aug. 10, 2001, now U.S. Pat. No. 7,084,135, which is the national phase application under 35 U.S.C. § 371 of International Application PCT/US99/31302, with a filing date of Dec. 30, 1999, which is a continuation-in-part of U.S. patent application Ser. No. 09/224,428, with a filing date of Dec. 31, 1998, now abandoned, and claims benefit of U.S. Provisional Application No. 60/114,301 filed Dec. 31, 1998.

BACKGROUND OF THE INVENTION

The Ras family of proteins are important in the signal transduction pathway modulating cell growth. The protein is produced in the ribosome, released into the cytosol, and post-translationally modified. The first Step in the series of post-translational modifications is the alkylation of $Cys^{168}$ with farnesyl or geranylgeranyl pyrophosphate in a reaction catalyzed by prenyl transferase enzymes such as farnesyl transferase and geranylgeranyl transferase (Hancock, J F, et al., Cell 57:1167-1177 (1989)). Subsequently, the three C-terminal amino acids are cleaved (Gutierrez, L., et al., EMBO J. 8:1093-1098 (1989)), and the terminal Cys is converted to a methyl ester (Clark, S., et al., Proc. Nat'l Acad. Sci. (USA) 85:4643-4647 (1988)). Some forms of Ras are also reversibly palmitoylated on cysteine residues immediately N-terminal to $Cys^{168}$ Buss, J E, et al., Mol. Cell. Biol. 6:116-122 (1986)). It is believed that these modifications increase the hydrophobicity of the C-terminal region of Ras, causing it to localize at the surface of the cell membrane. Localization of Ras to the cell membrane is necessary for signal transduction (Willumsen, B M, et al., Science 310: 583-586 (1984)).

Oncogenic forms of Ras are observed in a relatively large number of cancers including over 50 percent of colon cancers and over 90 percent of pancreatic cancers (Bos, J L, Cancer Research 49:4682-4689 (1989)). These observations suggest that intervention in the function of Ras mediated signal transduction may be useful in the treatment of cancer.

Previously, it has been shown that the C-terminal tetrapeptide of Ras has the "CAAX" motif (wherein C is cysteine, A is an aliphatic amino acid, and X is any amino acid). Tetrapeptides having this structure have been shown to be inhibitors of prenyl transferases (Reiss, et al., Cell 62:81-88 (1990)). Poor potency of these early farnesyl transferase inhibitors has prompted the search for new inhibitors with more favorable pharmacokinetic behavior (James, G L, et al., Science 260:1937-1942 (1993); Kohl, N E, et al., Proc. Nat'l Acad. Sci. USA 91:9141-9145 (1994); deSolms, S J, et al., J. Med. Chem. 38:3967-3971 (1995); Nagasu, T, et al., Cancer Research 55:5310-5314 (1995); Lerner, E C, et al., J. Biol. Chem. 270:26802-26806 (1995); Lerner, E C, et al., J. Biol. Chem. 270:26770 (1995); and James, et al., Proc. Natl. Acad. Sci. USA 93:4454 (1996)).

Recently, it has been shown that a prenyl transferase inhibitor can block growth of Ras-dependent tumors in nude mice (Kohl, N E, et al., Proc. Nat'l Acad. Sci. USA 91:9141-9145 (1994)). In addition, it has been shown that over 70 percent of a large sampling of tumor cell lines are inhibited by prenyl transferase inhibitors with selectivity over non-transformed epithelial cells (Sepp-Lorenzino, I, et al., Cancer Research, 55:5302-5309 (1995)). Inhibiting farnesylation has been disclosed as a method of treating hepatitis delta virus infection, (Casey, P, et al., WO 97/31641).

SUMMARY OF THE INVENTION

In one aspect, the invention features a compound of formula (I):

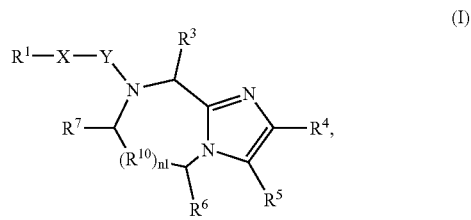

wherein
n1 is 0 or 1;
X is, independently for each occurrence, $(CHR^{11})_{n3}(CH_2)_{n4}Z(CH_2)_{n5}$;
Z is O, $N(R^{12})$, S, or a bond;
n3 is, independently for each occurrence, 0 or 1;
n4 and n5 each is, independently for each occurrence, 0, 1, 2, or 3;
Y is, independently for each occurrence, CO, $CH_2$, CS, or a bond;
$R^1$ is

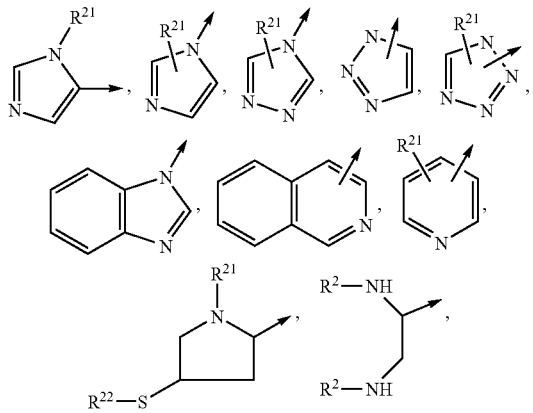

or $N(R^{24}R^{25})$;
$R^2$, $R^{11}$, and $R^{12}$ each is, independently for each occurrence, H or an optionally substituted moiety selected from the group consisting of $(C_{1-6})$alkyl and aryl, wherein said optionally substituted moiety is optionally substituted with one or more of $R^8$ or $R^{30}$;
$R^3$ is, independently for each occurrence, H or an optionally substituted moiety selected from the group consisting of $(C_{1-6})$alkyl, $(C_{2-6})$alkenyl, $(C_{2-6})$alkynyl, $(C_{3-6})$cycloalkyl, $(C_{3-6})$cycloalkyl$(C_{1-6})$alkyl, $(C_{5-7})$cycloalkenyl, $(C_{5-7})$cycloalkenyl$(C_{1-6})$alkyl, aryl, aryl$(C_{1-6})$alkyl, heterocyclyl, and heterocyclyl$(C_{1-6})$alkyl, wherein said optionally substituted moiety is optionally substituted with one or more $R^{30}$;
$R^4$ and $R^5$ each is, independently for each occurrence, H or an optionally substituted moiety selected from the group consisting of $(C_{1-6})$alkyl, $(C_{3-6})$cycloalkyl, aryl, and heterocyclyl, wherein said optionally substituted moiety is optionally substituted with one or more $R^{30}$, wherein each said substituent is independently selected, or $R^4$ and $R^5$ can be taken together with the carbons to which they are attached to form aryl;

$R^6$ is, independently for each occurrence, H or an optionally substituted moiety selected from the group consisting of $(C_{1-6})$alkyl, $(C_{2-6})$alkenyl, $(C_{3-6})$cycloalkyl, $(C_{3-6})$cycloalkyl$(C_{1-6})$alkyl, $(C_{5-7})$cycloalkenyl, $(C_{5-7})$cycloalkenyl$(C_{1-6})$alkyl, aryl, aryl$(C_{1-6})$alkyl, heterocyclyl, and heterocyclyl$(C_{1-6})$alkyl, wherein said optionally substituted moiety is optionally substituted with one or more substituents each independently selected from the group consisting of OH, $(C_{1-6})$alkyl, $(C_{1-6})$alkoxy, —N($R^8R^9$), —COOH, —CON($R^8R^9$), and halo, where $R^8$ and $R^9$ each is, independently for each occurrence, H, $(C_{1-6})$alkyl, $(C_{2-6})$alkenyl, $(C_{2-6})$alkynyl, aryl, or aryl$(C_{1-6})$alkyl;

$R^7$ is, independently for each occurrence, H, =O, =S, or an optionally substituted moiety selected from the group consisting of $(C_{1-6})$alkyl, $(C_{2-6})$alkenyl, $(C_{3-6})$cycloalkyl, $(C_{3-6})$cycloalkyl$(C_{1-6})$alkyl, $(C_{5-7})$cycloalkenyl, $(C_{5-7})$cycloalkenyl$(C_{1-6})$alkyl, aryl, aryl$(C_{1-6})$alkyl, heterocyclyl, and heterocyclyl$(C_{1-6})$alkyl, wherein said optionally substituted moiety is optionally substituted with one or more substituents each independently selected from the group consisting of OH, $(C_{1-6})$alkyl, $(C_{1-6})$alkoxy, —N($R^8R^9$), —COOH, —CON($R^8R^9$), and halo;

$R^{10}$ is C;

or when n1=0, $R^6$ and $R^7$ can be taken together with the carbon atoms to which they are attached to form aryl or cyclohexyl;

$R^{21}$ is, independently for each occurrence, H or an optionally substituted moiety selected from the group consisting of $(C_{1-6})$alkyl and aryl$(C_{1-6})$alkyl, wherein said optionally substituted moiety is optionally substituted with one or more substituents each independently selected from the group consisting of $R^8$ and $R^{30}$;

$R^{22}$ is H, $(C_{1-6})$alkylthio, $(C_{3-6})$cycloalkylthio, $R^8$—CO—, or a substituent according to the formula

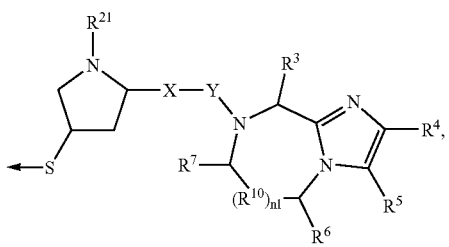

$R^{24}$ and $R^{25}$ each is, independently for each occurrence, H, $(C_{1-6})$alkyl, or aryl$(C_{1-6})$alkyl;

$R^{30}$ is, independently for each occurrence, $(C_{1-6})$alkyl, —O—$R^8$, —S(O)$_{n6}R^8$, —S(O)$_{n7}$N($R^8R^9$), —N($R^8R^9$), —CN, —NO$_2$, —CO$_2R^8$, —CON($R^8R^9$), —NCO—$R^8$, or halogen;

n6 and n7 each is, independently for each occurrence, 0, 1, or 2;

wherein said heterocyclyl is azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, or thienyl; and wherein said aryl is phenyl or naphthyl;

provided that:

when n1=1, $R^{10}$ is C and $R^6$ is H, then $R^{10}$ and $R^7$ can be taken together to form

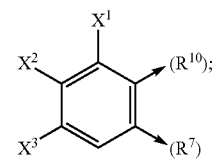

or when n1=1, $R^{10}$ is C, and $R^7$ is =O, —H, or =S, then $R^{10}$ and $R^6$ can be taken together to form

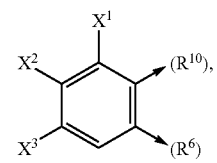

wherein $X^1$, $X^2$, and $X^3$ each is, independently, H, halogen, —NO$_2$, —NCO—$R^8$, —CO$_2R^8$, —CN, or —CON($R^8R^9$); and when $R^1$ is N($R^{24}R^{25}$), then n3 is 1, n4 and n5 each is 0, Z is a bond, and $R^3$ and $R^{11}$ can be taken together to form

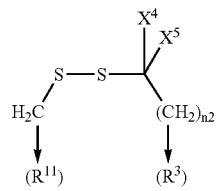

wherein n2 is 1-6, and $X^4$ and $X^5$ each is, independently, H, $(C_{1-6})$alkyl, or aryl, or $X^4$ and $X^5$ can be taken together to form $(C_{3-6})$cycloalkyl;

or a pharmaceutically acceptable salt thereof.

A preferred group of compounds of formula (I), designated group A, is where:

$R^1$ is

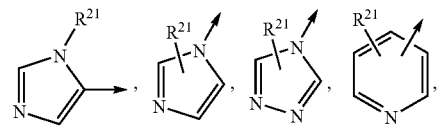

-continued

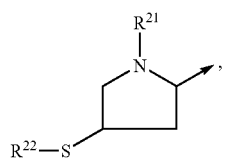

or

N(R²⁴R²⁵); and

X is CH(R¹¹)$_{n3}$(CH$_2$)$_{n4}$ or Z, wherein Z is O, S, or N(R¹²);

or a pharmaceutically acceptable salt thereof.

Another preferred group of compounds of formula (I), designated group B, is where:

R¹ is

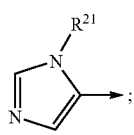

X is CH(R¹¹)$_{n3}$(CH$_2$)$_{n4}$; and
n1 is 0;

or a pharmaceutically acceptable salt thereof.

Another preferred group of compounds of formula (I), designated group C, is where:

R¹ is

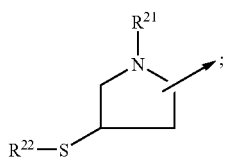

n3, n4, and n5 each is 0;
Z is a bond;
Y is, independently for each occurrence, CO or CS; and
n1 is 0;

or a pharmaceutically acceptable salt thereof.

Another preferred group of compounds of formula (I), designated group D, is where:

R¹ is

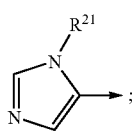

R⁶ is H;
n1 is 1;

R⁷ and R¹⁰ are taken together to form

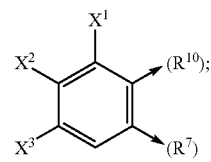

n3 is 1 and R¹¹ is H;
Z is O or a bond;
n5 is 0; and
Y is CO, CH$_2$, or a bond;

or a pharmaceutically acceptable salt thereof.

Another preferred group of compounds of formula (I), designated group E, is where:

R¹ is N(R²⁴R²⁵);
n1 is 0;
n3 is 1;
n4 is 0;
n5 is 0;
Y is CO or CS;
Z is a bond; and
R³ and R¹¹ are taken together to form

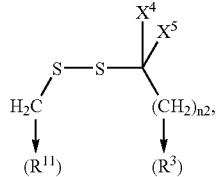

or a pharmaceutically acceptable salt thereof.

Another preferred group of compounds of formula (I), designated group F, is where:

R¹ is

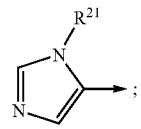

R⁷ is H or =O;
n1 is 1;
R⁶ and R¹⁰ are taken together to form

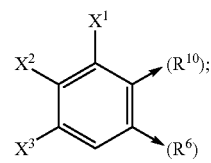

n3 is 1 and R¹¹ is H;
n5 is 0;
Y is CO or CH$_2$; and
Z is O or a bond;

or a pharmaceutically acceptable salt thereof.

In another aspect, the present invention is directed to a pharmaceutical composition comprising one or more of a compound of formula (I), as defined hereinabove, or a pharmaceutically acceptable salt thereof, and a pharmaceutically acceptable carrier.

In yet another aspect, the present invention is directed to a method of inhibiting prenyl transferases (e.g., farnesyl transferase or geranylgeranyl transferase) in a subject, e.g., a mammal such as a human, by administering to the subject a therapeutically effective amount of a compound of formula I, as defined hereinabove, or a pharmaceutically acceptable salt thereof. In a further aspect, the present invention is directed to a method of treating restenosis or tissue proliferative diseases (e.g., tumor) in a subject by administering to the subject a therapeutically effective amount of a compound of formula (I) or a pharmaceutically acceptable salt thereof. Examples of a tissue proliferative disease include both those associated with benign (e.g., non-malignant) cell proliferation such as fibrosis, benign prostatic hyperplasia, atherosclerosis, and restenosis, and those associated with malignant cell proliferation, such as cancer (e.g., ras-mutant tumors). Examples of treatable tumors include but are not limited to breast, colon, pancreas, prostate, lung, ovarian, epidermal, and hematopoietic cancers (Sepp-Lorenzino, I, et al., Cancer Research 55:5302 (1995)).

In a still further aspect, the present invention is directed to the use of one or more-compounds of formula (I), as defined hereinabove, or a pharmaceutically acceptable salt thereof, to bind to a prenyl transferase, as when performing an in vitro or in vivo assay.

DETAILED DESCRIPTION OF THE INVENTION

In general, the compounds of formula (I) can be made by processes which include those known in the chemical arts for the production of compounds. Certain processes for the manufacture of formula (I) compounds are provided as further features of the invention and are illustrated by the reaction schemes and examples included herein.

In the above structural formulas and throughout the instant application, the following terms have the indicated meanings unless expressly stated otherwise:

The term alkyl is intended to include those alkyl groups having the designated number of carbon atoms in either a straight or branched configuration. Exemplary of such alkyl groups are methyl, ethyl, propyl, isopropyl, butyl, sec-butyl, tertiary butyl, pentyl, isopentyl, hexyl, isohexyl and the like. When the term $C_0$-alkyl is included in a definition it is intended to denote a single covalent bond.

The term cycloalkyl is intended to include a mono-cycloalkyl group or a bi-cycloalkyl group having the designated number of carbon atoms. Exemplary of such cycloalkyl groups are cyclopropyl, cyclobutyl, cyclohexyl, and the like.

The term alkenyl is intended to include hydrocarbon groups having one or more double bonds and the designated number of carbon atoms in either a straight or branched configuration. Exemplary of such alkenyl groups are ethenyl. propenyl, isopropenyl, butenyl, sec-butenyl, tertiary butenyl, pentenyl, isopentenyl, hexenyl, isohexenyl and the like.

The term cycloalkenyl is intended to include a mono-cycloalkenyl group or a bi-cycloalkenyl group of the indicated carbon number having one or more double bonds, but not enough double bonds so as to make the group aromatic. Exemplary of such cycloalkenyl groups are cyclopentenyl, cyclohexenyl, cycloheptenyl, and the like.

The term alkynyl is intended to include those alkynyl groups, i.e.; hydrocarbon groups having one or more triple bonds, having the designated number of carbon atoms in either a straight or branched configuration. Exemplary of such alkynyl groups are ethynyl, propynyl, butynyl, pentynyl, isopentynyl, hexynyl, isohexynyl and the like.

The term alkylthio is intended to include those alkylthio groups, i.e., hydrocarbon groups which are bonded to the molecule through a sulfur atom, having the designated number of carbon atoms in either a straight or branched configuration. Exemplary of such alkyl groups are methylthio, ethylthio, propylthio, isopropylthio, butylthio, sec-butylthio, tertiary butylthio, pentylthio, isopentylthio, hexylthio, isohexylthio and the like.

The term cycloalkylthio is intended to include a mono-cycloalkylthio group or a bi-cycloalkylthio group of the indicated carbon number. Exemplary of such cycloalkylthio groups are cyclopentylthio, cyclohexylthio, and the like.

The term alkoxy is intended to include those alkoxy groups having the designated number of carbon atoms in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term aryl is intended to include aromatic rings known in the art, which can be mono-cyclic or bi-cyclic, such as phenyl and naphthyl.

The term heterocyclyl, as used herein, represents a 5- to 7-membered monocyclic or 8- to 11-membered bicyclic or 11-15 membered tricyclic heterocyclic ring which is either saturated or unsaturated, and which consists of carbon atoms and from one to four heteroatoms independently selected from the group consisting of N, O, and S. Also included are any bicyclic group in which any of the above-defined heterocyclic rings is fused to a benzene ring, wherein the heterocyclic ring can be attached at any heteroatom or carbon atom. Examples of such heterocyclic moieties include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, thienyl, and the like.

The chemist of ordinary skill will recognize that certain combinations of heteroatom-containing substituents listed in this invention define compounds which will be less stable under physiological conditions. Accordingly, such compounds are less preferred.

The term halogen or halo is intended to include the halogen atoms fluorine, chlorine, bromine and iodine.

When a chemical structure as used herein has an arrow emanating from it, the arrow indicates the point of attachment. For example, the structure

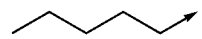

is a pentyl group. When a value in parentheses appears near the arrow, the value indicates where in the compound the point of attachment may be found. For example, in general formula (I):

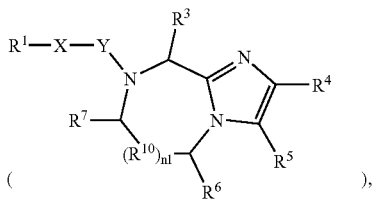

as hereinabove defined, when $R^{10}$ and $R^7$ are taken together to form

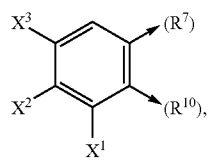

the following structure results:

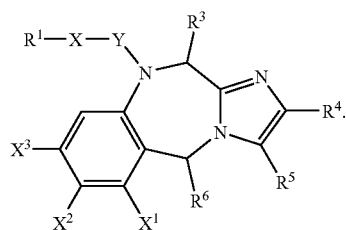

Similarly in general formula (I), as hereinabove defined, when $R^3$ and $R^{11}$ are taken together to form

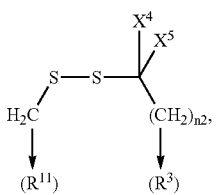

the following structure results:

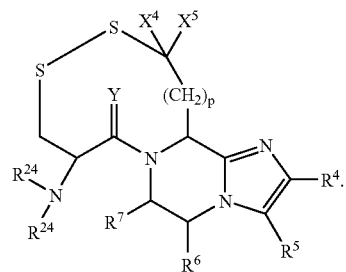

When a line is drawn through a cyclic moiety, the line indicates that the substituent can be attached to the cyclic moiety at any of the available bonding points. For example,

means that the substituent "X" can be bonded. ortho, meta or para to the point of attachment. Further, when a line is drawn through a bi-cyclic or a tri-cyclic moiety, the line indicates that the substituent can be attached to the bi-cyclic or a tri-cyclic moiety at any of the available bonding points in any of the rings. Similarly, when an arrow is drawn through a cyclic moiety, the arrow indicates that the point of attachment of the cyclic moiety to the compound can occur at any of the available bonding points on the cyclic moiety. Further, when an arrow is drawn through a bi-cyclic or a tri-cyclic moiety, the arrow indicates that the point of attachment of the bi-cyclic or a tri-cyclic moiety to the compound can occur at any of the available bonding points in any of the rings of the bi-cyclic or a tri-cyclic moiety.

Some of the compounds of the instant invention can have at least one asymmetric center. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, are included within the scope of the instant invention.

The compounds of the instant invention generally can be isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts can be formed by taking about 1 equivalent of a compound of formula (I) and contacting it with about 1 equivalent or more of the appropriate corresponding acid of the salt which is desired. Work-up and isolation of the resulting salt is well-known to those of ordinary skill in the art.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration. Accordingly, the present invention includes within its scope pharmaceutical compositions comprising, as an active ingredient, at least one of the compounds of formula (I) in association with a pharmaceutically acceptable carrier.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

In general, an effective dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment, all of which are within the realm of knowledge of one of ordinary skill in the art. Generally, dosage levels of between 0.0001 to 100 mg/kg of body weight daily are administered to humans and other animals, e.g., mammals.

A preferred dosage range is 0.01 to 10.0 mg/kg of body weight daily, which can be administered as a single dose or divided into multiple doses.

Compounds of the instant invention can be and were assessed for activity on anchorage-dependent growth of human tumor cell lines according to the following assay.

Cells were seeded in a 96 well plate at day 0 and treated at day 1 for 96 hours with the following concentrations of a compound of the present invention: 50, 25, 12.5, 6.25, 3.12, 1.56, 0.78, 0.39 and 0.00 µM. At the end of this period, the quantification of cell proliferation is evaluated by colorimetric assay based on the cleavage of the tetrazolium salt WST1 by mitochondrial dehydrogenases in viable cells leading to the formazan formation. These experiments were twice repeated in octuplicates, thus allowing for the determination of a window of compound concentration including the $IC_{50}$ value.

The protocol described immediately above was performed using the following human tumor cell lines: Prostate: DU145 adenocarcinoma, with WT ras, resistant to L744-832; Colon: HT29, adenocarcinoma with Wild Type ras (WT), sensitive to L744-832; Pancreas: MIA PaCa-2, carcinoma with Ki-ras mutation; Lung: A427, carcinoma with Ki-ras mutation.

It is to be understood that while the invention has been described in conjunction with the detailed description thereof, that the foregoing description is intended to illustrate and not limit the scope of the invention, which is defined by the scope of the appended claims.

EXAMPLES

Compound 1: 8-Butyl-7-(3-(imidazol-5-yl)-1-oxo-propyl)-2-(2-methoxyphenyl)-5,6,7,8-tetrahydroimidazo[1,2a]pyrazine

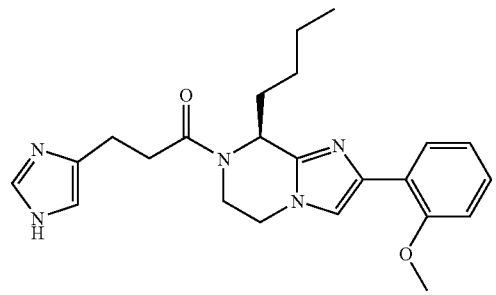

Compound 2: 8-butyl-2-(2-hydroxyphenyl)-7-(imidazol-4-yl-propyl)-5,6,7,8-tetrahydroimidazo[1,2a]pyrazine

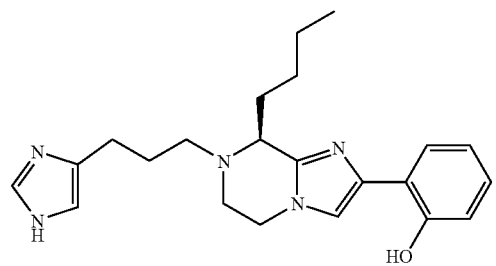

Compound 3: 8-butyl-7-(4-imidazolylpropyl)-2-(2-methoxyphenyl)-5,6,7,8-tetrahydro-imidazo-[1,2a]-pyrazine

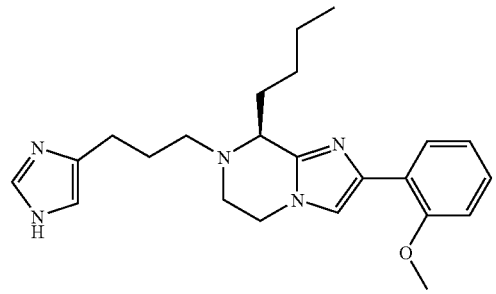

Compound 4: 7-(2-(imidazol-4-yl)-1-oxo-ethyl)-2-(2-methoxyphenyl)-8-(1-methylpropyl)-5,6,7,8-tetrahydroimidazo[1,2a]pyrazine Compound 8: 7-((1H-imidazol-4-yl)methyl)-2-(2-methoxyphenyl)-8-(1-methylpropyl)-5,6,7,8-tetrahydroimidazo[1,2a]pyrazine

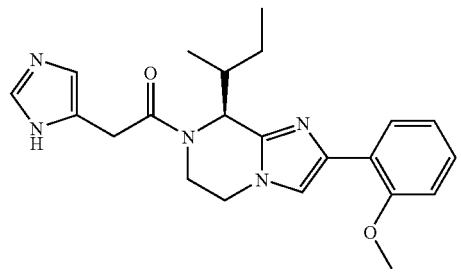

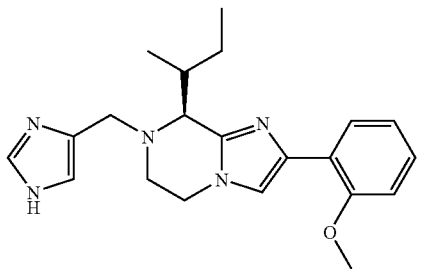

Compound 5: 2-(2-methoxyphenyl)-8-(1-methylpropyl)-7-(1-oxo-2-(1-(phenylmethyl)-imidazol-5-yl)ethyl)-5,6,7,8-tetrahydroimidazo[1,2a]pyrazine Compound 9: 7-((4-imidazolyl)carbonyl)-2-(2-methoxyphenyl)-8-(1-methylpropyl)-5,6,7,8-tetrahydroimidazo[1,2a]pyrazine

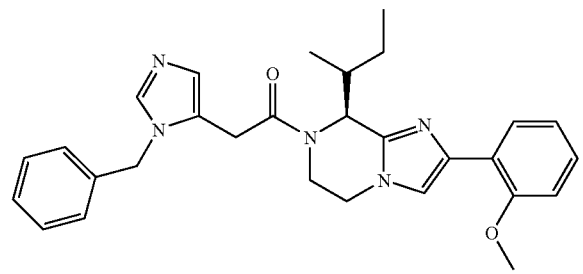

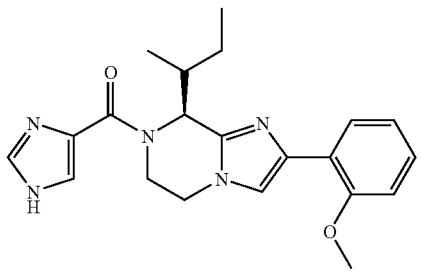

Compound 6: 2-(2-methoxyphenyl)-8-(1-methylpropyl)-7-(2-(1-phenylmethyl)-imidazol-5-yl)ethyl)-5,6,7,8-tetrahydroimidazo[1,2a]pyrazine Compound 10: 7-(1-(4-cyanophenylmethyl)-imidazol-5-yl)methyl-2-(2-methoxyphenyl)-8-(1-methylpropyl)-5,6,7,8-tetrahydroimidazo[1,2a]pyrazine

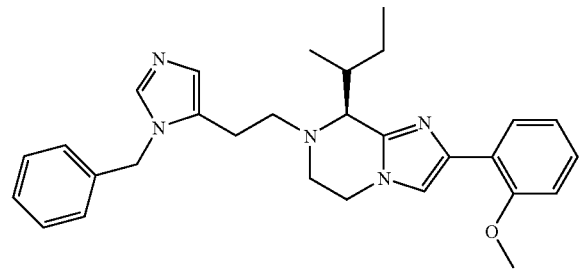

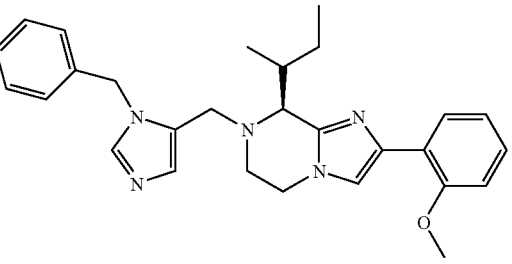

Compound 7: 7-(2-(1-(4-cyanophenylmethyl)-imidazol-5-yl)-1-oxo-ethyl)-2-(2-methoxyphenyl)-8-(1-methylpropyl)-5,6,7,8-tetrahydroimidazo[1,2a]pyrazine Compound 11: 5-(2-(1-(4-cyanophenylmethyl)-imidazol-5-yl)-1-oxo-ethyl)-5,6-dihydro-2-phenyl-1H-imidazo[1,2-a][1,4]benzodiazepine

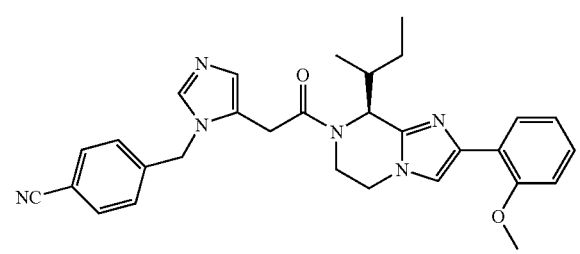

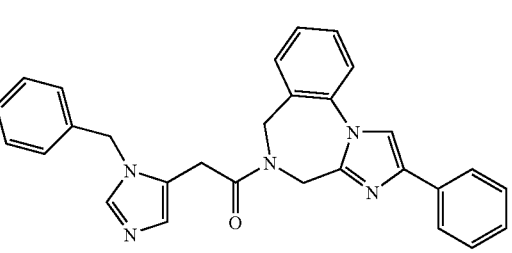

Compound 12: 7-(2-(4-cyanophenylmethyl)-imidazol-5-yl)-1-oxo-ethyl)-2-(2-methoxyphenyl)-5,6,7,8-tetrahydroimidazo[1,2-a]pyrazine

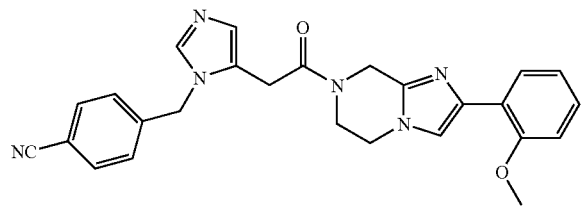

Compound 13: 7-(2-amino-1-oxo-3-thiopropyl)-8-(mercaptoethyl)-2-(2-methoxyphenyl)-5,6,7,8-tetrahydroimidazo[1,2a]pyrazine disulfide

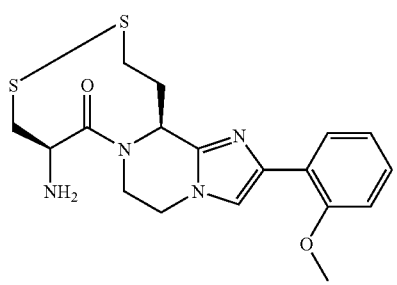

Compound 14: 5-butyl-7-(2-(4-cyanophenylmethyl imidazol-5-yl)-1-oxo-ethyl)-2-phenyl-5,6,7,8-tetrahydroimidazo[1,2-a]pyrazine

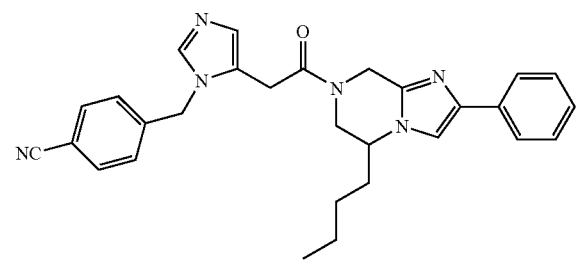

Compound 15: 6-butyl-7-(2-(4-cyanophenylmethylimidazol-5-yl)-1-oxo-ethyl)-2-(2-methoxyphenyl)-5,6,7,8-tetrahydroimidazo[1,2-a]pyrazine

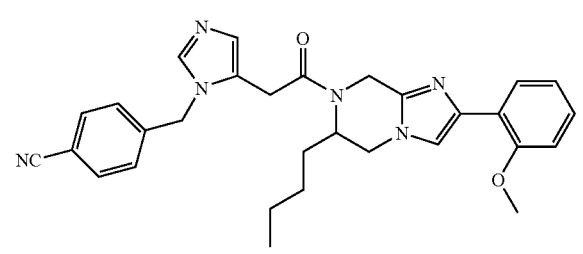

Compound 16: 6-butyl-7-(2-(4-cyanophenylmethyl imidazol-5-yl)-1-oxo-ethyl)-2-phenyl-5,6,7,8-tetrahydroimidazo[1,2-a]pyrazine

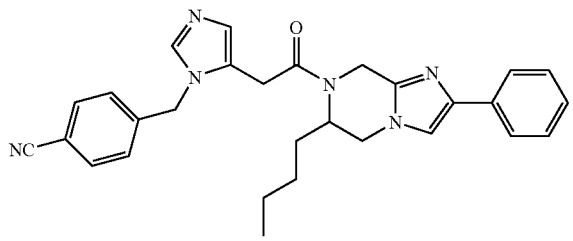

Compound 17: 5-butyl-7-(2-(1-(4-cyanophenylmethyl)-imidazole-5-yl)-1-oxo-ethyl)-2-(2-methoxyphenyl)-5,6,7,8-tetrahydroimidazo[1,2a]pyrazine

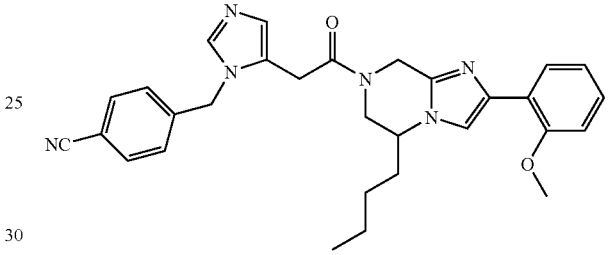

Compound 18: 7-(2-(1-(4-cyanophenylmethyl)-imidazole-5-yl)-1-oxo-ethyl)-8-(cyclohexylmethyl)-2-(2-methoxyphenyl)-5,6,7,8-tetrahydroimidazo[1,2a]pyrazine

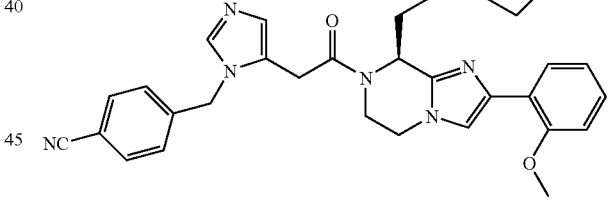

Compound 19: 5-butyl-7-(2-(1H-imidazole-5-yl)-1-oxo-ethyl)-2-(2-methoxyphenyl)-5,6,7,8-tetrahydroimidazo[1,2a]pyrazine

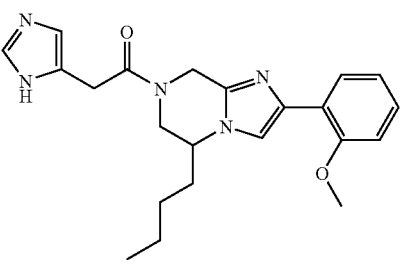

Compound 20: 7-(2-(4-cyanophenylmethyl)-imidazol-5-yl)-1-oxo-ethyl)-2-(2-(phenylmethoxy)-phenyl)-5,6,7,8-tetrahydroimidazo[1,2-a]pyrazine

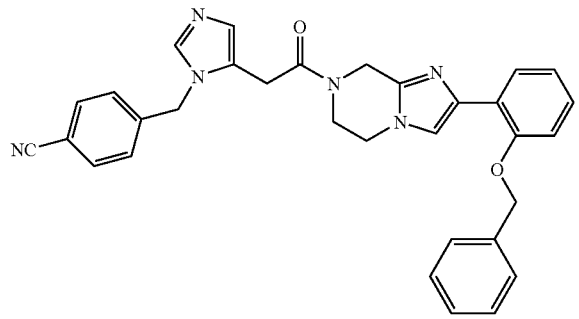

Compound 21: 2-(2-butoxyphenyl)-7-(2-(4-cyanophenylmethyl)-imidazol-5-yl)-1-oxo-ethyl)-5,6,7,8-tetrahydroimidazo[1,2-a]pyrazine

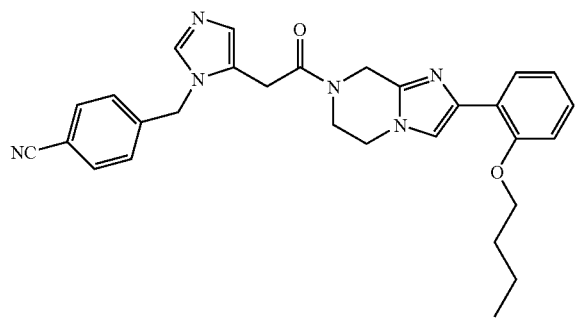

Compound 22: 1,2-dihydro-1-((1H-imidazol-4-yl)methyl)-4-(2-methoxyphenyl)-imidazo[1,2-c][1,4]benzodiazepine

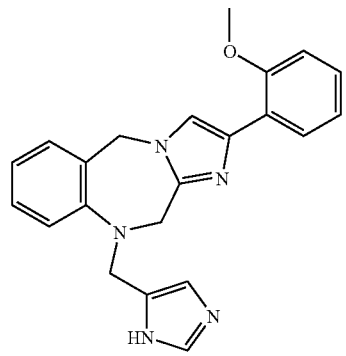

Compound 23: 1-(2-(1-(4-cyanophenylmethyl)imidazol-4-yl)-1-oxoethyl)-1,2-dihydro-4-(2-methoxyphenyl)-imidazo[1,2-c][1,4]benzodiazepine

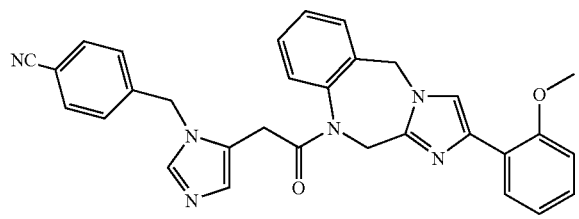

Compound 24: 9-bromo-1-(2-(1-(4-cyanophenylmethyl)imidazol-4-yl)-1-oxoethyl)-1,2-dihydro-4-(2-methoxyphenyl)-imidazo[1,2-c][1,4]benzodiazepine

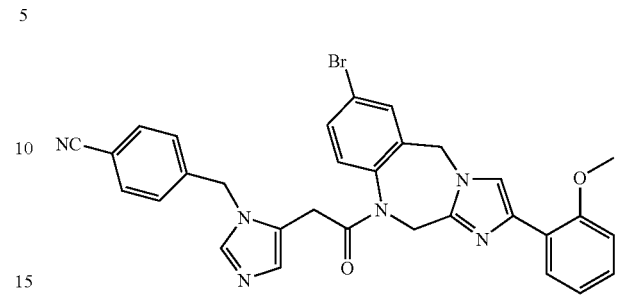

Compound 25: 9-Chloro-1-(2-(1-(4-cyanophenylmethyl)imidazol-4-yl)-1-oxoethyl)-1,2-dihydro-4-(2-methoxyphenyl)-imidazo[1,2-c][1,4]benzodiazepine

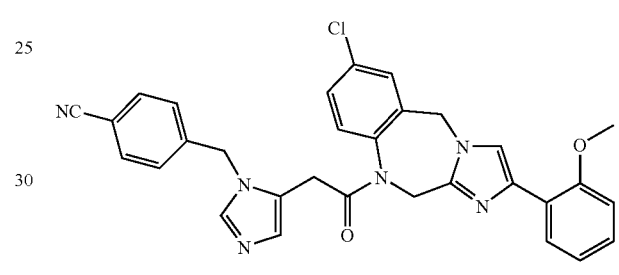

Compound 26: 10-Bromo-1-(2-(1-(4-cyanophenylmethyl)imidazol-4-yl)-1-oxoethyl)-1,2-dihydro-4-(2-methoxyphenyl)-imidazo[1,2-c][1,4]benzodiazepine

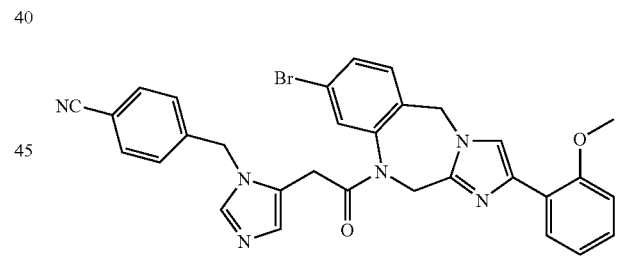

Compound 27: 1-(2-(1-(4-cyanophenylmethyl)imidazol-4-yl)-1-oxoethyl)-1,2-dihydro-8-fluoro-4-(2-methoxyphenyl)-imidazo[1,2-c][1,4]benzodiazepine

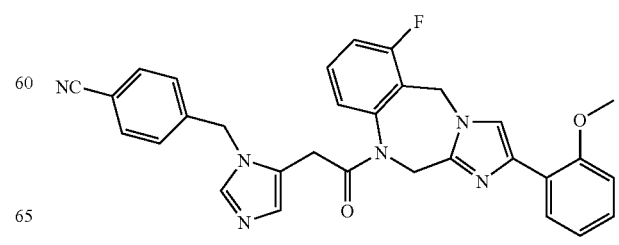

Compound 28: 1,2-dihydro-1-(2-(imidazol-1-yl)-1-oxoethyl)-4-(2-methoxyphenyl)imidazo[1,2a][1,4]benzodiazepine

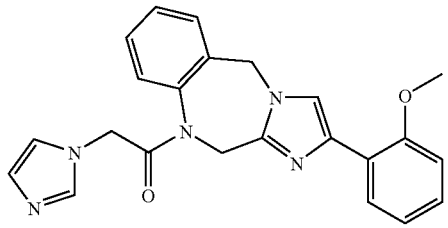

Compound 29: 1,2-dihydro-4-(2-methoxyphenyl)-1-(2-(pyridin-3-yl)-1-oxoethyl)imidazo[1,2a][1,4]benzodiazepine

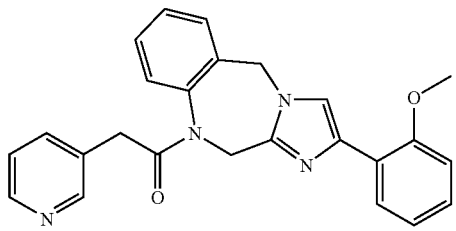

Compound 30: 1,2-dihydro-4-(2-methoxyphenyl)-1-(2-(pyridin-4-yl)-1-oxoethyl)imidazo[1,2a][1,4]benzodiazepine

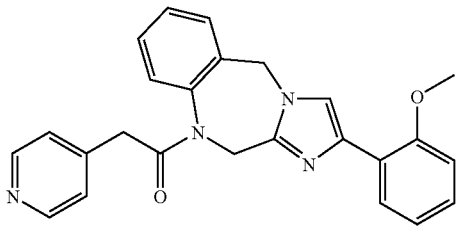

Compound 31: 1-(2-(1-benzylimidazol-5-yl)-1-oxoethyl)-1,2-dihydro-8-fluoro-4-(2-methoxyphenyl)imidazo[1,2a][1,4]benzodiazepine

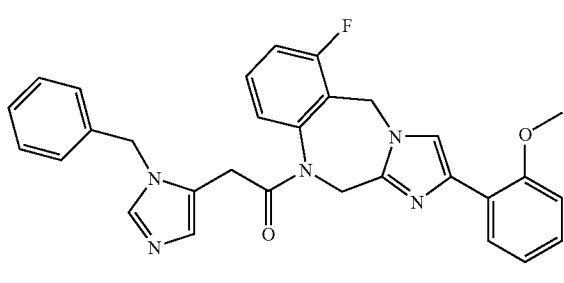

Compound 32: 1-(2-(1-((4-cyano)phenylmethyl)imidazol-5-yl)-1-oxoethyl-9,10-difluoro-1,2-dihydro-4-(2-methoxyphenyl)imidazo[1,2c][1,4]-benzodiazepine

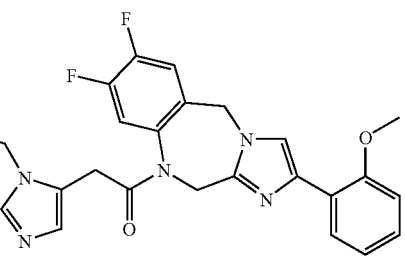

Compound 33: 4-(2-bromophenyl)-1-(2-(1-[(4-cyano)phenylmethyl]imidazol-5-yl)-1-oxoethyl)-1,2-dihydro-8-fluoro-imidazo[1,2a][1,4]-benzodiazepine

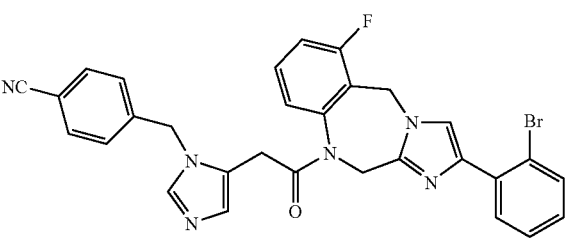

Compound 34: 1-(2-(1-((4-cyano)phenylmethyl)imidazo-5-yl)-1-oxoethyl)-1,2-dihydro-10-fluoro-4-(2-methoxyphenyl)imidazo[1,2a][1,4]-benzodiazepine

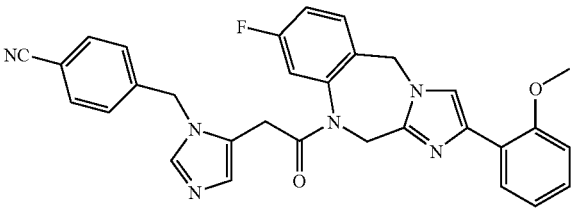

Compound 35: 1-(2-(1-((4-cyano-3-methoxy)phenylmethyl)imidazo-5-yl)-1-oxoethyl)-1,2-dihydro-8-fluoro-4-(2-methoxyphenyl)imidazol[1,2a][1,4]-benzodiazepine

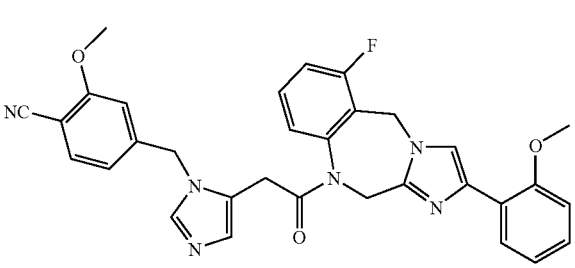

Compound 36: 10-Bromo-1-(2-(1-((4-cyano-3-methoxy)phenylmethyl)imidazo-5-yl)-1-oxoethyl)-1,2-dihydro-4-(2-methoxyphenyl)imidazol[1,2a][1,4]-benzodiazepine

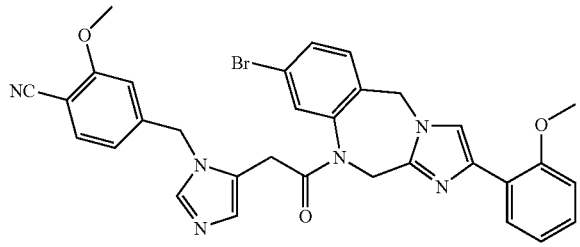

Compound 37: 1-(2-(1-((4-cyano-3-methoxy)phenylmethyl)imidazo-5-yl)-1-oxoethyl)-1,2-dihydro-8-fluoro-4-phenylimidazol[1,2a][1,4]-benzodiazepine

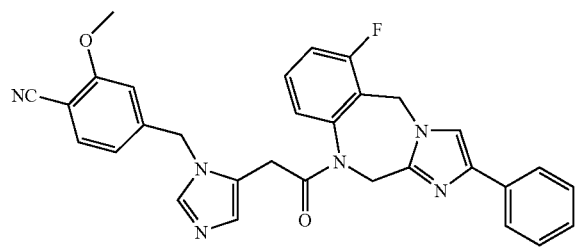

Compound 38: 4-(2-bromophenyl)-1-(2-(1-((4-cyano-3-methoxy)phenylmethyl)imidazo-5-yl)-1-oxoethyl)-1,2-dihydro-8-fluoroimidazol[1,2a][1,4]-benzodiazepine

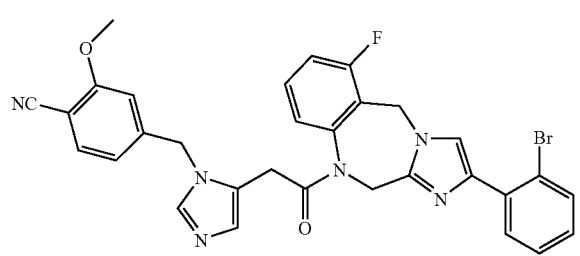

Compound 39: 1-(2-(1-((3-methoxy)phenylmethyl)imidazo-5-yl)-1-oxoethyl)-1,2-dihydro-8-fluoro-4-(2-methoxyphenyl)imidazol[1,2a][1,4]-benzodiazepine

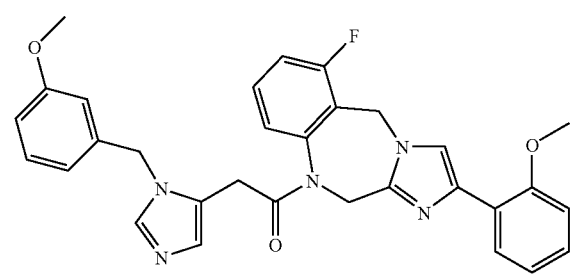

Compound 40: 1-(2-(5-((4-cyano)phenylmethyl)imidazol-1-yl)-1-oxoethyl-2,5-dihydro-8-fluoro-4-(2-methoxyphenyl)imidazo[1,2c][1,4]-benzodiazepine

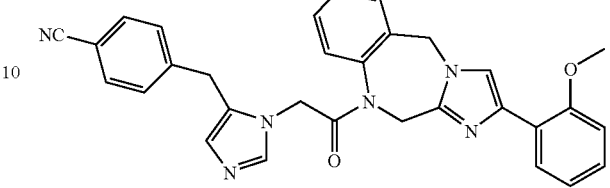

EXPERIMENTAL

In the following examples and schemes the substituent variables are used as defined therein. The substituent variables of the schemes and examples do not necessarily coincide with those defined in the claims.

Example 1

8-Butyl-7-(3-(imidazol-5-yl)-1-oxopropyl)-2-(2-methoxyphenyl)-5,6,7,8-tetrahydro imidazo[1,2a] pyrazine Example 1 was synthesized according to Scheme 1 as set forth below.

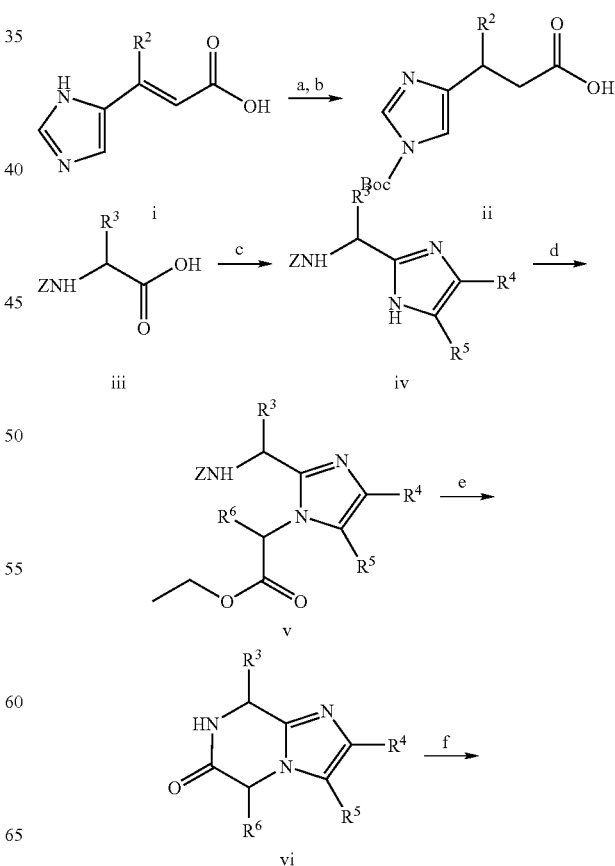

-continued

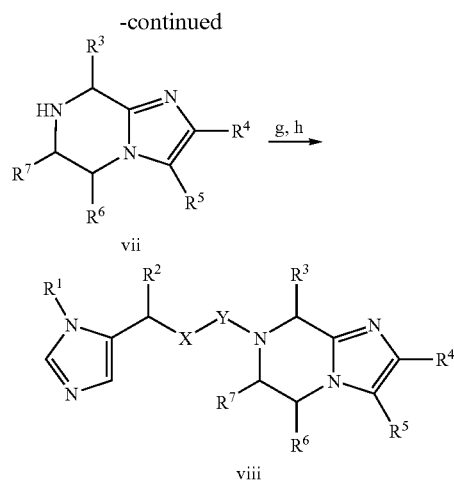

vii viii 1.a. H₂/Pd on carbon/HOAc,
1.b. (BOC)₂O/K₂CO₃/5% aq. HCl/MeOH
1.c. Cs₂CO₃, Br—CHR⁵CO R⁴, then NH₄OAc/xylenes
1.d. Br—CHR⁶CO₂Et/K₂CO₃/DMF
1.e. H₂/Pd on carbon/HOAc
1.f. BH₃/THF
1.g. Compound ii/DCC/HOAt/DMF
1.h. Tfa/iPr₃SiH

Step 1.a. 3-(1H-Imidazol-5-yl)-propionic acid

Urocanic acid (compound i, where R² is H)(1.38 g, 10.0 mmol) was dissolved in 5% aqueous HCl (20 ml) plus MeOH (15 ml) containing 10% Pd on carbon (100 mg) and the mixture was shaken overnight under about 30 psi H₂. The catalyst was removed by filtration through a 3 cm pad of diatomaceous earth and the filtrate was concentrated to a solid and dried overnight under vacuum. The crude material was used without further purification. Mass spec. 141.4 MH+

Step 1.b. 3-(1-((1,1-Dimethylethoxy)carbonyl)-imidazol-5-yl)-propionic acid

The crude product from Step 1.a. (10.0 mmol) was dissolved in H₂O (10 ml) containing K₂CO₃ (2.76 g, 20 mmol) and to that was added di-tert-butyl dicarbonate (2.18 g, 10.0 mmol) in acetonitrile (20 ml). The reaction was stirred vigorously for about 3 hours, then H₂O (10 ml) was added and the mixture was concentrated to about V₂ volume. The mixture was acidified with citric acid and extracted with EtOAc (2×25 ml). The aqueous extracts were dried over Na₂SO₄, filtered and concentrated to solids which were dried under reduced pressure to yield 1.89 g (79%). NMR (300 MHz, DMSO-d₆, 30° C.) 12.0-12.2 (1H, s), 8.0-8.2 (1H, s), 7.2-7.3 (1H, s), 2.65-2.8 (2H, t), 2.45-2.65 (2H, t), 1.5-1.7 (9H, s).

Step 1.c. 2-(1-(S)-(((Phenylmethoxy)carbonyl)-amino)-pentyl)-4-((2-methoxyphenyl)-imidazole Cbz-(L)-Norleucine (compound iii, where R³ is n-butyl) (10.6 g, 40.0 mmol) and Cs₂CO₃ (6.52 g, 20.0 mmol) were combined in 2:1/DMF:H₂O (65 ml) and the mixture was swirled until homogeneous. Solvents were removed under reduced pressure, the residue was dissolved in DMF (75 ml) and 2-bromo-2'-methoxyacetophenone (9.16 g, 40.0 mmol) in DMF (50 ml) was added. The mixture was stirred about 15 minutes at room temperature then concentrated under reduced pressure. The resulting keto-ester was dissolved in xylenes (250 ml), filtered, NH₄OAc (50.0 g, 0.36 mol) was added and the mixture was heated at reflux for about 3 hours with removal of excess NH₄OAc and liberated H₂O using a Dean-Stark trap. The reaction mixture was concentrated under reduced pressure. Saturated NaHCO₃ solution (100 ml) was added and the product was extracted with CH₂Cl₂ (3×50 ml). The combined CH₂Cl₂ layers were dried over Na₂SO₄, filtered and concentrated under vacuum to yield a first crop of 6.23 g (m.r.=118-121° C.) of the title compound. The mother liquors were purified by flash chromatography on silica gel using 2:3/EtOAc:hexanes as eluant. Pure product fractions were combined and concentrated to yield a second crop of 3.26 g (m.r.=119-122° C.) for a combined yield of 9.49 g (60%) of the title compound. NMR (300 MHz, DMSO-d₆, 30° C.) 11.7-11.9 (1H,s), 8.0-8.15 (1H, d), 7.5-7.7 (1H, m), 7.4-7.5 (1H, s), 7.1-7.4 (6H, m), 6.9-7.1 (2H, m), 4.95-5.2 (2H, q), 4.6-4.8 (1H, q), 3.8-4.0 (3H, s), 1.6-2.0 (2H, m), 1.1-1.4 (4H, m), 0.8-1.0 (3H, t).

Step 1.d. 1-(2-Ethoxy-2-oxoethyl)-2-(1-(S)-(((Phenylmethoxy)carbonyl)-amino)-pentyl)-4-(2-methoxyphenyl)-imidazole The product from Step 1.c. (compound iv, where R³ is n-butyl, R⁴ is 2-methoxyphenyl, and R⁵ is H) (9.40 g, 23.9 mmol) was dissolved in DMF (50 ml) and treated with K₂CO₃ (6.90 g, 50.0 mmol) and ethyl bromoacetate (4.17 ml, 75.0 mmol), and the mixture was heated at about 55° C. for about 2 hours. The mixture was concentrated then dissolved in ether (100 ml) and washed once with saturated NaHCO₃ solution (50 ml) and once with saturated NaCl solution (50 ml). The ether layer was dried over Na₂SO₄, filtered and concentrated to an oil (11.5 g, 100%) which was used without further purification. Mass spec. 480.3 MH+, NMR (300 MHz, DMSO-d₆, 30° C.) 8.04-8.12 (1H, d,d), 7.65-7.85 (1H, t broad), 7.5-7.6 (1H, s), 7.25-7.4 (5H, m), 7.1-7.25 (1H, m), 7.0-7.1 (1H, d), 6.9-7.05 (1H, t), 4.9-5.15 (2H, q), 5.0-5.2 (2H, s), 4.5-4.7 (1H, q), 4.05-4.2 (2H, q), 3.8-4.0 (3H, s), 1.8-2.0 (2H, m), 1.2-1.4 (4H, m), 1.15-1.25 (3H, t), 0.75-0.95 (3H, t).

Step 1.e. 8-Butyl-6-oxo-2-(2-methoxyphenyl)-imidazo[1,2-a]pyrazine

The product from Step 1.d. (compound v where R³ is n-butyl, R⁴ is 2-methoxyphenyl, and R5 and R6 are H) (11.5 g, 23.9 mmol) was dissolved in HOAc (100 ml) containing 10% Pd on carbon catalyst (500 mg) and hydrogenated under 50 psi of H₂ for about 3 hours at room temperature. The catalyst was removed by filtration through a 3 cm pad of diatomaceous earth and the filtrate was warmed at about 70° C. for about 2 hours. The mixture was concentrated to a solid under reduced pressure, dissolved in CH₂Cl₂ (100 ml) and washed with saturated NaHCO₃ solution (125 ml). The CH₂Cl₂ layer was dried over Na₂SO₄, filtered and 275 ml hexanes was added. Product was filtered off and dried to constant weight to yield 6.21 g (87%) of product, m.r.=200-202° C., NMR (300 MHz, DMSO-d₆, 30° C.) 8.5-8.6 (1H s), 8.0-8.1 (1H, d), 7.4-7.6 (1H, s), 7.1-7.3 (1H, t), 7.0-7.1 (1H, d), 6.9-7.1 (1H, t), 4.55-4.8 (2H, q), 4.55-4.7 (1H, t), 3.8-4.0 (3H, s), 1.75-1.95 (2H, m), 1.1-1.5 (4H, m), 0.8-0.9 (3H, t).

Step 1.f. 8-Butyl-2-(2-methoxyphenyl)-5,6,7,8-tetrahydro-imidazo[1,2-a]pyrazine The product from Step 1.e. (6.13 g, 20.5 mmol) (compound vi where R³ is n-butyl, R⁴ is 2-methoxyphenyl, and R⁵ and R6 are H) was dissolved in THF (100 ml) and treated with 1M BH₃/THF (82.0 ml, 82.0 mmol) at room temperature for about 2 hours and then refluxed for about 3 hours. The mixture was cooled to room temperature and 4N HCl (50 ml) was added dropwise. The mixture was stirred at room temperature for about 2 hours then made basic by careful portionwise addition of solid K$_2$CO$_3$. Product was extracted with EtOAc (3×50 ml). The EtOAc layers were combined, dried over Na$_2$SO$_4$, filtered and concentrated under reduced pressure. The residue was dissolved in MeOH (about 50 ml), concentrated HCl (1.75 ml) was added and the solution was again concentrated under reduced pressure. The product was crystallized from MeOH/Et$_2$O to yield 6.76 g (92%) of the desired product. Mass spec. 286.3 MH$^+$, NMR (300 MHz, DMSO-d$_6$, 30° C.) 10.0-11.5 (2H, s broad), 8.05-8.15 (1H, d,d), 8.0-8.1 (1H, s), 7.35-7.5 (1H, t), 7.15-7.3 (1H, d), 7.0-7.15 (1H, t), 4.8-4.95 (1H, m), 4.4-4.65 (2H, m), 3.9-4.0 (3H, s), 3.65-3.8 (1H, m), 3.5-3.65 (1H, m), 2.45-2.65 (1H, m), 2.1-2.35 (1H, m), 1.5-1.7 (2H, m), 1.25-1.5 (2H, m), 0.85-1.0 (3H, t).

Step 1.g. 8-Butyl-7-(3-(((1,1-dimethylethoxy)carbonyl)-imidazol-5-yl)-1-oxopropyl)-2-(2-methoxyphenyl)-5,6,7,8-tetrahydro-imidazo[1,2-a]pyrazine DCC (309 mg, 1.50 mmol) and the product from Step 1.b. (compound ii, where R$^2$ is H) (720 mg, 3.00 mmol) was dissolved in THF (10 ml) and stirred about 30 minutes at room temperature. The solids were filtered off, the product from Step 1.f (compound vii where R$^3$ is n-butyl, R$^4$ is 2-methoxyphenyl, and R$^5$, R$^6$ and R$^7$ are H) (358 mg, 1.0 mmol) was added, and the mixture stirred at room temperature overnight. The mixture was concentrated to a gum and purified by flash chromatography on silica gel using EtOAc as eluant. Product fractions were combined, concentrated to a glass, and dried to a constant weight. Yield=500 mg, (99%). Mass spec. 508.2 (MH$^+$).

Step 1.h. 8-Butyl-7-(3-(imidazol-5-yl)-1-oxopropyl)-2-(2-methoxyphenyl)-5,6,7,8-tetrahydroimidazo[1,2-a]pyrazine The product from Step 1.g. (450 mg, 0.89 mmol) was dissolved in MeOH (5 ml) and 4$\underline{N}$ HCl was added and the reaction was stirred at room temperature for about ½ hour. Solvents were removed under reduced pressure to yield 420 mg of crude product. Part of the crude (100 mg) was purified by preparative HPLC on a RAININ™ C$_{18}$ column (Varian Analytical, Walnut Creek, Calif.) using a gradient of 10-30% CH$_3$CN/aq. HCl (pH=2.0) over 45 minutes with UV detection at 254 nm. Product fractions were concentrated to about ½ volume and lyophilized to yield pure product (47 mg, 47%) as the di-hydrochloride. Mass spec. 508.2 MH$^-$.

Example 2

8-Butyl-2-(2-hydroxyphenyl)-7-(imidazol-4-yl-propyl)-5,6,7,8-tetrahydroimidazo[1,2a]pyrazine The product of Step 1.h. (compound viii, where R$^1$, R$^2$, R$^5$, R$^6$, and R$^7$ are H, R$^3$ is n-butyl, R$^4$ is 2-methoxyphenyl, X is —CH$_2$— and Y is —CO—) (320 mg, 0.667 mmol), was dissolved in a minimum of THF and a 1$\underline{M}$ solution of BH$_3$ in THF (10.0 ml, 10.0 mmol) was added dropwise with stirring. The mixture was heated at reflux for about 2 hours then cooled. A 4$\underline{N}$ HCl solution was added dropwise and the mixture was heated briefly to reflux and then made basic by careful portionwise addition of solid K$_2$CO$_3$. Product was extracted with EtOAc (3×10 ml) and then extracted again with 0.5% aqueous Tfa (4×10 ml). The crude product was purified by preparative HPLC on a RAININ™ C$_{18}$ column using a gradient of 0-25% CH$_3$CN/0.1% aqueous Tfa over 45 minutes with UV detection at 254 nm. Product fractions were concentrated to about ½ volume and lyophilized and then relyophilized twice from dilute HCL to yield pure product (41 mg, 13%) as the di-hydrochloride. Mass spec. 380.3 MH$^+$. NMR (300 MHz, DMSO-d$_6$, 30° C.) 9.0-9.1 (1H, s), 7.9-8.05 (2H, m), 7.45-7.55 (1H, s), 7.2-7.3 (1H, t), 7.05-7.15 (1H, d), 6.9-7.0 (1H, t), 4.5-6.0 (3-4H, s broad), 4.0-4.4 ( ), 1.5-1.7 (2H, m), 1.25-1.5 (2H, m), 0.8-1.0 (3H, t).

Example 3

8-Butyl-7-(4-imidazolylpropyl)-2-(2-methoxyphenyl)-5,6,7,8-tetrahydro-imidazo[1,2a]pyrazine The product of Step 1.h. (475 mg, 0.937 mmol), was dissolved in MeOH (10 ml) and a solution of NaOH (80 mg, 2.0 mmol) in H$_2$O (1 ml) was added at room temperature and the mixture was stirred for about ½ hour and then concentrated under reduced pressure. The residue was dissolved in THF (10 ml), dried over Na$_2$SO$_4$, filtered and concentrated under reduced pressure to about 2 ml and 1$\underline{M}$ BH$_3$/THF (8.0 ml) was added. The mixture was heated at reflux for about 3 hours and the quenched by addition of 5% aqueous HCl with brief warming at reflux. The reaction was cooled to room temperature, made basic by careful addition of solid NaHCO$_3$, and extracted with CH$_2$Cl$_2$ (2×10 ml). The CH$_2$Cl$_2$ layers were dried over Na$_2$SO$_4$, filtered and concentrated under reduced pressure. The residue was purified by preparative HPLC on a RAININ™ C$_{18}$ column using a gradient of 0-25% CH$_3$CN/aq. HCl (pH=2.0) over 45 minutes with UV detection at 270 nm. Product fractions were concentrated to about ½ volume and lyophilized to yield pure product (64 mg, 15%) as the di-hydrochloride. Mass spec. 394.3 MH$^+$, NMR (300 MHz, DMSO-d$_6$, 30° C.) 9.0-9.1 (1H, s), 8.0-8.2 (2H, d), 7.9-8.1 (1H, s), 7.4-7.5 (1H, s), 7.35-7.5 (1H, t), 7.1-7.3 (1H, d), 7.0-7.2 (1H, t), 5.0-7.0 (3H, s broad), 4.1-4.5 (3H, m), 3.9-4.0 (3H, s), 3.2-3.7 (2H, d broad), 2.7-3.0 (2H, s broad), 2.6-2.9 (2H, t), 1.9-2.2 (4H, m), 1.0-1.7 (4H, m), 0.8-1.0 (3H, t), Example 4

7-(2-(Imidazol-4-yl)-1-oxo-ethyl)-2-(2-methoxyphenyl)-8-(1-methylpropyl)-5,6,7,8-tetrahydroimidazo[1,2a]pyrazine Example 4 was synthesized according to Schemes 1 and 4, with Steps 1.a. and 1.b. being replaced by Steps 4.a. through 4.c.

Scheme 4

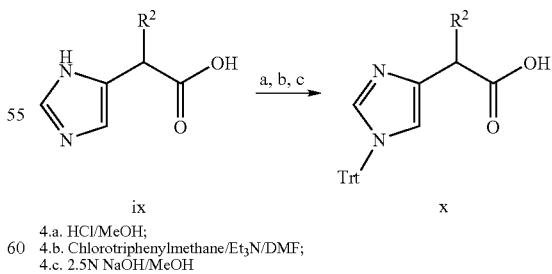

4.a. HCl/MeOH;
4.b. Chlorotriphenylmethane/Et$_3$N/DMF;
4.c. 2.5N NaOH/MeOH

Step 4.a. Methyl 4-Imidazoleacetate

A solution of 4-Imidazoleacetic acid, sodium salt, hydrate (compound ix, where R$^2$ is H) (3.0 g, 18.1 mmol) in MeOH (50 ml) was cooled to about 0° C. and anhydrous HCl gas was bubbled into the mixture for about 15 minutes while maintaining reaction temperature below about 5° C. The reaction was stirred for about 12 hour at room temperature and then solvents were removed under reduced pressure to yield an oil which solidifies on standing. Mass spec 141.0 MH$^+$, NMR (300 MHZ, DMSO-d$_6$, 30° C.), 9.0-9.2 (1H, s), 7.47.6 (1H, s), 3.85-3.95 (2H, 3), 3.6-3.7 (3H, s).

Step 4.b. Methyl 1-triphenylmethyl-4-imidazoleacetate

A solution of the product from Step 4.a. (3.2 g, 17.5 mmol) in DMF (50 ml) was treated with chlorotriphenylmethane (4.88 g, 17.5 mmol) and Et$_3$N (5.4 ml, 38.5 mmol) and the reaction was stirred at room temperature for about 6 hours. The DMF was evaporated under reduced pressure and the residue was distributed between EtOAc and saturated NaCl solution. The EtOAc layer was dried over Na$_2$SO$_4$, filtered and concentrated under reduced pressure to yield product as a viscous oil (6.96 g, 104%) which crystallized on standing. Mass spec. 383.3 MH$^+$.

Step 4.c. 1-Triphenylmethyl-4-imidazoleacetic acid, sodium salt

The product from Step 4.b. (2.0 g, 5.24 mmol) was dissolved in MeOH (20 ml) and 2.5N NaOH (2.1 ml) was added at room temperature and the mixture was stirred overnight. Solvents were removed under reduced pressure to yield crude product (2.08 g, 102%) which was used in subsequent steps without further purification.

Steps 4.d. through 4.i. were carried out in a manner analogous to Steps 1.c. through 1.h. of example 1, starting with Cbz-(L)-Ile-OH in place of Cbz-(L)-Nle-OH, and yielding (2-(2-methoxyphenyl)-8-(1-methylpropyl)-5,6,7,8-tetrahydro-(7-(2-(1-triphenylmethyl-imidazol-4-yl)-1-oxo-ethyl)-imidazo[1,2a]pyrazine) (compound viii, where R$^1$, R$^2$, R$^5$, R$^6$, and R$^7$ are H, R$^3$ is isobutyl, and R$^4$ is 2-methoxyphenyl).

Step 4.j. 7-(2-(1H-Imidazol-4-yl)-1-oxo-ethyl)-2-(2-methoxyphenyl)-8-(1-methylpropyl)-5,6,7,8-tetrahydroimidazo[1,2a]pyrazine The product of Step 4.i. (150 mg, 0.24 mmol) was treated with Tfa (1.0 ml) containing iPr$_3$SiH (51 uL, 0.25 mmol) at room temperature for about 2 hours. Ether (10 ml) was added and the product was extracted with 3×10 ml of 0.1% aqueous Tfa solution. The crude product was purified by preparative HPLC on a RAININ™ C$_{18}$ column using a gradient from 20% to 70% CH$_3$CN/0.1% Tfa over 45 minutes Product fractions were combined, concentrated and re-lyophilized from dilute HCl to yield product (53 mg, 57%) as the dihydrochloride. Mass spec. 394.3 MH$^+$.

Example 5

2-(2-Methoxyphenyl)-8-(1-methylpropyl)-7-(1-oxo-2-(1-(phenylmethyl)-imidazol-5-yl)ethyl)-5,6,7,8-tetrahydroimidazo[1,2a]pyrazine Example 5 was synthesized according to Schemes 1 and 5, with Steps 1.a. and 1.b. being replaced by Steps 5.a. through 5.c.

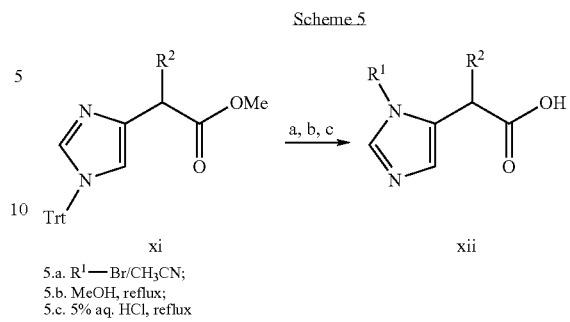

Scheme 5

5.a. R$^1$ — Br/CH$_3$CN;
5.b. MeOH, reflux;
5.c. 5% aq. HCl, reflux

Step 5.a. Methyl 1-phenylmethyl-3-triphenylmethyl-5-imidazoleacetate

Methyl 1-triphenylmethyl-4-imidazoleacetate from Step 4.b. (1.12 g, 2.93 mmol) was dissolved in CH$_3$CN (15 ml) and Benzyl bromide (349 ul, 2.93 mmol) was added at room temperature. The mixture was refluxed for about 3 hours and allowed to stand at room temperature overnight. The solvents were removed under reduced pressure and the residue was used without further purification in Step 5.b.

Step 5.b. Methyl 1-phenylmethyl-5-imidazoleacetate

The product from Step 5.a. was dissolved in MeOH (20 ml) and the mixture was heated at reflux for about 1 hour. Solvents were removed under reduced pressure. The residue was triturated with hexanes (2×20 ml) and with EtOAc (2×20 ml). The residue was used without further purification in Step 5.c.

Step 5.c. 1-Phenylmethyl-5-imidazoleacetic acid

The product from Step 5.b. was dissolved in 5% aqueous HCl and heated at reflux for about 3 hours and then concentrated under reduced pressure. The crude product was purified by preparative HPLC on a RAININ™ C$_{18}$ column using a gradient from 5% to 35% CH$_3$CN/0.1% Tfa over 45 minutes. Product fractions were combined, concentrated and re-lyophilized from dilute HCl to yield product (360 mg, 49%) as the hydrochloride. Mass spec. 217.1 MH$^+$, NMR (300 MHZ, DMSO-d$_6$, 30° C.), 8.4-8.6 (1H, s), 7.3-7.5 (3H, m), 7.1-7.3 (3H, m), 5.2-5.4 (2H, s), 3.5-3.7 (2H, s).

Steps 5.d. through 5.g. were carried out in a manner analogous to Steps 1.c. through 1.f of example 1, starting with Cbz-(L)-Ile-OH in place of Cbz-(L)-Nle-OH, and yielding 2-(2-methoxyphenyl)-8-(1-methylethyl)-5,6,7,8-tetrahydro-imidazo[1,2-a]pyrazine (compound vii, where R$^3$ is isobutyl, R$^4$ is 2-methoxyphenyl and R$^5$, R$^6$, and R$^7$ are H,).

Step 5.h. 2-(2-Methoxyphenyl)-8-(1-methylpropyl)-7-(1-oxo-2-(1-(phenylmethyl)-imidazol-5-yl)ethyl)-5,6,7,8-tetrahydroimidazo[1,2a]pyrazine DCC (206 mg, 1.00 mmol), HOSu (115 mg, 1.00 mmol), NMM (220 uL, 2.0 mmol), the product from Step 5.g. (179 mg, 0.50 mmol) and the product from Step 5.c. (330 mg, 1.00 mmol) were dissolved in DMF (10 ml) and stirred at room temperature overnight and then warmed at about 50° C. for about 8 hours. The mixture was concentrated to a gum and purify by preparative HPLC on a RAININ™ C$_{18}$ column using a gradient from 25% to 40% CH$_3$CN/0.1% aqueous Tfa over 30 minutes Product fractions were combined, concentrated and re-lyophilized from dilute HCl to yield product (96 mg, 40%) as the hydrochloride.

Mass spec. 484.3 MH+.

Example 6

2-(2-Methoxyphenyl)-8-(1-methylpropyl)-7-(2-(1-phenylmethyl)-imidazol-5-yl)ethyl)-5,6,7,8-tetrahydroimidazo[1,2a]pyrazine Example 6 was prepared from the product of Step 5.h. in a manner analogous to Example 3. Mass spec. 470.4 MH+, NMR (300 MHZ, DMSO-$d_6$, 30° C.) 9.15-9.4 (1H, s), 8.05-8.2 (1H, d,d), 7.9-8.1 (1H, d), 7.5-7.6 (1H, s), 7.25-7.5 (6H, m), 7.15-7.25 (1H, d,d), 7.05-7.15 (1H, m), 5.5-5.6 (2H, s), 4.6-5.4 (3H, s broad), 4.0-4.3 (2H, m), 3.8-4.0 (4H, m), 3.1-3.5 (2H, m), 2.6-9.95 (4H, m), 1.95-2.15 (1H, m), 1.3-1.5 (1H, m), 1.1-1.3 (1H, m), 0.85-1.0 (3H, d), 0.7-0.85 (3H, t).

Example 7

7-(2-(1-(4-Cyanophenylmethyl)-imidazol-5-yl)-1-oxo-ethyl)-2-(2-methoxyphenyl)-8-(1-methylpropyl)-5,6,7,8-tetrahydroimidazo[1,2a]pyrazine (2-(2-methoxyphenyl)-8-(1-methylpropyl)-5,6,7,8-tetrahydro-(7-(2-(1-triphenylmethyl-imidazol-4-yl)-1-oxo-ethyl)-imidazo[1,2a]pyrazine) (compound viii, where $R^1$, $R^2$, $R^5$, $R^6$, and $R^7$ are H, $R^3$ is isobutyl, and $R^4$ is 2-methoxyphenyl) from Example 4, Step 4.i. (135 mg, 0.21 mmol) was dissolved in $CH_3CN$ (3.0 ml) and α-bromo-p-tolunitrile (42 mg, 0.21 mmol) was added and the mixture was heated at reflux for about 3 hours. The solvents were removed under reduced pressure and MeOH (3.0 ml) was added. The mixture was heated at reflux for about 1 hour and solvents were removed under reduced pressure. The crude product was purified by preparative HPLC on a RAININ™ $C_{18}$ column using a gradient 5% to 35% $CH_3CN/0.1\%$ Tfa over 45 minutes. Product fractions were combined, concentrated and re-lyophilized from dilute HCl to yield product (9.8 mg, 8%) as the dihydrochloride. Mass spec. 509.3 MH+.

Example 8

7-((1H-Imidazol-4-yl)methyl)-2-(2-methoxyphenyl)-8-(1-methylpropyl)-5,6,7,8-tetrahydroimidazo[1,2a]pyrazine Example 8 was synthesized according to Schemes 1 and 8 with Steps 1.a. and 1.b. being replaced by Steps 8.a. through 8.b. and Step 1.g. and 1.h. being replaced with Step 8.c. and 8.d.

Scheme 8:

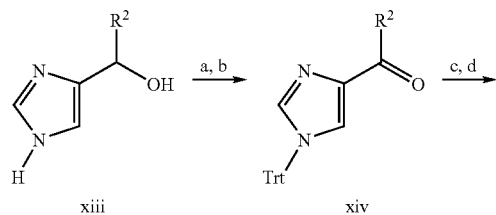

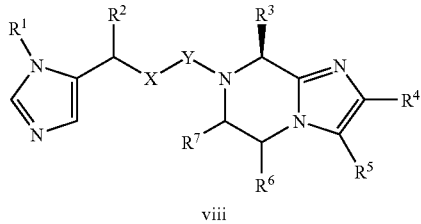

8.a. $(C_6H_5)_3CCl/Et_3N/DMF$
8.b. $SO_3$-pyridine complex/$Et_3N$/DMSO
8.c. Compound vii/$NaBH(OAc)_3$/$CH_2Cl_2$
8.d. Tfa/$iPr_3SiH$

Step 8.a.
4-Hydroxymethyl-1-triphenylmethyl-imidazole

4-Hydroxymethylimidazole hydrochloride (compound xiii where $R^2$ is H) (2.50 g, 18.6 mmol) and $Et_3N$ (2.59 ml, 18.6 mmol) were combined in DMF (30 ml) and stirred at room temperature. A solution of chlorotriphenylmethane (5.19 g, 18.6 mmol) in DMF (25 ml) was added dropwise at room temperature and the resulting mixture was stirred at room temperature for about 23 hours and then poured into ice water (300 ml). The product was filtered off, washed with cold water (75 ml) and triturated with p-dioxane (30 ml). The product was filtered off and dried under reduced pressure to yield product (4.96 g, 78%). NMR (300 MHZ, DMSO-$d_6$, 30° C.) 7.3-7.5 (9H, m), 7.25-7.35 (1H, d), 7.0-7.2 (6H, m), 6.7-6.75 (1H, s), 4.15-4.2 (2H, m).

Step 8.b.
1-Triphenylmethyl-imidazole4-carboxaldehyde

The product from Step 8.a. (2.04 g, 6.00 mmol) was suspended in DMSO (10.0 ml) and $Et_3N$ (3.34 ml, 24.0 mmol) and $SO_3$-pyridine complex (2.39 g, 15.0 mmol) were added at room temperature. The mixture was warmed at about 110° C. for about 1 hour and then allowed to cool. The mixture was poured into 150 ml $H_2O$ and the product was filtered off. The residue was treated with saturated $NaHCO_3$ solution (50 ml) and extracted 2×100 ml $CH_2Cl_2$. The combined $CH_2Cl_2$ layers were washed with 5% citric acid solution (100 ml), dried over $Na_2SO_4$, filtered and concentrated under reduced pressure. The residue was crystallized from MeOH and $H_2O$. Yield=1.08 g (53%).

Step 8.c. 7-((1-Triphenylmethyl-imidazol-4-yl)methyl)-2-(2-methoxyphenyl)-8-(1-methylpropyl)-5,6,7,8-tetrahydro-imidazo[1,2-a]pyrazine 8-(1-Methylpropyl)-2-(2-methoxyphenyl)-5,6,7,8-tetrahydro-imidazo[1,2-a]pyrazine dihydrochloride (compound vii where $R^3$ is 1-methylpropyl, $R^4$ is 2-methoxyphenyl, and $R^5$—$R^7$ are H) (from Step 4.g.)(179 mg, 0.50 mmol) and the product from Step 8.b. (compound xiv where $R^2$ is H) (338 mg, 1.00 mmol) were combined in 1,2-dichloroethane (2.0 ml). $NaBH(OAc)_3$ (212 mg, 1.00 mmol) was added and the reaction was allowed to stir at room temperature for about 1 hour. The reaction mixture was poured onto a silica gel column and the product was eluted using EtOAc as eluant. Product fractions were combined and concentrated to yield pure product as white foam (150 mg, 49%). Mass spec. 608.2, MH+.

Step 8.d. 7-((1H-Imidazol-4-yl)methyl)-2-(2-methoxyphenyl)-8-(1-methylpropyl)-5,6,7,8-tetrahydroimidazo[1,2a]pyrazine The product from Step 8.c. (compound viii where R¹ is triphenylmethyl, R³ is isobutyl, R⁴ is 2-methoxyphenyl, and R², R⁵—R⁷ are H, and X and Y constitute a bond) (160 mg, 0.26 mmol) was treated with Tfa (10 ml) containing iPr₃SiH (0.20 ml, 1.0 mmol) for about 45 minutes at room temperature under N₂. The solvents were removed under reduced pressure and the product was purified by preparative HPLC on a RAININ™ C₁₈ column using a gradient of 20-40% CH₃CN/0.1% Tfa over 45 minutes. Product fractions were concentrated to about ½ volume and lyophilized. The product was re-lyophilized twice from dilute HCl to yield pure product (77 mg, 66%). Mass spec. 366.2 MH⁺.

Example 9

7-((4-Imidazolyl)carbonyl)-2-(2-methoxyphenyl)-8-(1-methylpropyl)-5,6,7,8-tetrahydroimidazo[1,2a]pyrazine Example 9 was prepared according to Schemes 1 and 4 in a manner analogous to example 4, starting with imidazole-4-carboxylic acid in place of imidazole-4-acetic acid in Step 4.a. Mass spec 380.3 MH⁺.

Example 10

7-(1-(4-Cyanophenylmethyl)-imidazol-5-yl)methyl-2-(2-methoxyphenyl)-8-(1-methylpropyl)-5,6,7,8-tetrahydroimidazo[1,2a]pyrazine The product from Step 8.c. (compound viii where R¹ is triphenylmethyl, R³ is isobutyl, R⁴ is 2-methoxyphenyl, R², R⁵, R⁶, and R⁷ are H, and X and Y constitute a bond) (150 mg, 0.25 mmol) was dissolved in CH₃CN (2.0 ml). α-Bromo-p-tolunitrile (49 mg, 0.25 mmol) was added and the mixture was refluxed for about 1 hour. MeOH (3.0 ml) was added and the mixture was refluxed again for about 1 hour. Solvents were removed under reduced pressure, Et₂O (10 ml) was added and the product was extracted with 1.0% Tfa (2×15 ml). The crude product was purified by preparative HPLC on a RAININ™ C₁₈ column using a gradient of 20-50% CH₃CN/0.1% Tfa over 40 minutes. Product fractions were concentrated to about ½ volume and lyophilized. The product was re-lyophilized twice from dilute HCl to yield pure product (52 mg, 35%). Mass spec. 481.4 MH⁺.

Example 11

5-(2-(1-(4-Cyanophenylmethyl)-imidazol-5-yl)-1-oxo-ethyl)-5,6-dihydro-2-phenyl-1H-imidazo[1,2-a][1,4]benzodiazepine Example 11 was synthesized according to Schemes 5 and 11.

Scheme 11:

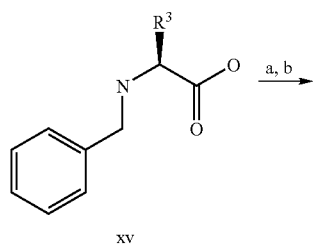

xv

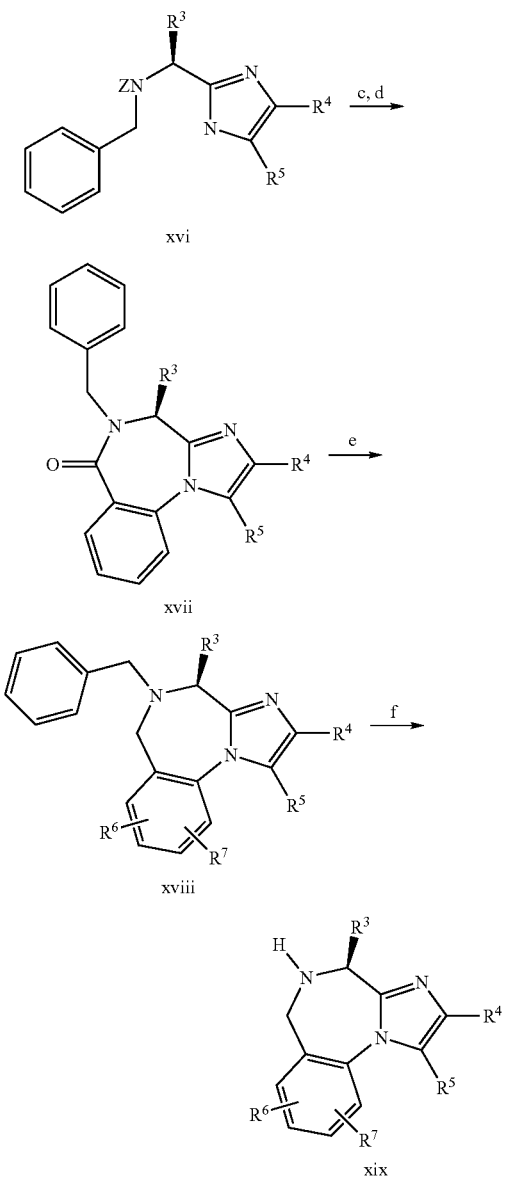

xvi xvii xviii xix 11.a. Cbz—OSu/K₂CO₃/CH₃CN/H₂O,
11.b. Cs₂CO₃/R⁴COCHBrR⁵ then NH₄OAc/xylenes,
11.c. HBr/HOAc,
11.d. 2-Fluorobenzoyl chloride/Et₃N/CH₂Cl₂, then refluxing DMF,
11.e. BH₃/THF,
11.f. 1-Chloroethylchloroformate/CH₂Cl₂

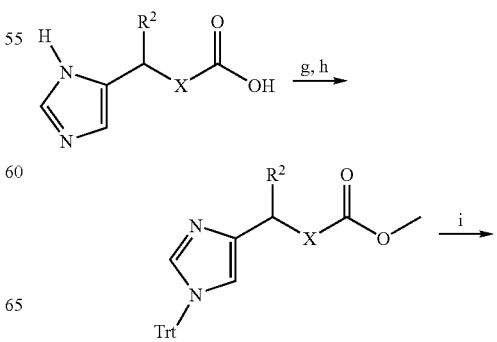

-continued

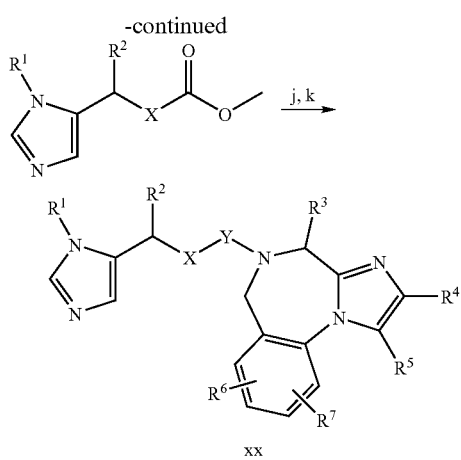

11.g. MeOH/HCl
11.h. Trt—Cl/Et₃N/DMF
11.i. R¹—Br/EtOAc then MeOH
11.j. MeOH/H₂O/NaOH
11.k. DCC/HOAt/DMF/compound xix/Et₃N

Step 11.a. (N-(Phenylmethoxy)carbonyl)-N-(phenylmethyl)-glycine

A solution of Cbz-OSu (6.18 g, 24.8 mmol) in $CH_3CN$ (55 ml) was added to a solution of N-benzylglycine hydrochloride (compound xv, where $R^3$ is H), (5.00 g, 24.8 mmol) and $K_2CO_3$ (6.84 g, 49.6 mmol) in $H_2O$ (35 ml) and the mixture was stirred vigorously for about 2 hours. The mixture was concentrated to about 35 ml and washed with $Et_2O$ (2×25 ml). The aqueous layer was acidified to about pH=1 by careful addition of concentrated HCl and the product was extracted with EtOAc (2×50 ml). The EtOAc layers were combined and dried over $Na_2SO_4$, filtered and concentrated under reduced pressure to a clear, colorless oil (7.40 g, 99.7%). NMR (300 MHZ, DMSO-$d_6$, 30° C.) 12.5-12.8 (1H, s broad), 7.1-7.5 (10H, m), 5.0-5.2 (2H, s), 4.4-4.6 (2H, d), 3.8-4.0 (2H, s).

Step 11.b. 2-((N-(Phenylmethoxy)carbonyl)-N-(phenylmethyl)amino)-methyl)-4-phenyl-imidazole The product from Step 11.a. (7.18 g, 24.0 mmol) was dissolved in DMF (50 ml) and $Cs_2CO_3$ (3.91 g, 12.0 mmol) in $H_2O$ (20 ml) was added and the mixture was swirled until homogeneous. Solvents were removed under reduced pressure, the residue was dissolved in DMF (25 ml) and 2-bromo-2'-methoxy acetophenone (4.78 g, 24.0 mmol) in DMF (25 ml) was added. The mixture was stirred about 30 minutes at room temperature then concentrated under reduced pressure. The resulting keto-ester was dissolved in xylenes (125 ml) and filtered. $NH_4OAc$ (28.0 g, 0.36 mol) was added and the mixture was heated at reflux for about 2 hours with removal of excess $NH_4OAc$ and liberated $H_2O$ using a Dean-Stark trap. The reaction mixture was cooled and washed with saturated $NaHCO_3$ solution (100 ml), dried over $Na_2SO_4$, filtered and concentrated under vacuum to 9.70 g (102%), which was used without further purification. Mass spec. 398.2 $MH^+$.

Step 11.c. 2-(N-(Phenylmethyl)amino)-methyl)-4-phenyl-imidazole

The product from Step 11.b., (compound xvi where $R^3$ and $R^5$ are H, and $R^4$ is 2-methoxyphenyl), (9.7 g, 24.0 mmol) was treated with 30% HBr/HOAc (85 ml) at room temperature for about 2 hours. $Et_2O$ (100 ml) was added to the resulting slurry and the product was filtered off, washed with $Et_2O$ and dried under reduced pressure to yield product (7.70 g, 75%) as an off-white solid. Mass spec. 264.3 $MH^+$, NMR (300 MHZ, DMSO-$d_6$, 30° C.) 8.5-11.0 (3H, s broad), 8.1-8.2 (1H, s), 7.8-7.9 (2H, m), 7.55-7.65 (2H, m), 7.45-7.55 (2H, m), 7.35-7.5 (4H, m), 4.5-4.7 (2H, s), 4.3-4.5 (2H, s).

Step 11.d. 6-Oxo-2-phenyl-5-(phenylmethyl)-1H-imidazo[1,2a][1,4]benzodiazepine The product from Step 11.c. (4.25 g, 10.0 mmol) was suspended in THF (35 ml) and $Et_3N$ (4.9 ml, 35.0 mmol) was added at room temperature. 2-Fluorobenzoyl chloride (1.19 ml, 10.0 mmol) was added and the mixture was stirred about 1 hour at room temperature. Solvents were removed under reduced pressure and the residue was taken up in $CH_2Cl_2$ (50 ml) and washed with saturated NaCl solution (2×25 ml). The $CH_2Cl_2$ layer was dried over $NASO_4$, filtered and concentrated under reduced pressure. The residue was dissolved in DMF (35 ml), $K_2CO_3$ (1.38 g, 10.0 mmol) was added and the mixture was heated at reflux for about 1 hour. Solvents were removed under reduced pressure, the intermediate was dissolved in EtOAc (50 ml) and washed 2× with saturated $NaHCO_3$ and 1× with saturated NaCl solution. The EtOAc layer was dried over $Na_2SO_4$, filtered and concentrated to about 25 ml. $Et_2O$ (about 25 ml) was added and the product was filtered off (1.46 g). Mother liquors were purified by flash chromatography on silica gel using 1:1/hexanes:EtOAc as eluant to provide a second crop of pale orange foam (0.63 g) which was used in subsequent reactions. Total yield=57%, mass spec 366.2 $MH^+$. NMR (300 MHZ, DMSO-$d_6$, 30° C.) 8.25-8.35 (1H, s), 7.95-8.05 (1H, d,d), 7.6-7.9 (4H, m), 7.5-7.7 (1H, t), 7.3-7.5 (2H, t), 7.2-7.4 (6H, m), 4.6-5.0 (2H, s broad), 4.4-4.6 (2H, s).

Step 11.e. 2-Phenyl-5-(phenylmethyl)-1H-imidazo[1,2a][1,4]benzodiazepine

The product from Step 11.d. (compound xvii where $R^3$ and $R^5$ are H, and $R^4$ is 2-methoxyphenyl) (0.63 g, 1.73 mmol) was dissolved in THF and 1$\underline{M}$ borane/THF complex (16.0 ml, 16.0 mmol) was added at room temperature. The mixture was heated at reflux for about 1 hour and then cooled. 4$\underline{N}$ HCl (12 ml) was added and the mixture was heated at reflux for about ½ hour. The mixture was cooled to room temperature, concentrated to about 12 ml under reduced pressure, and then neutralized by careful addition of solid $NaHCO_3$. The product was extracted 2× with EtOAc, dried over $Na_2SO_4$, filtered, then concentrated under reduced pressure. The residue was dissolved in methanol (10 ml) and treated with concentrated HCl (0.5 ml) to convert product to the hydrochloride salt. The solution was concentrated and the product was obtained by crystallization from MeOH/$Et_2O$. Yield=444 mg (60%) Mass Spec 352.2 $MH^+$, NMR (300 MHZ, DMSO-$d_6$, 30° C.) 8.5-8.6 (1H, s), 7.9-8.0 (2H, d), 7.65-7.9 (5H, m), 7.4-7.6 (6H, m), 7.3-7.4 (1H, t), 4.5-6.5 ($H_2O$), 4.4-4.6 (2H, s), 4.2-4.3 (2H, s), 4.1-4.25 (2H, s).

Step 11.f. 2-Phenyl-1H-imidazo[1,2a][1,4]benzodiazepine

The product from Step 11.e. (compound xviii where $R^3$, $R^5$, $R^6$, and $R^7$ are H, and $R^4$ is 2-methoxyphenyl) (382 mg, 0.90 mmole) was distributed between saturated NaHCO$_3$ solution and CH$_2$Cl$_2$. The CH$_2$Cl$_2$ layer was dried over Na$_2$SO$_4$, filtered and 1-chloroethylchloroformate (108 ul, 1.00 mmol) was added at room temperature. The mixture was stirred overnight at room temperature. The CH$_2$Cl$_2$ layer was washed with saturated NaHCO$_3$ solution, dried over Na$_2$SO$_4$, filtered and concentrated under reduced pressure. The residue was dissolved in MeOH (5.0 ml) and stirred at room temperature for about 1 hour. The methanolic solution was treated with concentrated HCl (0.5 ml) to convert product to the hydrochloride salt. The solution was concentrated and the product obtained by crystallization from MeOH/Et$_2$O. Yield=186 mg (62%), mass spec 262.2 MH$^+$, NMR (300 MHZ, DMSO-d$_6$, 30° C.) 10.7-11.1 (1-2H, s broad), 8.5-8.6 (1H, s), 8.1-8.6 (1-2H, s broad), 7.9-8.05 (2H, d,d), 7.7-7.85 (3H, m), 7.55-7.65 (1H, m), 7.45-7.55 (2H, t), 7.3-7.45 (1H, m), 4.2-4.4 (2H, s), 4.1-4.3 (2H, s).

Step 11.g. Methyl, 4-imidazole acetate

4-Imidazoleacetic acid sodium salt dihydrate (15.3 g, 83.1 mmol) was suspended in toluene (100 ml) and concentrated to remove water of hydration. The residue was dissolved in MeOH (235 ml) and the solution was cooled in an ice/water bath under N$_2$. Gaseous HCl was added for 20 minutes and the resulting solution was stirred for 2 hours at room temperature. The mixture was concentrated to dryness. The residue was re-dissolved in MeOH (235 ml), filtered, and the solution was cooled in an ice/water bath under N$_2$. Gaseous HCl was added for 20 minutes and the resulting solution was stirred for 2 hours at room temperature. Toluene (150 ml) was added and the mixture was concentrated to dryness and dried to yield product (16.6 g, 113%) which was used in the next Step without further purification. Mass spec. 141.2 MH$^+$, NMR (300 MHZ, DMSO-d$_6$, 30° C.) 8.8-8.9 (1H, s), 7.5-7.7 (1H, s), 3.7-3.9 (2H, s), 3.6-3.7 (3H, s).

Step 11.h. Methyl, 1-Triphenylmethyl-4-imidazole acetate

The product from Step 11.g. (crude, 83.1 mmol) was dissolved in DMF (70 ml) under N$_2$ and Et$_3$N (35.6 ml, 241 mmol) was added in an exothermic reaction. After cooling to room temperature, Chlorotriphenylmethane (23.2 g, 83.1 mmol) was added and the mixture was stirred overnight at room temperature. The mixture was poured into H$_2$O (300 ml) and extracted once with 300 ml EtOAc and once with 150 ml EtOAc. The combined EtOAc layers were washed with saturated NaHCO$_3$ solution (300 ml), dried over Na$_2$SO$_4$, filtered and concentrated to an oil which crystallizes to yield a tan solid (30.9 g, 97%). Mass spec. 382.9 MH$^+$.

Step 11.i. Methyl, 1-(cyanophenylmethyl)-5-imidazole acetate

The product from Step 11.h. (15.0 g, 39.2 mmol) was dissolved in EtOAc (80 ml) with warming. α-Bromo-p-toluonitrile (7.69 g, 39.2 mmol) was added and the mixture was warmed at 65-70° C. for 2.5 hours. A first crop was filtered off, washed with EtOAc, and dried to 9.27 g. The filtrate was concentrated to about 80 ml and heated at 65-70° C. for an additional 14 hours. A second crop was filtered off, washed with EtOAc, and dried to 9.40 g. The filtrate was concentrated to about 30 ml and heated at 65-70° C. for an additional 48 hours. A third crop was filtered off, washed with EtOAc, and dried to 0.87 g. The combined intermediates were suspended in MeOH (350 ml) and heated at reflux for ½ hour. The solvent was distilled under reduced pressure and the resulting solid was triturated with EtOAc (250 ml). The resulting solid was suspended in CH$_2$Cl$_2$ (500 ml), saturated NaHCO$_3$ (500 ml) was added and the mixture was stirred for 3 hours. The aqueous layer was removed and the CH$_2$Cl$_2$ layer was dried over Na$_2$SO$_4$, filtered, and concentrated under reduced pressure to yield an oil which crystallized on standing (8.08 g, 81%). Mass spec. 256.2 MH$^+$.

Step 11.j. 1-(Cyanophenylmethyl)-5-imidazole acid hydrochloride

The product from Step 11.i. (8.0 g, 31.3 mmol) was dissolved in THF (200 ml) and 2N NaOH (16.7 ml, 33.4 mmol) was added. The mixture was stirred 48 hours at room temperature. The solution was neutralized to pH=2.0 by addition of 2N HCl and the solution was concentrated under reduced pressure to a tan solid. The residue was stirred with MeOH (200 ml), solids were removed by filtration and the filtrate was concentrated under reduced pressure and dried to yield product (5.85 g, 67%). Mass spec. 242.1 MH$^+$, NMR (300 MHZ, DMSO-d$_6$, 30° C.) 9.3-9.4 (1H, s), 7.8-7.95 (2H, d), 7.55-7.7 (1H, s), 7.4-7.6 (2H, d), 5.5-5.7 (2H, s), 3.8-4.0 (2H, s).

Step 11.k. 5-(2-(1-(4-Cyanophenylmethyl)-imidazol-5-yl)-1-oxo-ethyl)-2-phenyl-1H-imidazo[1,2-a][1,4]benzodiazepine The product from Step 11.j (77 mg, 0.24 mmol) was combined with DCC (49 mg, 0.24 mmol), HOAt (33 mg, 0.24 mmol), NMM (110 uL, 1.0 mmol) and the product from Step 11.f. (75.0 mg, 0.225 mmol) in DMF (3.0 ml) and the reaction was allowed to stir about 3 days at room temperature. Solvents were removed under reduced pressure and the crude product was purified by preparative HPLC on a RAININ™ C$_{18}$ column using a gradient of 15-40% CH$_3$CN/ 0.1% Tfa over 45 minutes. Product fractions were concentrated to about 12 volume and lyophilized. The product was re-lyophilized twice from dilute HCl to yield pure product (71 mg, 61%). Mass spec. 485.3 MH$^+$, NMR (300 MHZ, DMSO-d$_6$, 30° C.) 9.3-9.4 (1H, d), 8.6-8.8 (1H, d), 8.0-8.15 (2H, d), 7.3-8.0 (12H, m), 5.5-5.7 (2H, s), 4.9-5.1 (1H, s), 4.75-4.9 (1H, s), 4.65-4.8 (1H, s), 4.45-4.6 (1H, s), 4.25-4.4 (1H, s), 4.15-4.3 (1H, s).

Example 12

7-(2-(4-Cyanophenylmethyl)-imidazol-5-yl)-1-oxo-ethyl)-2-(2-methoxyphenyl)-5,6,7,8-tetrahydroimidazo[1,2-a]pyrazine Steps 12.a. through 12.d. were performed in a manner analogous to Scheme 1, steps 1.c. through 1.f, starting with Cbz-Gly-OH in place of Cbz-(L)-Ile-OH in Step 12.a. Step 12.f. was performed in a manner analogous to Scheme 1, Step 1.g., substituting the product from Step 11.j. for the product from Step 1.b. Mass spec. 453.3 MH$^+$, NMR (300 MHZ, DMSO, 90° C.) 9.1-9.2 (1H, d), 7.95-8.05 (1H, d,d), 7.9-8.0 (1H, s), 7.8-7.9 (2H, d), 7.55-7.6 (1H, s), 7.5-7.6 (2H, d), 7.35-7.5 (1H, m), 7.15-7.25 (1H, d), 7.0-7.15 (1H, t), 5.4-5.7 (2H, s), 4.9-5.1 (2H, s broad), 4.15-4.4 (2H, s broad), 4.05-4.2 (2H, s), 3.9-4.1 (2H, s broad), 3.9-4.0 (3H, s).

Example 13

7-(2-Amino-1-oxo-3-thiopropyl)-8-(mercaptoethyl)-2-(2-methoxyphenyl)-5,6,7,8-tetrahydroimidazo[1,2a]pyrazine disulfide Steps 13.a. through 13.d. were performed in a manner analogous to Scheme 1, steps 1.c. through 1.f. Cbz-(L)-Asp(OBz)-OH was substituted in place of Cbz-(L)-Nle-OH in Step 13.a. and 6.0 mmol $BH_3$ per 1.0 mmol of compound vi (where $R^3$ is —$CH_2CO_2H$, $R^4$ is 2-methoxyphenyl and $R^5$ and $R^6$ are H) was used in Step 13.d. Also, the dried EtOAc layer of Step 13.d. was concentrated to a solid and used without conversion to the hydrochloride salt.

Steps 13.e. through 13.j. were performed according to Scheme 13:

Scheme 13:

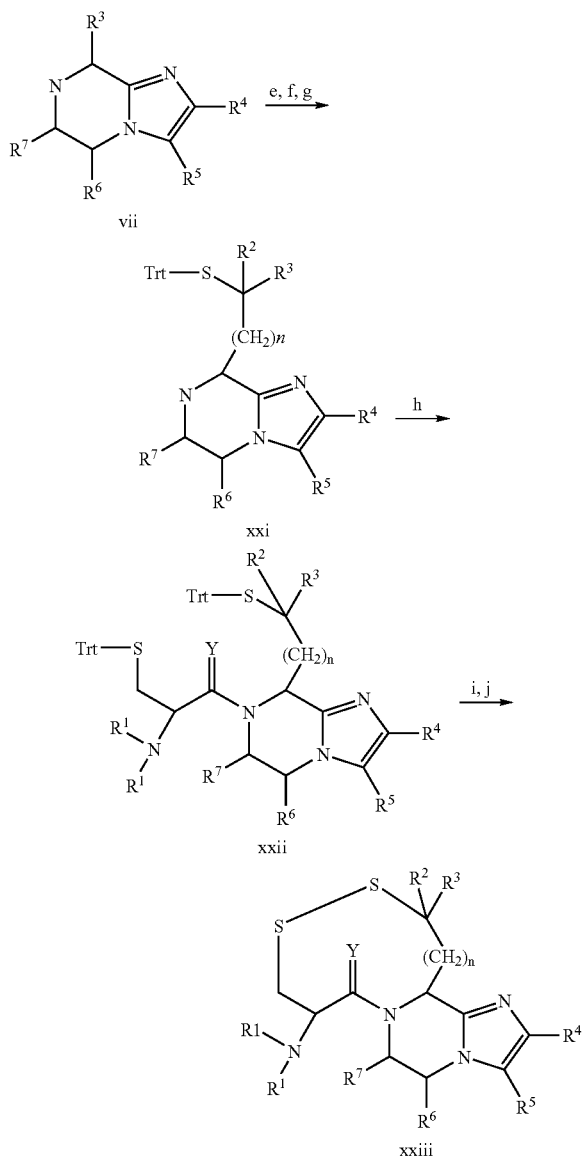

13.e. $(Boc)_2O$/NaOH/THF/$H_2O$
13.f. $(C_6H_5)_3$P/DEAD/Trt——SH/THF
13.g. 20% Tfa/$CH_2Cl_2$
13.h. Boc-(L)-Cys(Trt)-OH/EDC/HOAt/NMM/THF
13.i. Tfa/iPr$_3$SiH/$CH_2Cl_2$
13.j. air at pH 7.2-7.5

Step 13.e. 7-((1,1-Dimethylethoxy)carbonyl)-8-(2-hydroxyethyl)-2-(2-methoxyphenyl)-5,6,7,8-tetrahydro-imidazo[1,2-a]pyrazine 8-(2-Hydroxyethyl)-2-(2-methoxyphenyl)-5,6,7,8-tetrahydro-imidazo[1,2-a]pyrazine (compound vii, where $R^3$ is 2-hydroxyethyl, $R^4$ is 2-methoxyphenyl, and $R^5$, $R^6$ and $R^7$ are H) from Step 13.d. (3.70 g, 13.6 mmol) was dissolved in THF (50 ml) and $H_2O$ (10 ml) was added. Di-tert-butyldicarbonate (3.25 g, 14.9 mmol) was added and the reaction was stirred vigorously for about 3 hours while maintaining the reaction pH at about 8.5 by addition of 2.5N NaOH solution. Solvents were removed under reduced pressure and the residue was distributed between EtOAc (25 ml) and $H_2O$ (25 ml). The product was extracted with 2×25 ml EtOAc and the combined extracts were dried over $Na_2SO_4$, filtered and concentrated. The crude product was purified by flash chromatography on silica gel using 3:2/EtOAc/hexanes as eluant. The combined product fractions were concentrated to a white foam and dried to yield 2.95 g, (58%) of the desired product. Mass spec 374.3 MH$^+$, NMR (300 MHZ, DMSO, 30° C.) 7.95-8.05 (1H, d,d), 7.45-7.55 (1H, s), 7.1-7.25 (1H, m), 7.0-7.1 (1H, m), 6.9-7.0 (1H, m), 5.1-5.3 (1H, m), 4.1-4.4 (1H, d broad), 4.0-4.15 (1H, m), 3.8-4.0 (1H, m), 3.85-3.9 (3H, s), 3.5-3.7 (2H, t), 3.2-3.5 (1H, t broad), 3.25-3.25 (1H, s), 1.8-2.2 (2H, m), 1.35-1.5 (9H, s).

Step 13.f. 7-((1,1-Dimethylethoxy)carbonyl)-2-(2-methoxyphenyl)-5,6,7,8-tetrahydro-8-(2-((triphenylmethyl)thio)ethyl)-imidazo[1,2-a]pyrazine Triphenylphosphine (4.08 g, 15.5 mmol) was dissolved in THF (25 ml), cooled to about 0° C. under $N_2$ and Diethylazodicarboxylate (2.45 ml, 15.54 mmol) was added at a dropwise rate so that the reaction temperature was maintained at about <3° C. Stirring was continued for about 12 hour at 0° C. A mixture of the triphenylmethanethiol (4.30 g, 15.54 mmol) and the product from Step 13.e. (2.90 g, 7.77 mmol) in THF (25 ml) was added at a dropwise rate. The resulting mixture was stirred for about 1 hour at about 0° C. and then allowed to warm to room temperature. The mixture was concentrated under reduced pressure and the residue dissolved in ether (40 ml) and allowed to stand overnight. The solid was filtered off and the filtrate was concentrated then purified by flash chromatography on silica gel using 4:1/hexanes:EtOAc and then 4:1/hexanes:EtOAc as eluants. The product fractions were combined and concentrated under reduced pressure to obtain a pale yellow foam (5.49 g, 111%) which was used without further purification. Mass spec. 632.4 MH$^+$.

Step 13.g. 2-(2-Methoxyphenyl)-5,6,7,8-tetrahydro-8-(2-((triphenylmethyl)thio)ethyl)-imidazo[1,2-a]pyrazine The product from Step 13.f. (2.50 g, 3.96 mmol) was dissolved in $CH_2Cl_2$ (16.0 ml) and treated with Tfa (4.0 ml) at room temperature under $N_2$ for about 3.5 hours. The reaction was then poured cautiously into a saturated NaHCO$_3$ solution (150 ml) and the product was extracted with $CH_2Cl_2$ (2×50 ml), dried over $Na_2SO_4$, filtered and concentrated under reduced pressure. The crude product was purified by flash chromatography on silica gel using 9:1/hexanes:EtOAc and then 100% EtOAc as eluants. Product fractions were combined and concentrated under reduced pressure to obtain a white foam (1.35 g, 64%) which was used without further purification. Mass spec. 532.4 MH$^+$.

Step 13.h. 7-(2-(((1,1-Dimethylethoxy)carbonyl) amino)-1-oxo-3-((triphenylmethyl)thio)-propyl)-2-(2-methoxyphenyl)-5,6,7,8-tetrahydro-8-(2-((triphenylmethyl)thio)ethyl)-imidazo[1,2-a]pyrazine A mixture of the product from Step 13.g. (compound xxi, where $R^2$, $R^3$, $R^5$, $R^6$, and $R^7$ are H, $R^4$ is 2-methoxyphenyl, and n is 1) (1.30 g, 2.45 mmol), Boc-(L)-Cys(Trt)-OH (1.14 g, 2.45 mmol), NMM (270 uL, 2.45 mmol), and HOAt (333 mg, 2.45 mmol) in THF (20 ml) was treated with EDC (470 mg, 2.45 mmol) at room temperature under $N_2$. The reaction was stirred overnight and then concentrated under reduced pressure. Saturated $NaHCO_3$ solution (25 ml) was added and the product was extracted with a 3:2 mixture of hexanes: EtOAc. The extracts were applied to a silica gel column and the product was eluted with 3:2/hexanes:EtOAc. Product fractions were combined and concentrated under reduced pressure to obtain a white foam (2.31 g, 97%) which was used without further purification. Mass spec. 977.6 $MH^+$.

Step 13.i. 7-(2-Amino-1-oxo-3-thiopropyl)-8-(mercaptoethyl)-2-(2-methoxyphenyl)-5,6,7,8-tetrahydroimidazo[1,2a]pyrazine A solution of the product from Step 13.h. (2.25 g, 2.31 mmol) (compound xxii, where each of $R^1$, $R^2$, $R^3$, $R^5$, $R^6$, and $R^7$ are H, $R^4$ is 2-methoxyphenyl, Y is =O, and n is 1) in $CH_2Cl_2$ (16.0 ml) was treated with Tfa (4.0 ml) for about ½ hour. $(iPr)_3SiH$ (1.42 ml, 6.93 mmol) was added and the reaction was allowed to stir about 1 additional hour. The mixture was concentrated under reduced pressure and then the product was extracted by trituration with 0.1% Tfa solution (3×20 ml). The extracts were filtered and lyophilized to yield 1.40 g (98%) of a white solid with HPLC purity of about 92%. The crude was further purified by preparative HPLC on a RAININ™ $C_{18}$ column using a gradient of 10-30% $CH_3CN/0.1$% Tfa over 45 minutes. The Product fractions were combined, concentrated under reduced pressure to about ½ volume and used in the next Step without further purification. Mass spec. 393.2 $MH^+$.

Step 13.j. 7-(2-Amino-1-oxo-3-thiopropyl)-8-(mercaptoethyl)-2-(2-methoxyphenyl)-5,6,7,8-tetrahydroimidazo[1,2a]pyrazine disulfide An aqueous solution of the product from Step 13.i. (crude solution, 0.45 mmol) was diluted to 100 ml with 0.1% Tfa and neutralized with 5% $NH_4OH$ solution. Methanol (100 ml) was added to obtain a homogeneous solution. The mixture was stirred overnight while the pH was maintained at about 7.2-7.5. The solution was concentrated to about 25 ml, made basic by addition of neat $NaHCO_3$ and the product was extracted with $CH_2Cl_2$ (3×25 ml). The extracts were poured onto a silica gel column and the product was eluted with, 90.9:1/$CH_2Cl_2$:MeOH:HOAc. Product fractions were combined and concentrated under reduced pressure. The residue was dissolve in 0.5% HCl solution (10 ml) and lyophilized, and then re-lyophilized from $H_2O$ (10 ml) to yield 43 mg (9%) of a pure product. Mass spec. 391.2 $MH^+$. NMR (300 MHZ, DMSO, 30° C.) 8.8-9.2 (2H, S broad), 7.9-8.1 (2H, m), 7.3-7.5 (1H, t), 7.15-7.3 (1H, d), 7.0-7.2 (1H, t), 6.05-6.25 (1H, m), 4.85-5.0 (1H, s broad), 4.7-4.9 (1H, d), 4.2-4.35 (1H, d), 4.0-4.2 (1H, m), 3.9-4.0 (3H, s), 3.55-3.7 (1H, d), 3.3-3.55 (1H, partially obscured by $H_2O$ peak), 2.9-3.1 (1H, t), 2.4-2.8 (4H, m).

Example 14

5-Butyl-7-(2-(4-cyanophenylmethyl imidazol-5-yl)-1-oxo-ethyl)-2-phenyl-5,6,7,8-tetrahydroimidazo[1,2-a]pyrazine Steps 14.a. through 14.d. were performed in a manner analogous to Scheme 1, Steps 1.c. through 1.f. Cbz-(Gly)-OH was substituted in place of Cbz-(L)-Nle-OH in Step 14.a. and Ethyl 2-bromohexanoate was substituted for Ethyl bromoacetate in Step 14.b. Step 14.e. was performed in a manner analogous to Scheme 1, Step 1.g. substituting the product from Step 11.j. for the product from Step 1.b. Mass spec. 479.3 $MH^+$.

Example 15

6-Butyl-7-(2-(4-cyanophenylmethylimidazol-5-yl)-1-oxo-ethyl)-2-(2-methoxyphenyl)-5,6,7,8-tetrahydroimidazo[1,2-a]pyrazine Example 15 was prepared in a manner analogous to Example 14 except Steps 1.d., 1.e., and 1.f. were replace with Steps 15.a and 15.b.

Scheme 15:

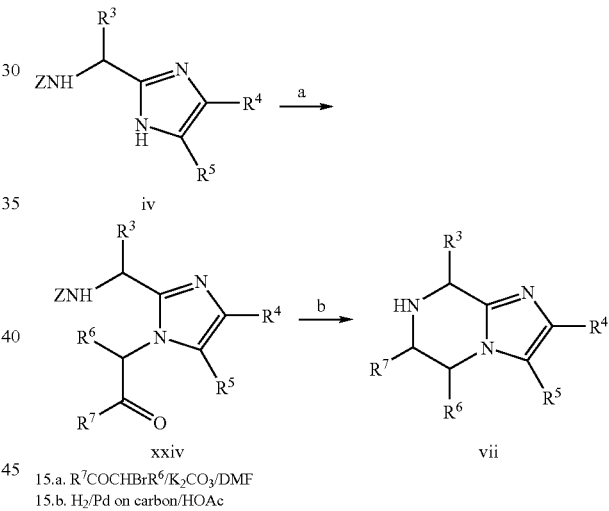

15.a. $R^7COCHBrR^6/K_2CO_3$/DMF
15.b. $H_2$/Pd on carbon/HOAc

Step 15.a. 1-(2-Oxo-hexyl)-2-(1-(((Phenylmethoxy) carbonyl)-amino)-methyl)-4-(2-methoxy phenyl)-imidazole 1-H-2-(1-(((Phenylmethoxy)carbonyl)-amino)-methyl)-4-(2-methoxyphenyl)-imidazole (compound iv, where $R^3$ and $R^5$ are H, and $R^4$ is 2-methoxyphenyl) (790 mg, 2.34 mmol), 1-chloro-2-hexanone (473 mg, 3.51 mmol) and $K_2CO_3$ (469 mg, 4.68 mmol) were combined in DMF (4 ml) and stirred at room temperature for about 42 hours. The reaction was diluted with saturated $NaHCO_3$ (25 ml) and extracted with $Et_2O$ (2×50 ml). The combined $Et_2O$ extracts were dried over $Na_2SO_4$, filtered and concentrated under reduced pressure. The crude product was purified by flash chromatography on silica gel using 3% $MeOH/CH_2Cl_2$ as eluant. Pure product fractions were combined and concentrated under reduced pressure to yield a pale yellow oil (650 mg, 64%) which solidifies on standing. Mass spec. 436.3 $MH^+$.

Step 15.b. 6-Butyl-2-(2-methoxyphenyl)-5,6,7,8-tetrahydro-imidazo[1,2-a]pyrazine The product from Step 15.a. (compound xxiv, where $R^3$, $R^5$ and $R^6$ are H, $R^5$ is 2-methoxyphenyl, and $R^7$ is n-butyl) (650 mg, 1.49 mmol) was dissolved in HOAc (25 ml) containing 10% Pd on carbon (65 mg) and the mixture was hydrogenated under 30 psi $H_2$ for about 6 hours. The catalyst was removed by filtration through diatomaceous earth and the filtrate was concentrated under reduced pressure to yield a pale yellow oil which crystallizes on standing (430 mg, 101%).

Step 15.c. 6-Butyl-7-(2-(4-cyanophenylmethyl)-imidazol-5-yl)-1-oxo-ethyl)-2-phenyl-5,6,7,8-tetrahydroimidazo[1,2-a]pyrazine Example 15 was obtained in Step 15.c. in a manner analogous to Step 1.g., substituting the product of Step 15.b. for the product from Step 1.f. Mass spec. 509.3 MH+.

Example 16

6-Butyl-7-(2-(4-cyanophenylmethyl imidazol-5-yl)-1-oxo-ethyl)-2-phenyl-5,6,7,8-tetrahydroimidazo[1,2-a]pyrazine Example 16 was prepared in a manner analogous to Example 15 starting with 2-Bromoacetophenone in place of 2-Bromo-2'-methoxyacetophenone in Step 1.c. Mass spec. 509.4 MH+.

Example 17

5-Butyl-7-(2-(1-(4-cyanophenylmethyl)-imidazole-5-yl)-1-oxo-ethyl)-2-(2-methoxyphenyl)-5,6,7,8-tetrahydroimidazo[1,2a]pyrazine Example 17 was prepared in a manner analogous to Example 14 starting with 2-Bromoacetophenone in place of 2-Bromo-2'-methoxyacetophenone in Step 1.c. Mass spec. 509.3 MH+.

Example 18

7-(2-(1-(4-Cyanophenylmethyl)-imidazole-5-yl)-1-oxo-ethyl)-8-cyclohexylmethyl)-2-(2-methoxyphenyl)-5,6,7,8-tetrahydroimidazo[1,2a]pyrazine Steps 18.a. through 18.d. were performed in a manner analogous to Scheme 1, Steps 1.c. through 1.f. Cbz-(L)-Cyclohexylalanine was substituted in place of Cbz-(L)-Nle-OH in Step 18.a. Step 18.e. was performed in a manner analogous to Scheme 1, Step 1.g. substituting the product from Step 11.j. for the product from Step 1.b. Mass spec. 549.4 MH+, NMR (300 MHZ, DMSO-$d_6$, 30° C.) 9.15-9.25 (1H, s), 8.05-8.15 (1H, d), 8.0-8.1 (1H, s), 7.8-7.9 (2H, d), 7.6-7.7 (1H, s), 7.5-7.6 (2H, d), 7.4-7.5 (1H, t), 7.15-7.3 (1H, d), 7.05-7.15 (1H, t), 5.85-6.05 (1H, d,d), 5.5-5.6 (2H, s), 4.1-4.5 (5H,m), 3.9-4.1 (3H, s), 3.75-3.9 (1H, m), 1.85-2.1 (3H, m), 1.4-1.8 (4H, m), 0.8-1.4 (7H, m).

Example 19

5-Butyl-7-(2-(1H-imidazole-5-yl)-1-oxo-ethyl)-2-(2-methoxyphenyl)-5,6,7,8-tetrahydroimidazo[1,2a] pyrazine Example 19 was prepared in a manner analogous to example 4 using 5-butyl-2-(2-methoxyphenyl)-5,6,7,8-tetrahydroimidazo[1,2a]pyrazine(compound vii, where $R^3$, $R^5$ and $R^7$ are H, $R^4$ is 2-methoxyphenyl and $R^6$ is n-butyl), as described for example 14, in place of 2-(2-methoxyphenyl)-8-(1-methylpropyl)-5,6,7,8-tetrahydroimidazo[1,2a]pyrazine in Step 19.e. Mass spec. 394.3 MH−.

Example 20

7-(2-(4-Cyanophenylmethyl)-imidazol-5-yl)-1-oxo-ethyl)-2-(2-(phenylmethoxy)-phenyl)-5,6,7,8-tetrahydroimidazo[1,2-a]pyrazine The starting material for Step 20.a. was prepared in a manner analogous to Scheme 1, Steps 1.c. through 1.f. substituting Cbz-(Gly)-OH in place of Cbz-(L)-Nle-OH. Step 20.d. was performed in a manner similar to Scheme 1, Step 1.g., substituting the product from Step 11.j. for the product of Step 1.b.

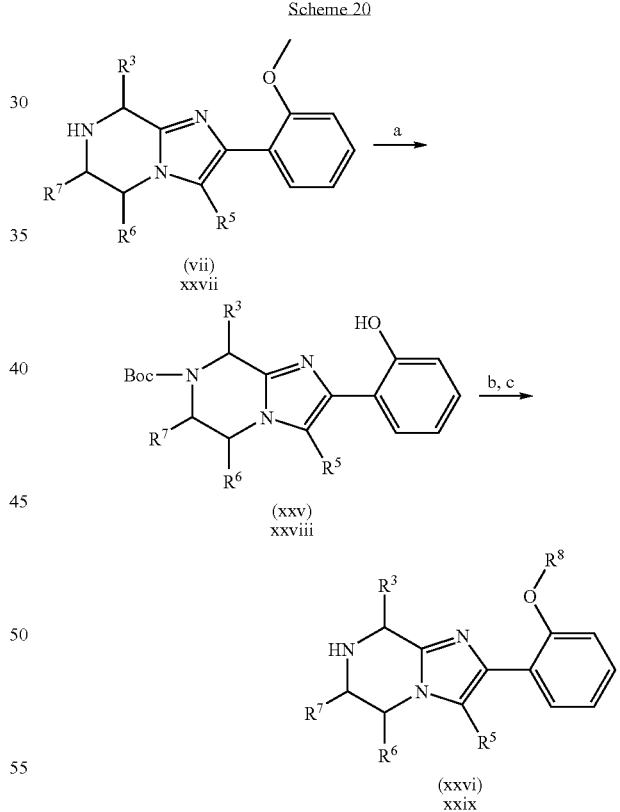

Scheme 20

20.a. BBr$_3$/CH$_2$Cl$_2$/hexanes, then (Boc)$_2$O/NaOH/THF/H$_2$O
20.b. NaH/R$^8$—Br/DMF
20.c. Tfa/iPr$_3$SiH

Step 20.a. 7-((1,1-Dimethylethoxy)carbonyl)-2-(2-Hydroxyphenyl)-5,6,7,8-tetrahydro-imidazo[1,2a] pyrazine 2-(2-Methoxyphenyl)-5,6,7,8-tetrahydroimidazo[1,2a] pyrazine (compound vii, where $R^3$, $R^5$, $R^6$, and $R^7$ are H, and R⁴ is 2-methoxyphenyl) (5.30 g, 23.1 mmol) was dissolved in CH₂Cl₂ (100 ml) and added dropwise over about 15 minutes to a mixture of 1M BBr₃/hexanes (80.3 ml, 80.3 mmol) in CH₂Cl₂ (500 ml) at about 0° C. The mixture was allowed to warm to room temperature and stirred overnight. The de-methylated intermediate was extracted with H₂O (3×240 ml) and the combined aqueous layers were washed with Et₂O (100 ml). The solution was adjusted to a pH of about 8 by addition of 2.5N NaOH, and di-tert-butyldicarbonate (5.55 g, 25.4 mmol) was added in THF (200 ml). The solution was vigorously stirred for about 2 hours while maintaining the solution at pH=8.0-8.5. The mixture was concentrated to about 700 ml and extracted with CH₂Cl₂ (2×100 ml). The combined CH₂Cl₂ layers were dried over Na₂SO₄, filtered, and concentrated under reduced pressure to yield product (7.10 g, 97%) as a tan solid.

Mass spec. 316.2 MH⁺, NMR (300 MHZ, DMSO-d₆, 30° C.) 7.65-7.7 (1H, s), 7.6-7.7 (1H, d,d), 7.0-7.15 (1H, m), 6.75-6.9 (2H, m), 4.6-4.7 (2H, s), 4.0-4.2 (2H, t), 3.75-3.9 (2H, t), 3.3-3.4 (H₂O) 1.4-1.55 (9H, s).

Step 20.b. 7-((1,1-Dimethylethoxy)carbonyl)-2-(phenylmethoxy)-5,6,7,8-tetrahydro-imidazo[1,2a]pyrazine A 60% dispersion of NaH in mineral oil (76 mg, 1.9 mmol) was washed with hexanes (2×5.0 ml) and a solution of 2-(2-Hydroxyphenyl)-5,6,7,8-tetrahydro-imidazo[1,2a]pyrazine from Step 9.a. (500 mg, 1.58 mmol) in DMF (10 ml) was added at room temperature. The reaction was stirred for about 10 minutes and then benzyl bromide (188 uL, 1.58 mmol) was added and the reaction was stirred at room temperature for about 2 hours. The mixture was poured into saturated NaCl solution (40 ml) and extracted with Et₂O (2×50 ml). The Et₂O layers were combined, dried over Na₂SO₄ filtered and concentrated under reduced pressure to yield product (430 mg, 67%) as a viscous yellow oil which crystallized on standing. Mass spec. 406.3 MH⁺.

Step 20.c. 2-(2-(Phenylmethoxy)phenyl)-5,6,7,8-tetrahydroimidazo[1,2a]pyrazine

The product from Step 20.b. (250 mg, 0.62 mmol) was treated with Tfa (15.0 ml) containing iPr₃SiH (505 uL, 2.47 mmol) at room temperature for about 1 hour under N₂. Solvents were removed under reduced pressure and the residue was triturated with Et₂O (2×20 ml), filtered and dried. The residue was used in the next Step without further purification.

Step 20.d. 7-(2-(4-Cyanophenylmethyl)-imidazol-5-yl)-1-oxo-ethyl)-2-(2-(phenylmethoxy)-phenyl)-5,6,7,8-tetrahydroimidazo[1,2-a]pyrazine Example 20 was prepared from the product of Step 20.d. and the product of Step 11j. in a manner analogous to Step 1.g. Mass spec. 529.3 MH⁺.

Example 21

2-(2-Butoxyphenyl)-7-(2-(4-cyanophenylmethyl)-imidazol-5-yl)-1-oxo-ethyl)-5,6,7,8-tetrahydroimidazo[1,2-a]pyrazine Example 21 was prepared in a manner analogous to example 20 using n-Butyl iodide in place of Benzyl bromide in Step 20.b. Mass spec. 495.4 MH⁻.

Example 22

1,2-Dihydro-1-((1H-imidazol-4-yl)methyl)-4-(2-methoxyphenyl)-imidazo[1,2-c][1,4]benzodiazepine The starting material for Step 22.a. was prepared in a manner analogous to Scheme 1, Steps 1.c. substituting Cbz-(Gly)-OH in place of Cbz-(L)-Nle-OH. Step 22.d. and 22.e. were performed in a manner analogous to Step 8.c. and 8.d.

Scheme 22:

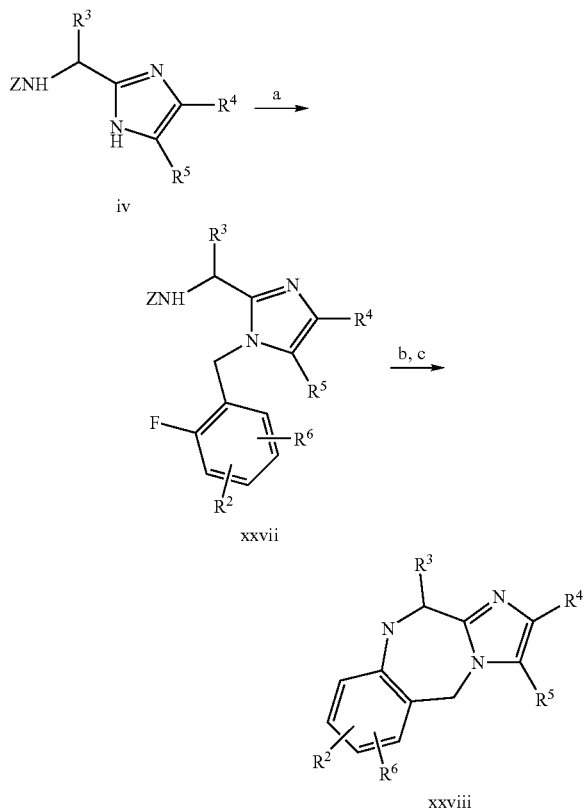

22.a. 2-Fluorobenzyl bromide/K₂CO₃/DMF
22.b. HBr/HOAc
22.c. NMP (reflux)

Step 22.a. 1-((2-Fluorophenyl)-methyl)-2-(1-(S)-(((Phenylmethoxy)carbonyl)-amino)-methyl)-4-(2-methoxyphenyl)-imidazole 1H-2-(1-(S)-(((Phenylmethoxy)carbonyl)-amino)-methyl)-4-(2-methoxyphenyl)-imidazole (1.69 g, 5.00 mmol) was dissolved in DMF (20 ml) and treated with K₂CO₃ (1.38 g, 10.0 mmol) and 2-Fluoro-benzyl bromide (1.21 ml, 10.0 mmol), and the mixture was heated at about 50° C. for about 2 hours. The mixture was concentrated under reduced pressure. The residue was taken in EtOAc (50 ml), washed once with saturated NaHCO₃ solution (25 ml) and once with saturated NaCl solution (25 ml). The EtOAc layer was dried over Na₂SO₄, filtered and concentrated to an oil (2.22 g, 99.6%) which crystallized on standing. Mass spec. 446.2, MH⁺, NMR (300 MHz, DMSO-d₆, 30° C.) 8.05-8.15 (1H, d), 8.75-8.9 (1H, t), 7.5-7.6 (1H, s), 7.1-7.5 (9H, m), 6.9-7.1 (3H, m), 5.3-5.45 (2H, s), 4.9-5.1 (2H, s), 4.3-4.45 (2H, s), 3.8-3.9 (3H, s).

Step 22.b. 2-(Aminomethyl)-1-((2-fluorophenyl)-methyl)-4-(2-methoxyphenyl)-imidazole 1-((2-Fluorophenyl)-methyl)-2-(1-(S)-(((phenylmethoxy) carbonyl)-amino)-methyl)-4-(2-methoxyphenyl)-imidazole (compound xxvi, where $R^2$, $R^3$, $R^5$, and $R^6$ are H and $R^4$ is 2-methoxyphenyl) (2.22 g, 4.99 mmol) was dissolved in 30% HBr/HOAc (25 ml) and the reaction was stirred for about 1 hour at room temperature. $Et_2O$ (100 ml) was added and the resulting slurry was stirred about an additional 15 minutes and the product was filtered off and washed with $Et_2O$ (100 ml). The product was neutralized by addition of saturated $NaHCO_3$ solution (50 ml) and the product was extracted with $CH_2Cl_2$ (2×25 ml). The combined $CH_2Cl_2$ layers were combined, dried over $Na_2SO_4$, filtered and concentrated under reduced pressure to a viscous oil (1.26 g, 81%) which solidified on standing. Mass spec. 312.2 $MH^-$.

Step 22.c. 1,2-Dihydro-4-(2-methoxyphenyl)-imidazo[1,2-c][1,4]benzodiazepine 2-(Aminomethyl)-1-((2-fluorophenyl)-methyl)-4-(2-methoxyphenyl)-imidazole from Step 22.b. (1.26 g, 4.05 mmol) was added to NMP (20 ml) containing $K_2CO_3$ (1.12 g, 8.10 mmol) and the reaction was heated at reflux for about 11 hours. The solvents were distilled off under reduced pressure and $H_2O$ (50 ml) was added. Crude product was filtered off and purified further by flash chromatography on silica gel using $CH_2Cl_2$ and then 19:1/MeOH:$CH_2Cl_2$ as eluants. Product fractions were combined and concentrated under reduced pressure, and then triturated with EtOAc to yield product as a tan solid (329 mg, 28%). Mass spec. 292.3 $MH^+$, NMR (300 MHz, DMSO-$d_6$, 30° C.) 7.95-8.1 (1H, d,d), 7.6-7.65 (1H, s), 7.1-7.2 (1H, m), 6.9-7.1 (4H, m), 6.5-6.65 (2H, m), 5.2-5.4 (2H, s), 4.4-4.5 (2H, s), 3.8-4.0 (3H, s).

Step 22.d. 1,2-Dihydro-4-(2-raethoxyphenyl)-1-((1-(triphenylmethyl)-imidazol-4-yl)methyl)imidazo[1,2-c][1,4]benzodiazepine In a manner similar to Step 8.c., a mixture the product form Step 22.c. (compound xxvii, where $R^2$, $R^3$, $R^5$, and $R^6$ are H and $R^4$ is 2-methoxyphenyl) (146 mg, 0.50 mmol) and 1-Triphenylmethyl-imidazole-4-carboxaldehyde (from Step 8.b.) (338 mg, 1.00 mmol) in $CH_2Cl_2$ (5.0 ml) was treated with acetic acid (1.0 ml) and $NaBH(OAc)_3$ (212 mg, 1.00 mmol) for about 1 hour. Additional 1-Triphenylmethyl-imidazole-4-carboxaldehyde (338 mg, 1.00 mmol), acetic acid (1.0 ml) and $NaBH(OAc)_3$ (212 mg, 1.00 mmol) were added and the mixture was stirred for about 1 hour. EtOAc (25 ml) and concentrated $NH_4OAc$ (3.0 ml) were added and the mixture stirred about 1.5 hours. Saturated $NaHCO_3$ solution was added and the mixture extracted with EtOAc (3×25 ml). The combined EtOAc layers were dried, filtered and concentrated under reduced pressure. Product was purified by flash chromatography on silica gel using 1:1:1/$CH_2Cl_2$:EtOAc:hexanes and then EtOAc as eluant. The combined product fractions were concentrated and dried to 210 mg (68%) under reduced pressure.
Mass spec. 614.3 $MH^+$.

Step 22.e. 1,2-Dihydro-4-(2-methoxyphenyl)-1-((1-(triphenylmethyl)-imidazol-4-yl)methyl)imidazo[1,2-c][1,4]benzodiazepine The product from Step 22.d. was deprotected in a manner analogous to Step 1.h. to yield 104 mg (70%) of the product. Mass spec. 372.3, $MH^+$, NMR (300 MHz, DMSO-$d_6$, 30° C.) 9.0-9.2 (1H, s), 8.05-8.15 (1H, s), 7.9-8.0 (1H, d), 7.7-7.8 (1H, s), 7.3-7.55 (4H, m), 7.1-7.3 (2H, m), 7.0-7.1 (1H, t), 5.6-5.8 (2H, s), 4.55-4.75 (4H, s), 3.9-4.1 (3H, s), 2.7-4.0 ($H_2O$, broad).

Example 23

1-(2-(1-(4-Cyanophenylmethyl)-imidazol-4-yl)-1-oxoethyl)-1,2-dihydro-4-(2-methoxyphenyl)-imidazo[1,2-c][1,4]benzodiazepine Example 23 was prepared according to Scheme 22 and Scheme 11.

Step 23.a. 1-(2-((4-Cyanophenylmethyl)-imidazol-4-yl)-1-oxoethyl)-1,2-dihydro-4-(2-methoxyphenyl) imidazo[1,2-c][1,4]benzodiazepine 1,2-Dihydro-4-(2-methoxyphenyl)-imidazo[1,2-c][1,4] benzodiazepine (compound xxvii, where $R^2$, $R^3$, $R^5$, and $R^6$ are H and $R^4$ is 2-methoxyphenyl) (from Step 22.c.) was combined with DCC (103 mg, 0.50 mmol), HOAt (68 mg, 0.50 mmol), NMM (55 uL, 0.50 mmol) and 1-(4-cyanophenylmethyl)-5-imidazoleacetic acid (the product from Step 11.j.) (160 mg, 0.50 mmol) in DMF (3.0 ml) and the reaction was allowed to stir overnight at room temperature. The reaction was warmed to about 70° C. for about 12 hours and then concentrated under reduced pressure. The crude material was purified by preparative HPLC on a RAININ™ $C_{18}$ column by making a first pass using a gradient of 10-40% $CH_3CN$/0.1% Tfa over 45 minutes, followed by a second pass using a gradient of 20-35% $CH_3CN$/0.1% Tfa over 45 minutes. The product fractions were combined and concentrated to dryness. The product was converted to a dihydrochloride salt by passing a 9:1/$H_2O$:MeOH solution through an ion exchange column (AG 1×2, 200-400 mesh, 100 ml bed, 0.6 meq/ml, chloride form, Biorad, Inc., Hercules, Calif.). Product fractions were again concentrated under reduced pressure and lyophilized from $H_2O$ (10 ml) to yield 21 mg (10%) of the desired product. Mass spec. 515.3 $MH^+$.

Example 24

9-Bromo-1-(2-(1-(4-cyanophenylmethyl)imidazol-4-yl)-1-oxoethyl)-1,2-dihydro-4-(2-methoxyphenyl)-imidazo[1,2-c][1,4]benzodiazepine Example 24 was prepared according to scheme 22, scheme 24 and scheme 1, Step 1.g.

Scheme 24:

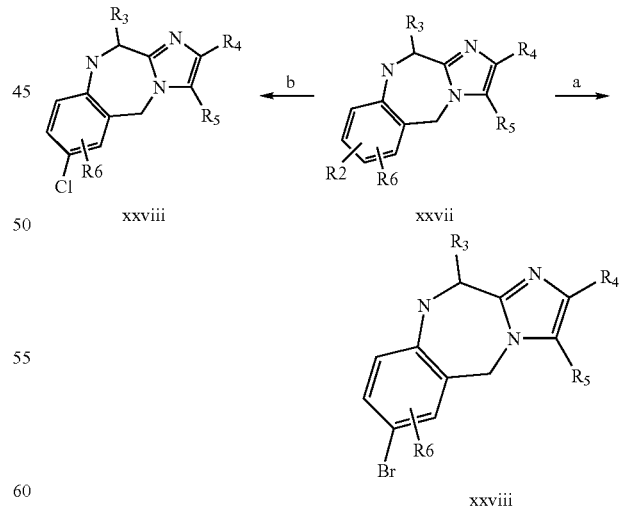

Step 24.a. 9-Bromo-1,2-dihydro-4-(2-methoxyphenyl)-1H-imidazo[1,2-c][1,4]benzodiazepine The product from Step 22.c. (291 mg, 1.00 mmol) was dissolved in acetic acid (10 ml) and $Br_2$ (52 ul) was added dropwise with stirring. Methanol (10 ml) was added to maintain homogeneous solution. When addition was complete, the solvents were evaporated under reduced pressure and the residue was purified by preparative HPLC on a RAININ™ $C_{18}$ column using a gradient of 20-50% $CH_3CN$/0.1% Tfa over 45 minutes with WV detection at 254 nm. Product fractions were concentrated to ½ volume and lyophilized. The lyophilized product was converted to the hydrochloride salt by passing a 20% methanolic solution through an ion exchange column (BioRad AG 1-X2, 200-400 mesh, 0.6 meq/ml, 100 ml, chloride form). The product fractions were combined and concentrated, and lyophilized from $H_2O$ to yield pure product (110 mg, 24%) as the di-hydrochloride. Mass spec. 370.0, 371.9 $MH^+$, NMR (300 MHz, DMSO-$d_6$, 30° C.) 8.05-8.15 (1H, s), 7.9-8.0 (1H, d), 7.4-7.5 (1H, t), 7.3-7.4 (1H, s), 7.2-7.3 (1H, d,d), 7.15-7.25 (1H, d), 7.05-7.15 (1H, t), 6.65-6.75 (1H, d), 5.55-5.7 (2H, s), 4.8-4.95 (2H, s), 3.9-4.0 (3H, s).

Step 24.b. 9-Bromo-1-(2-(1-(4-cyanophenylmethyl) imidazol-4-yl)-1-oxoethyl)-1,2-dihydro-4-(2-methoxyphenyl)-imidazo[1,2-c][1,4]benzodiazepine The product from Step 24.a. (72 mg, 0.177 mmol) was dissolved in DMF (3 ml). To this solution was added NMM (98 ul, 0.89 mmol), 1-(4-cyanophenylmethyl)-5-imidazoleacetic acid (the product from Step 11.j.) (128 mg, 0.36 mmol), HOAt (49 mg, 0.36 mmol) and DCC (74 mg, 0.36 mmol). The reaction was stirred overnight at room temperature and then warmed to 70 C for one hour. The solution was cooled and DCC (74 mg, 0.36 mmol) was added and the solution was stirred at room temperature overnight again. The reaction was heated at 70° C. for one hour and concentrated under reduced pressure. The residue was purified by preparative HPLC on a RAININ™ $C_{18}$ column using a gradient of 25-60% $CH_3CN$/0.1% Tfa over 45 minutes with UV detection at 254 nm. A second purification was required using a gradient of 44-80% $CH_3CN$/0.2% $NH_4OAc$ over 45 minutes Product fractions were concentrated and lyophilized to yield pure product (11 mg, 9%) as an acetate salt. Mass spec. 593.2, 595.3 $MH^+$.

Example 25

9-Chloro-1-(2-(1-(4-cyanophenylmethyl)imidazol-4-yl)-1-oxoethyl)-1,2-dihydro-4-(2-methoxyphenyl)-imidazo[1,2-c][1,4]benzodiazepine Example 25 was prepared according to scheme 22, scheme 24 and scheme 1, Step 1.g.

Step 25.a. 9-Chloro-1,2-dihydro-4-(2-methoxyphenyl)-1H-imidazo[1,2-c][1,4]benzodiazepine The product from Step 22.c. (291 mg, 1.00 mmol) was converted to the dihydrochloride salt by dissolving in methanol (10 ml), adding 5% aqueous HCl (3.0 ml) and concentrating to solids. The residue was dissolved in methanol (5 ml) and HOAc (1.0 ml) and N-chlorosuccinimide (133 mg, 1.0 mmol) was added. The mixture was stirred at room temperature overnight then concentrated under reduced pressure. The residue was distributed between saturated $NaHCO_3$ and $CHCl_3$ and the $CHCl_3$ layer was applied to a silica gel column. The column was eluted first with 3:1/$CHCl_3$:EtOAc and then with 1:1/$CHCl_3$:EtOAc to obtain crude product. This crude material was further purified by preparative HPLC on a RAININ™ $C_{18}$ column using a gradient of 25-60% $CH_3CN$/0.1% Tfa over 45 minutes with UV detection at 254 nm. The clean product fractions were combined and lyophilized to yield 94 mg (17%) of product as the di-Tfa salt. Mass spec. 326.2 $MH^+$, NMR (300 MHz, DMSO-$d_6$, 30° C.) 8.0-8.1 (1H, s), 7.7-7.8 (1H, d,d), 7.4-7.5 (1H, t), 7.2-7.3 (1H, s), 7.15-7.3 (1H, d), 7.1-7.2 (1H, d,d), 7.05-7.15 (1H, t), 6.7-6.8 (1H, d), 5.55-5.65 (2H, s), 4.7-4.8 (2H, s), 3.9-4.0 (3H, s).

Step 25.b. 9-Chloro-1-(2-(1-(4-cyanophenylmethyl) imidazol-4-yl)-1-oxoethyl)-1,2-dihydro-4-(2-methoxyphenyl)-imidazo[1,2-c][1,4]benzodiazepine The product from Step 25.a. (72 mg, 0.13 mmol) was dissolved in DMF (1.5 ml). To this solution was added NMM (114 ul, 1.04 mmol), 1-(4-cyanophenylmethyl)-5-imidazoleacetic acid (compound xii where $R^1$ is (4-cyanophenylmethyl) and $R^2$ is H) (92 mg, 0.26 mmol), and TFFH (69 mg, 0.26 mmol). The reaction was stirred overnight at room temperature and then warmed to 70° C. for one hour. The solution was cooled back to room temperature and 1-(4-cyanophenylmethyl)-5-imidazoleacetic (the product from Step 11.j.) (92 mg, 0.26 mmol), and TFFH (69 mg, 0.26 mmol) were added. The reaction was stirred overnight at room temperature then concentrated under reduced pressure. The residue was purified by preparative HPLC on a RAININ™ $C_{18}$ column using a gradient of 25-60% $CH_3CN$/0.1% Tfa over 45 minutes with UV detection at 254 nm. Product fractions were concentrated and lyophilized. The lyophilized product was converted to the hydrochloride salt by passing a 30% methanolic solution through an ion exchange column (BioRad AG 1-X2, 200-400 mesh, 0.6 meq/ml, 100 ml, chloride form). The product fractions were combined, concentrated and lyophilized from $H_2O$ to yield pure product (59 mg, 73%) as the di-hydrochloride. Mass spec. 549.3 $MH^+$, NMR (300 MHz, DMSO-$d_6$, 30° C.) 9.2-9.3 (1H, s), 8.0-8.1 (1H, s), 7.9-8.1 (1H, d), 7.8-7.9 (2H, d), 7.7-7.85 (2H, m), 7.6-7.75 (1H, d,d), 7.5-7.7 (1H, s), 7.4-7.55 (2H, d), 7.35-7.5 (1H, t), 7.15-7.3 (1H, d), 7.0-7.15 (1H, t), 4.5-6.3 (2H, d,d), 5.4-5.8 (4H, m), 3.9-4.05, (3H, s), 3.5-3.9 (2H, d,d).

Example 26

10-Bromo-1-(2-(1-(4-cyanophenylmethyl)imidazol-4-yl)-1-oxoethyl)-1,2-dihydro-4-(2-methoxyphenyl)-imidazo[1,2-c][1,4]beinzodiazepine Steps 26.a. through 26.c. were performed in a manner analogous to Steps 22.a. through 22.c., substituting 4-bromo-2-fluorobenzyl bromide in place of 2-fluorobenzyl bromide in Step 26.a. The product of Step 26.c. was isolated as the di-hydrochloride salt by stirring a methanolic suspension with a 20% excess of concentrated hydrochloric acid and filtering off the resulting solid. Mass spec. 370.1, 372.1 $MH^+$.

Step 26.d. 10-Bromo-1-(2-(1-(4-cyanophenylmethyl)imidazol-4-yl)-1-oxoethyl)-1,2-dihydro-4-(2-methoxyphenyl)-imidazo[1,2-c][1,4]benzodiazepine The product from Step 26.c. (100 mg, 0.23 mmol) was suspended in DMF (1.5 ml) and the product from Step 11.j. (125 mg, 0.45 mmol), TFFH (119 mg, 0.45 mmol), and NMM (110 ul, 1.0 mmol) were added. The reaction was stirred at room temperature for about 45 minutes and allowed to stand at room temperature overnight. The crude mixture was concentrated under reduced pressure and the residue was purified by preparative HPLC on a RAININ™ $C_{18}$ column using a gradient of 20-50% $CH_3CN/0.1\%$ Tfa over 45 minutes with UV detection at 254 nm. A second purification was performed using a isocratic system containing 44% $CH_3CN/0.2\%$ aqueous $NH_4OAc$. Product fractions were concentrated and lyophilized. The lyophilized product was re-lyophilized from 20% $CH_3CN/H_2O$, then converted to the Tfa salt by lyohpilization from 20% $CH_3CN/1\%$ Tfa, and then converted to the hydrochloride salt by passing a 30% methanolic solution through an ion exchange column (BioRad AG 1-X2, 200-400 mesh, 0.6 meq/ml, 100 ml, chloride form). The product fractions were combined, concentrated and lyophilized from 20% $CH_3CN/H_2O$ to yield pure product (45 mg, 30%) as the di-hydrochloride. Mass spec. 593.2, 595.2 $MH^+$, NMR (300 MHz, DMSO-$d_6$, 30° C.) 9.1-9.3 (1H, s), 7.9-8.1 (3H, m), 7.8-7.9 (2H, d), 7.7-7.8 (1H, d,d), 7.6-7.7 (1H, d), 7.5-7.6 (1H, s), 7.4-7.5 (2H, d), 7.3-7.45 (1H, t), 7.1-7.25 (1H, s), 7.0-7.1 (1H, t), 4.4-6.2 (2H, d,d), 5.4-5.7 (4H, m), 3.9-4.0 (3H, s), 3.5-3.9 (2H, d,d).

Example 27

1-(2-(1-(4-Cyanophenylmethyl)imidazol-4-yl)-1-oxoethyl)-1,2-dihydro-8-fluoro-4-(2-methoxyphenyl)-imidazo[1,2-c][1,4]benzodiazepine Steps 27.a. through 27.c. were performed in a manner analogous to Steps 22.a. through 22.c., substituting 2,6-difluorobenzyl bromide in place of 2-fluorobenzyl bromide in Step 27.a.

Step 27.d. 1-(2-(1-(4-Cyanophenylmethyl)imidazol-4-yl)-1-oxoethyl)-1,2-dihydro-8-fluoro-4-(2-methoxyphenyl)-imidazo[1,2-c][1,4]benzodiazepine The product from Step 27.c. (124 mg, 0.40 mmol) was suspended in DMF (2 ml) and the product from Step 11.j. (111 mg, 0.40 mmol), TFFH (106 mg, 0.40 mmol), and NMM (88 ul, 0.8 mmol) were added. The reaction was stirred at room temperature for about 1.5 hours A second portion of the product from Step 11.j. (111 mg, 0.40 mmol), TFFH (106 mg, 0.40 mmol), and NMM (88 ul, 0.8 mmol) were added and the reaction was stirred at room temperature for an additional 1.5 hours A third portion of the product from Step 11.j. (111 mg, 0.40 mmol), TFFH (106 mg, 0.40 mmol), and NMM (88 ul, 0.8 mmol) were added and the reaction was stirred at room temperature overnight. The crude mixture was concentrated under reduced pressure and the residue was purified by preparative HPLC on a RAININ™ $C_{18}$ column using a gradient of 20-50% $CH_3CN/0.1\%$ Tfa over 45 minutes with WV detection at 254 nm. Product fractions were combined and lyophilized. The Tfa salt was converted to the hydrochloride salt by passing a 40% methanolic solution through an ion exchange column (BioRad AG 1-X2, 200-400 mesh, 0.6 meq/ml, 100 ml, chloride form). The product fractions were combined, concentrated and lyophilized from $H_2O$ to yield pure product (126 mg, 59%) as the di-hydrochloride. Mass spec. 533.3 $MH^+$, NMR (300 MHz, DMSO-$d_6$, 30° C.) 9.2-9.3 (1H, s), 8.2-8.4 (1H, s), 7.9-8.1 (1H, d), 7.8-7.9 (2H, d), 7.55-7.7 (3H, m), 7.35-7.55 (4H, m), 7.15-7.25 (1H, d), 7.0-7.15 (1H, t), 4.5-6.3 (2H, d,d), 5.4-5.9 (2H, d,d), 5.5-5.7 (2H, d,d), 3.9-4.1 (3H, s), 3.6-4.0 (2H, d,d).

Example 28

1,2-Dihydro-1-(2-(imidazol-1-yl)-1-oxoethyl)-4-(2-methoxyphenyl)imidazo[1,2a][1,4]benzodiazepine A solution of the product from Step 22.c. (146 mg, 0.50 mmol) in DMF (2 ml) was treated with chloroacetyl chloride (44 ul, 0.55 mmol) in DMF (0.5 ml) and the mixture was stirred at room temperature for ½ hour. Imidazole (204 mg, 3.00 mmol) was added and the mixture was warmed at 50° C. for 3 hours and then allowed to stand at room temperature overnight. The crude mixture was concentrated under reduced pressure and the residue was purified by preparative HPLC on a RAININ™ $C_{18}$ column using a gradient of 10-50% $CH_3CN/0.1\%$ Tfa over 25 minutes with UV detection at 254 nm. Product fractions were combined and concentrated under reduced pressure. The Tfa salt was converted to the hydrochloride salt by passing a 30% methanolic solution through an ion exchange column (BioRad AG 1-X2, 200-400 mesh, 0.6 meq/ml, 100 ml, chloride form). The product fractions were combined, concentrated to a volume of about 10 ml and lyophilized from $H_2O$ to yield pure product (127 mg, 54%) as the di-hydrochloride.

Mass spec. 400.2 $MH^+$, NMR (300 MHz, DMSO-$d_6$, 30° C.) 9.1-9.2 (1H, s), 8.1-8.2 (1H, s), 7.9-8.05 (1H, d), 7.8-7.9 (1H, d), 7.5-7.8 (5H, m), 7.35-7.5 (1H, m), 7.15-7.25 (1H, d), 7.0-7.15 (1H, t), (6.2-6.35 (1H, d), 6.0-6.15 (1H, d), 5.5-5.7 (1H, d), 5.35-5.5 (1H, d), 4.95-5.15 (1H, d), 4.6-4.8 (1H, d), 3.9-4.0 (3H, s).

Example 29

1,2-Dihydro-4-(2-methoxyphenyl)-1-(2-(pyridin-3-yl)-1-oxoethyl)imidazo[1,2a][1,4]benzodiazepine A solution of the product from Step 22.c. (102 mg, 0.35 mmol) in DMF (1.5 ml) was treated with 3-pyridineacetic acid hydrochloride (69.4 mg, 0.40 mmol), NMM (110 ul, 1.00 mmol) and TFFH (106 mg, 0.40 mmol) and the mixture was stirred at room temperature for 1½ hours. An additional quantity of 3-pyridineacetic acid hydrochloride (26.0 mg, 0.15 mmol), NMM (33 ul, 0.30 mmol) and TFFH (40 mg, 0.15 mmol) were added to the reaction and stirring was continued at room temperature for 1½ hours. The crude mixture was concentrated under reduced pressure. Saturated $NaHCO_3$ solution (5 ml) was added and the product was extracted with $CH_2Cl$ (2×5 ml). The $CH_2Cl_2$ was distilled off under reduced pressure and the residue was dissolved in 10% aqueous $CH_3CN$ adjusted to pH=2 with Tfa. The crude product was purified by preparative HPLC on a RAININ™ $C_{18}$ column using a gradient of 10-50% $CH_3CN/0.1\%$ Tfa over 25 minutes with UV detection at 254 nm. Product fractions were combined and concentrated under reduced pressure. The Tfa salt was converted to the hydrochloride salt by passing a 30% methanolic solution through an ion exchange column (BioRad AG 1-X2, 200-400 mesh, 0.6 meq/ml, 100 ml, chloride form). The product fractions were combined, concentrated to a volume of about 10 ml and lyophilized from $H_2O$ to yield pure product (123 mg, 73%) as the di-hydrochloride. Mass spec. 411.1 $MH^+$.

Example 30

1,2-Dihydro-4-(2-methoxyphenyl)-1-(2-(pyridin-4-yl)-1-oxoethyl)imidazo[1,2a][1,4]benzodiazepine Example 30 was prepared in a manner analogous to Example 29 except 4-pyridineacetic acid hydrochloride was used in place of 3-pyridineacetic acid hydrochloride in Step 30.a. Mass spec. 411.1 MH+, NMR (300 MHz, DMSO-d$_6$, 30° C.) 8.8-8.9(2H, d), 8.1-8.2 (1H, s), 7.9-8.0 (3H, m), 7.75-7.9 (1H, d), 7.65-7.75 (1H, d), 7.6-7.7 (1H, t), 7.5-7.65 (1H, t), 7.35-7.5 (1H, m), 7.15-7.25 (1H, d), 7.0-7.15 (1H, t), 6.2-6.4 (1H, d), 5.7-5.85 (1H, d), 5.5-5.65 (1H, d), 4.5-4.7 (1H, d), 3.7-4.2 (2H, m), 3.9-4.05 (3H, s).

Example 31

1-(2-(1-benzylimidazol-5-yl)-1-oxoethyl)-1,2-dihydro-8-fluoro-4-(2-methoxyphenyl)imidazo[1,2a][1,4]benzodiazepine Steps 31.a. through 31.c. were performed in a manner analogous to Steps 22.a. through 22.c., substituting 2,6-difluorobenzyl bromide in place of 2-fluorobenzyl bromide in Step 31.a.

Step 31.d. 1-(2-(1-benzylimidazol-5-yl)-1-oxoethyl)-1,2-dihydro-8-fluoro-4-(2-methoxyphenyl)imidazo[1,2a][1,4]benzodiazepine The product from Step 31.c. was coupled to the product from Step 5.c. (1-phenylmethyl-5-imidazoleacetic acid) and purified in a manner analogous to Step 25.b. Mass spec 508.5 MH+, NMR (300 MHZ, DMSO-d$_6$, 30° C.) 9.1-9.3 (1H, s), 8.2-8.3 (1H, s), 7.9-8.0 (1H, d,d), 7.2-7.7 (10H, m), 7.15-7.25 (1H, d), 7.0-7.15 (1H, t), 6.1-6.3 (1H, d), 5.65-5.8 (1H, d), 5.3-5.6 (3H, m), 4.45-4.6 (1H, d), 3.9-4.0 (3H, s), 3.6-3.9 (2H, q).

Example 32

1-(2-(1-((4-cyano)phenylmethyl)imidazol-5-yl)-1-oxoethyl-9,10-difluoro-1,2-dihydro-4-(2-methoxyphenyl)imidazo[1,2c][1,4]-benzodiazepine Steps 32.a. through 32.c. were performed in a manner analogous to Steps 22.a. through 22.c., substituting 2,4,5-trifluorobenzyl bromide in place of 2-fluorobenzyl bromide in Step 32.a.

Step 32.d. 1-(2-(1-((4-cyano)phenylmethyl)imidazol-5-yl)-1-oxoethyl-9,10-difluoro-1,2-dihydro-4-(2-methoxyphenyl)imidazo[1,2c][1,4]-benzodiazepine The product from Step 32.c. was coupled to the product from Step 11.j. (1-(cyanophenylmethyl-5-imidazoleacetic acid hydrochloride) and purified in a manner analogous to Step 25.b. Mass spec 551.4 MH+, NMR (300 MHZ, DMSO-d$_6$, 30° C.) 9.1-9.3 (1H, s), 7.9-8.1 (3H, m), 7.75-7.9 (3H, m), 7.55-7.65 (1H, s), 7.45-7.55 (2H, d), 7.35-7.45 (1H, m), 7.15-7.25 (1H, d), 7.0-7.15 (1H, t).

Example 33

4-(2-bromophenyl)-1-(2-(1-[(4-cyano)phenylmethyl]imidazol-5-yl)-1-oxoethyl)-1,2-dihydro-8-fluoro-imidazo[1,2a][1,4]-benzodiazepine Step 33.a. 2,2'-dibromoacetophenone Bromine (40.3 g, 0.25 mol) was added dropwise to a solution of 2'-Bromoacetophenone (50.0 g, 0.25 mol) in acetic acid (500 ml) over 1.5 hours at 15-20° C. The solution was then allowed to warm to room temperature and concentrated under reduced pressure to yield a crude product that was used without further purification.

Step 33.b. was performed in a manner analogous to Step 1.c., substituting the product from Step 33.a in place of 2-bromo-2'-methoxyacetophenone and Cbz-Glycine in place of Cbz-(L)-Norleucine.

Steps 33.c. through 33.e. were performed in a manner analogous to steps 22.a. through 22.c., substituting 2,6-difluorobenzyl bromide in place of 2-fluorobenzyl bromide in Step 33.c., and substituting 1,8-Diazabicyclo[5.4.0]undec-7-ene in place of K$_2$CO$_3$ in Step 33.e.

Step 33.f. 4-(2-bromophenyl)-1-(2-(1-[(4-cyano)phenylmethyl]imidazol-5-yl)-1-oxoethyl)-1,2-dihydro-8-fluoro-imidazo[1,2a][1,4]-benzodiazepine The product from Step 33.e. was coupled to the product from Step 11.j. (1-(cyanophenylmethyl-5-imidazoleacetic acid hydrochloride) and purified in a manner analogous to Step 25.b. Mass spec 581.1, 583.1 MH+.

Example 34

1-(2-(1-((4-cyano)phenylmethyl)imidazo-5-yl)-1-oxoethyl)-1,2-dihydro-10-fluoro-4-(2-methoxyphenyl)imidazol[1,2a][1,4]-benzodiazepine Steps 34.a. through 34.c. were performed in a manner analogous to Steps 22.a. through 22.c., substituting 2,4-difluorobenzyl bromide in place of 2-fluorobenzyl bromide in Step 31.a.

Step 34.d. 1-(2-(1-((4-cyano)phenylmethyl)imidazo-5-yl)-1-oxoethyl)-1,2-dihydro-10-fluoro-4-(2-methoxyphenyl)imidazol[1,2a][1,4]-benzodiazepine The product from Step 34.c. was coupled to the product from Step 11.j. (1-(cyanophenylmethyl-5-imidazoleacetic acid hydrochloride) and purified in a manner analogous to Step 25.b. Mass spec 533.2 MH+.

Example 35

1-(2-(1-((4-cyano-3-methoxy)phenylmethyl)imidazo-5-yl)-1-oxoethyl)-1,2-dihydro-8-fluoro-4-(2-methoxyphenyl)imidazol[1,2a][1,4]-benzodiazepine Steps 35.a. through 35.f. were performed according to Scheme 35.

Scheme 35:

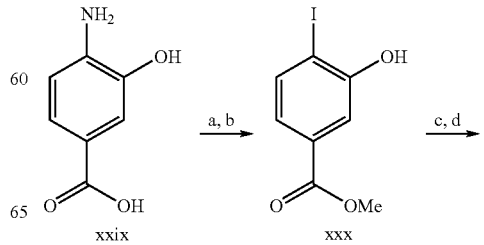

-continued

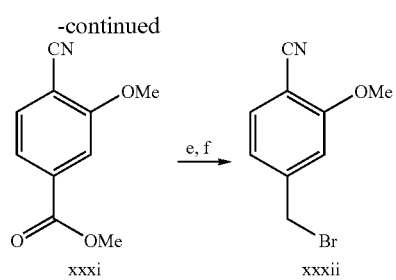

a. MeOH/HCl
b. NaNO₂/aq. HCl/KI
c. Zn(CN)₂/(Ph₃P)₄Pd/DMF
d. MeI/NaH/DMF
e. LiBH₄/THF
f. SOBr₂/CH₂Cl₂

Step 35.a. Methyl, 4-amino-3-hydroxybenzoate

A solution of 4-amino-3-hydroxybenzoic acid (24.5 g, 159 mmol) in methanol (650 ml) was cooled in an ice bath and treated with gaseous HCl for about 20 min. (about 60 g). Stirring was continued overnight and then the solution was concentrated under reduced pressure. The residue was triturated with EtOAc (200 ml) and dried to a brown solid (24.5 g, 92%) which was used without further purification. Mass spec. 168.2, NMR (300 MHZ, DMSO-$d_6$, 30° C.) 9.3-9.4 (1H, s), 7.2-7.3 (2H, m), 6.55-6.65 (1H, d), 5.3-5.4 (2H, s(broad)), 3.6-3.8 (3H, s).

Step 35.b. Methyl, 3-hydroxy-4-iodobenzoate

A solution of the product from Step 35.a. (24.5 g, 146 mmol) in THF (77 ml) was diluted with 3N HCl (232 ml) and cooled in an ice bath to 8° C. when a precipitate formed. NaNO₂ (11.1 g, 161 mmol) in H₂O (75 ml) was added over 6 minutes at ice bath temperature. Continue stirring 25 minutes and then add a solution of KI (97.1 g, 585 mmol) in H₂O (75 ml) in one portion, and stir 15 minutes. Add EtOAc (550 ml) and separate layers. Wash the EtOAc layer with H₂O (500 ml) and brine (400 ml), dry over Na₂SO₄, filter and concentrate to black solid. The crude product was purified by silica gel chromatography using CH₂Cl₂ as eluant to yield 19.7 g (48%) of an off-white solid. NMR (300MHZ, DMSO-$d_6$, 30° C.) 10.6-10.8 (1H, s), 7.8-7.9 (1H, d), 7.4-7.5 (1H, m), 7.1-7.2 (1H, m), 3.75-3.85 (3H, s).

Step 35.c. Methyl, 4-cyano-3-hydroxybenzoate

A solution of the product from Step 35.b. (25.3 g, 91.1 mmol), and ZnCN₂ (7.48 g, 63.7 mmol) in DMF (100 ml) was treated, under N₂, with (Ph₃P)₄Pd (2.0 g, 1.82 mmol) and warmED at about 80° C. for 4 hours. The solution was then cooled to room temperature and distributed between EtOAc (400 ml) and H₂O (400 ml). The EtOAc layer was washed with brine (4×200 ml), driedover NaSO₄, filtered and concentrated under reduced pressure. The crude product was purified by silica gel chromatography using CH₂Cl₂, and then 2.5% MeOH/CH₂Cl, as eluants. Fractions were concentrated to a light orange solid and dried to constant weight under vacuum to yield product (13.4 g, 83%) which was used in Step 35.d. without further purification. NMR (300 MHZ, DMSO-$d_6$, 30° C.) 7.7-7.8 (1H, m), 7.5-7.6 (1H, d), 7.4-7.5 (1H, m), 3.8-3.9 (3H, s).

Step 35.d. Methyl, 4-cyano-3-Methoxy-benzoate

60% NaH in mineral oil (6.02 g, 151 mmol) was washed with 3 portions of hexanes (20 ml) and suspended in DMF (100 ml) at room temperature. The product from Step 35.c. (13.3 g, 75.3 mmol) in DMF (100 ml) was added and the resulting mixture was treated with iodomethane (9.38 ml, 151 mmol). The reaction was allowed to stir overnight at room temperature. The reaction mixture was diluted with EtOAc (400 ml) and washed with 5% citric acid (2×150 ml) and brine (150 ml). The EtOAc layer was then dried over Na₂SO₄, filtered and concentrated to yield solid product (13.4 g, 93%) which was used in Step 35.e. without further purification. NMR (300 MHZ, CDCl₃, 30° C.) 7.62-7.72 (3H, m), 4.0-4.1 (3H, s), 3.9-4.0 (3H, s).

Step 35.e. 4-hydroxymethyl-2-methoxy-benzonitrile

The product from Step 35.d. (13.3 g, 70.0 mmol) in THF (200 ml) was treated with 2M LiBH₄ (75 ml, 150 mmol) under N₂ and the resulting solution was heated at reflux for 3 hours. The reaction was cooled to room temperature and treated carefully with excess 4N HCl to quench excess reagent. H₂O (50 ml) and EtOAc (100 ml) were added and the layers were separated. The aqueous layers were re-extracted with EtOAc (2×50 ml) and the EtOAc layers were combined and washed with brine (3×100 ml), dried (Na₂SO₄), filtered and concentrated under reduced pressure to yield a white solid (10.7 g, 94%). NMR (300 MHZ, CDCl₃, 30° C.) 7.5-7.8 (1H, d), 7.0-7.1 (1H, s), 6.94-7.0 (1H, m), 4.75-4.8 (2H, s), 3.9-4.0 (3H, s), 1.9-2.1 (1H, s(broad)).

Step 35.f. 4-bromomethyl-2-methoxy-benzonitrile

The product from Step 35.e. (1.0 g, 6.13 mmol) was suspended in CH₂Cl₂ (3.0 ml), treated with SOBr₂ (480 ul, 6.13 mmol), stirred for about ½ hour and then concentrated. The residue was re-dissolved in CH₂Cl₂ (100 ml), washed with saturated NaHCO₃ solution (50 ml), dried (Na₂SO₄), filtered and concentrated to a light yellow solid (1.22 g, 88%). NMR (300 MHZ, CDCl₃, 30° C.) 7.5-7.6 (1H, d(j=8 hz)), 7.02-7.08 (1H, d,d(j=8 Hz, j=1 Hz), 7.0-7.02 (1H, d(j=1 Hz), 4.45-4.5 (2H, s), 3.95-4.0 (3H, s).

Step 35.g. through 35.i. were performed in a manner analogous to steps 5.a. through 5.c., substituting the product from Step 35.f for Benzyl bromide in Step 5.a.

Step 35.j. 1-(2-(1-((4-cyano-3-methoxy)phenylmethyl)imidazo-5-yl)-1-oxoethyl)-1,2-dihydro-8-fluoro-4-(2-methoxyphenyl)imidazol[1,2a][1,4]-benzodiazepine The product from Step 31.c. was coupled to the product from Step 35.i. (1-((4-cyano-3-methoxy-phenyl)methyl)-5-imidazoleacetic acid hydrochloride) and purified in a manner analogous to Step 25.b. Mass spec 563.2 MH⁺.

Example 36

10-Bromo-1-(2-(1-((4-cyano-3-methoxy)phenylmethyl)imidazo-5-yl)-1-oxoethyl)-1,2-dihydro-4-(2-methoxyphenyl)imidazol[1,2a][1,4]-benzodiazepine Steps 36.a. through 36.c. were performed in a manner analogous to Steps 22.a. through 22.c., substituting 2,4-dibromobenzyl bromide in place of 2-fluorobenzyl bromide in Step 36.a.

Step 36.d. 10-Bromo-1-(2-(1-((4-cyano-3-methoxy) phenylmethyl)imidazo-5-yl)-1-oxoethyl)-1,2-dihydro-4-(2-methoxyphenyl)imidazol[1,2a][1,4]-benzodiazepine The product from Step 36.c. (10-Bromo-1,2-dihydro-4-(2-methoxyphenyl)-imidazo[1,2-c][1,4]benzodiazepine) was coupled to the product from Step 35.i. (1-((4-cyano-3-methoxy-phenyl)methyl)-5-imidazoleacetic acid hydrochloride) and purified in a manner analogous to Step 25.b. Mass spec 623.1, 625.1 MH⁺.

Example 37

1-(2-(1-((4-cyano-3-methoxy)phenylmethyl)imidazo-5-yl)-1-oxoethyl)-1,2-dihydro-8-fluoro-4-phenylimidazol[1,2a][1,4]-benzodiazepine The product from Step 31.c. (1,2-dihydro-8-fluoro-4-(2-methoxyphenyl)-imidazo[1,2-c][1,4]benzodiazepine) was coupled to the product from Step 35.i. (1-((4-cyano-3-methoxy-phenyl)methyl)-5-imidazoleacetic acid hydrochloride) and purified in a manner analogous to Step 25.b. Mass spec 533.3 MH⁺.

Example 38

4-(2-bromophenyl)-1-(2-(1-((4-cyano-3-methoxy)phenylmethyl)-imidazo-5-yl)-1-oxoethyl)-1,2-dihydro-8-fluoro-imidazol[1,2a][1,4]-benzodiazepine The product from Step 33.e. (4-(2-bromophenyl)-1,2-dihydro-8-fluoro-imidazo[1,2-c][1,4]benzodiazepine) was coupled to the product from Step 35.i. (1-((4-cyano-3-methoxy-phenyl)methyl)-5-imidazoleacetic acid hydrochloride) and purified in a manner analogous to Step 25.b. Mass spec 611.1, 613.1 MH⁺.

Example 39

1-(2-(1-((3-methoxy)phenylmethyl)imidazo-5-yl)-1-oxoethyl)-1,2-dihydro-8-fluoro-4-(2-methoxyphenyl)imidazol[1,2a][1,4]-benzodiazepine Steps 39.a. through 39.c. were performed in a manner analogous to steps 5.a. through 5.c., substituting 3-methoxy-benzyl bromide in place of benzyl bromide in Step 5.a.

Step 39.d. 1-(2-(1-((3-methoxy)phenylmethyl)imidazo-5-yl)-1-oxoethyl)-1,2-dihydro-8-fluoro-4-(2-methoxyphenyl)imidazol[1,2a][1,4]-benzodiazepine The product from Step 31.c. (1,2-dihydro-8-fluoro-4-(2-methoxyphenyl)-imidazo[1,2-c][1,4]benzodiazepine) was coupled to the product from Step 39.c. (1-((3-methoxyphenyl)methyl)-5-imidazoleacetic acid hydrochloride) and purified in a manner analogous to Step 25.b. Mass spec 538.4 MH⁺.

Example 40

1-(2-(5-((4-cyano)phenylmethyl)imidazol-1-yl)-1-oxoethyl-2,5-dihydro-8-fluoro-4-(2-methoxyphenyl)imidazo[1,2c][1,4]-benzodiazepine Steps 40.a. through 40.d. were performed according to scheme 40, as follows:

Scheme 40:

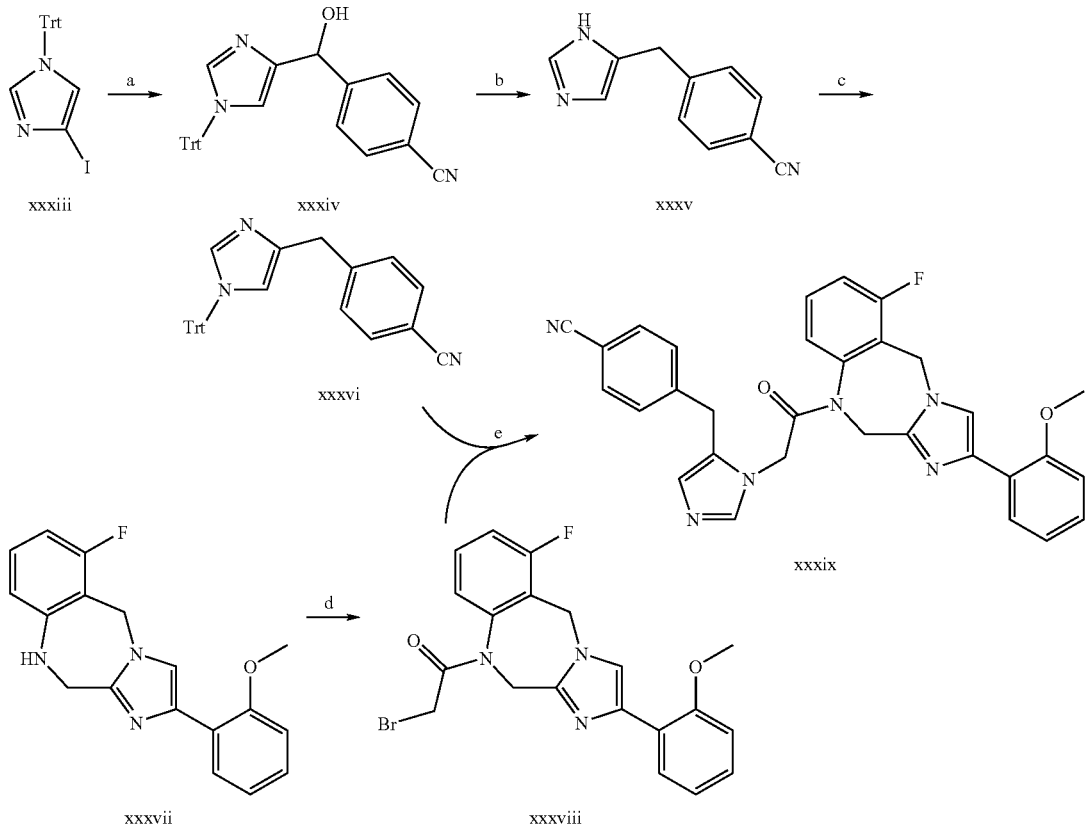

a. EtMgBr/4-cyano-benzaldehyde/Et₂O/CH₂Cl₂
b. Tfa/Et₃SiH/(reflux)
c. Trt—Cl/Et₃N/THF
d. BrCH₂COBr/DMF
e. intermediate xxxvi, then MeOH

Step 40.a. (R,S) 4-(Hydroxy-(1-trityl-1H-imidazol-4-yl)-methyl)-benzonitrile A solution of 1-trityl4-iodoimidazole (3.53 g, 8.10 mmol) in CH$_2$Cl$_2$ (35 ml) was cooled to about −3° C. under N$_2$ and 3M EtMgBr in Et$_2$O was added dropwise while maintaining reaction temperature at below about 0° C. The solution was stirred for about one hour at about 0° C. and then 4-cyanobenzaldehyde (1.18 g, 9.00 mmol) was added in one portion and the reaction was allowed to warm to room temperature for about 1 hour. The reaction mixture was then again cooled to about 0° C. and 5% HCl (30 ml) was added. The reaction mixture was stirred about 15 min. and then extracted with CH$_2$Cl$_2$ (2×25 ml). The combined CH$_2$Cl$_2$ layers were washed with saturated NaHCO$_3$, dried over Na$_2$SO$_4$, filtered, and then concentrated under reduced pressure. The residue was triturated with EtOAc (25 ml) and the product filtered off (2.92 g, 82%). Mass spec. 442.3 MH$^+$, NMR (300 MHZ, DMSO-d$_6$, 30° C.) 7.7-7.8 (2H, d), 7.5-7.6 (2H, d), 7.3-7.5 (9H, m), 7.25-7.3 (1H, s), 7.0-7.15 (6H, m), 6.75-6.8 (1H, s), 5.9-6.90 (1H, m), 5.6-5.7 (1H, m).

Step 40.b. 4-((1H-imidazol-4-yl)-methyl)-benzonitrile

A solution of the product from Step 40.a. (1.10 g, 2.49 mmol) was treated with Tfa (15 ml) and Et$_3$SiH (3.0 ml, 18.8 mmol). The mixture was heated at reflux for about 2 hours. The reaction mixture was then concentrated to remove by-products. Tfa (15 ml) and Et$_3$SiH (3.0 ml, 18.8 mmol) were added and the mixture was refluxed for an additional about 2 hours and then concentrated. Fresh reagents were added and by-products were removed by evaporation under reduced pressure as required until the starting material was consumed. Consumption of starting material was monitored by analytical HPLC analysis using a VYDAC C$_{18}$ column (The Nest Group, Southborough, Mass.) and a gradient of 0% to 70% CH$_3$CN/0.1% Tfa over 25 minutes. The crude product was purified by preparative HPLC on a RAININ™ C$_{18}$ column using a gradient of 0% to 50% CH$_3$CN/0.1% Tfa over 45 min. Product fractions were combined, concentrated to ½ volume and lyophilized to yield pure product. The product salt was made basic with saturated NaHCO$_3$ solution, extracted into CH$_2$Cl$_2$ (3×25 ml), dried over NaSO$_4$, filtered and concentrated under reduced pressure. Mass spec. 183.9 MH$^+$, NMR (300 MHZ, CDCl$_3$, 30° C.) 7.55-7.6 (2H, d (j=8 hz), 7.55-7.58 (1H, d (j=1 hz)), 7.3-7.4 (2H, d(j=8 hz)), 6.75-6.8 (1H, d (j=1 hz)), 3.9-4.1 (2H, s).

Step 40.c. 4-((1-trityl-1H-imidazol-4-yl)-methyl)-benzonitrile

The product from Step 40.b. (152 mg, 0.83 mmol), chlorotriphenylmethane (231 mg, 0.83 mmol) and Et$_3$N (139 ul, 1.0 mmol) were dissolved in THF (4 ml) and stirred under N$_2$ at room temperature for about 2 hours. A saturated solution of NaHCO$_3$ (5 ml) was added and the product was extracted with EtOAc (2×20 ml). The organic layer was dried over Na$_2$SO$_4$ and concentrated under reduced pressure. The crude was purified by crystallization from EtOAc and hexanes to yield pure product (285 mg, 81%). Mass spec. 426.4 MH$^+$ (minor line), NMR (300 MHZ, CDCl$_3$, 30° C.) 7.5-7.6 (2H, d(j=8 hz)), 7.4-7.45 (1H, d(j=1 hz)), 7.3-7.4 (11H, m), 7.1-7.2 (6H, m), 6.58-6.62 (1H, d(j=1 Hz)), 3.9-4.0 (2H, s).

Step 40.d. 1-Bromoacetyl-1,2-dihydro-8-fluoro-4-(2-methoxyphenyl)imidazo[1,2a][1,4]benzodiazepine The product from Step 40.c. (108 mg, 0.35 mmol) was dissolved in DMF (1.5 ml) and Bromoacetyl bromide (65 ul, 0.75 mmol) was added at room temperature with stirring. The mixture was allowed to stand overnight and was then concentrated under reduced pressure to give crude product that was used in Step 40.e. without further purification. Mass spec. 430.2 432.2 MH$^+$.

Step 40.e. (2-(5-((4-cyano)phenylmethyl)imidazol-1-yl)-1-oxoethyl-2,5-dihydro-8-fluoro-4-(2-methoxyphenyl)imidazo[1,2c][1,4]-benzodiazepine The product from Step 40.d. (0.32 mmol) was distributed between saturated NaHCO$_3$ (2 ml) and EtOAc (5 ml). The aqueous layer was extracted again with EtOAc (5 ml) and the EtOAc layers were combined, dried (NaSO$_4$), filtered and concentrated to about 2 ml. The product from Step 40.c. (134 mg, 0.32 mmol) was added and the mixture was stirred at room temperature for about 2 days and then concentrated under reduced pressure. The residue was taken up in methanol (4 ml) and heated at reflux for about 1 hour. The reaction was cooled and concentrated under reduced pressure and the crude product was purified by preparative HPLC on a RAININ™ C$_{18}$ column using a gradient of 0% to 50% CH$_3$CN/0.1% Tfa over 45 min. Product fractions were combined and concentrated under reduced pressure. The Tfa salt was converted to the hydrochloride salt by passing a 30% methanolic solution through an ion exchange column (BioRad AG 1-X2, 200-400 mesh, 0.6 meq/ml, 100 ml, chloride form). The product fractions were combined, concentrated to a volume of about 10 ml and lyophilized from H$_2$O to yield pure product (35 mg, 18%) as the di-hydrochloride. Mass spec. 533.2 MH$^+$.

It is to be understood that while the invention has been described in conjunction with the detailed description thereof, that the foregoing description is intended to illustrate and not limit the scope of the invention defined by the appended claims. Other aspects, advantages, and modifications are within the claims.

What is claimed is:
1. A compound of formula I,

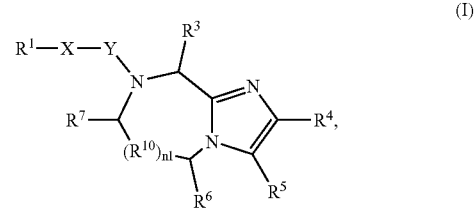

wherein n1 is 0;

X is, independently for each occurrence, (CHR$^{11}$)$_{n3}$(CH$_2$)$_{n4}$Z(CH$_2$)$_{n5}$, Z is O, N(R$^{12}$), S, or a bond;

n3 is, independently for each occurrence, 0 or 1;

n4 and n5 each is, independently for each occurrence, 0, 1, 2, or 3;

Y is, independently for each occurrence, CO, CH$_2$, CS, or a bond;

$R^1$ is

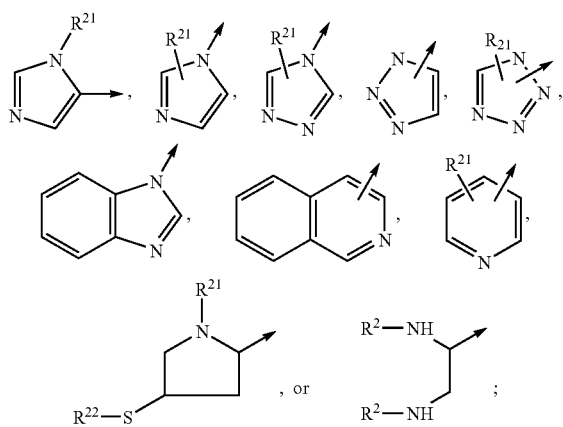

, or

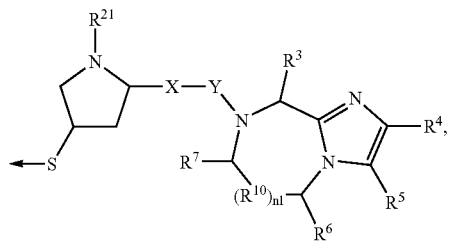

;

$R^2$, $R^{11}$ and $R^{12}$ each is, independently for each occurrence, H or an optionally substituted moiety selected from the group consisting of $(C_{1-6})$alkyl and aryl, wherein said optionally substituted moiety is optionally substituted with one or more of $R^8$ or $R^{30}$;

$R^3$ is, independently for each occurrence, H or an optionally substituted moiety selected from the group consisting of $(C_{1-6})$alkyl, $(C_{2-6})$alkenyl, $(C_{2-6})$alkynyl, $(C_{3-6})$cycloalkyl, $(C_{3-6})$cycloalkyl$(C_{1-6})$alkyl, $(C_{5-7})$cycloalkenyl, $(C_{5-7})$cycloalkenyl$(C_{1-6})$alkyl, aryl, aryl$(C_{1-6})$alkyl, heterocyclyl, and heterocyclyl$(C_{1-6})$alkyl, wherein said optionally substituted moiety is optionally substituted with one or more $R^{30}$;

$R^4$ and $R^5$ each is, independently for each occurrence, H or an optionally substituted moiety selected from the group consisting of $(C_{1-6})$alkyl, $(C_{3-6})$cycloalkyl, aryl, and heterocyclyl, wherein said optionally substituted moiety is optionally substituted with one or more $R^{30}$, wherein each said substituent is independently selected;

$R^6$ is, independently for each occurrence, H or an optionally substituted moiety selected from the group consisting of $(C_{1-6})$alkyl, $(C_{2-6})$alkenyl, $(C_{3-6})$cycloalkyl, $(C_{3-6})$cycloalkyl $(C_{1-6})$alkyl, $(C_{5-7})$cycloalkenyl, $(C_{5-7})$cycloalkenyl $(C_{1-6})$alkyl, aryl, aryl$(C_{1-6})$alkyl, heterocyclyl, and heterocyclyl $(C_{1-6})$alkyl, wherein said optionally substituted moiety is optionally substituted with one or more substituents each independently selected from the group consisting of OH, $(C_{1-6})$alkyl, $(C_{1-6})$alkoxy, $-N(R^8R^9)$, $-COOH$, $-CON(R^8R^9)$, and halo, where $R^8$ and $R^9$ each is, independently for each occurrence, H, $(C_{1-6})$alkyl, $(C_{2-6})$alkenyl, $(C_{2-6})$alkynyl, aryl, or aryl$(C_{1-6})$alkyl;

$R^7$ is, independently for each occurrence, H, $=O$, $=S$, or an optionally substituted moiety selected from the group consisting of $(C_{1-6})$alkyl, $(C_{2-6})$alkenyl, $(C_{3-6})$cycloalkyl, $(C_{3-6})$cycloalkyl$(C_{1-6})$alkyl, $(C_{5-7})$cycloalkenyl, $(C_{5-7})$cycloalkenyl$(C_{1-6})$alkyl, aryl, aryl$(C_{1-6})$alkyl, heterocyclyl, and heterocyclyl$(C_{1-6})$alkyl, wherein said optionally substituted moiety is optionally substituted with one or more substituents each independently selected from the group consisting of OH, $(C_{1-6})$alkyl, $(C_{1-6})$alkoxy, $-N(R^8R^9)$, $-COOH$, $-CON(R^8R^9)$, and halo;

$R^{10}$ is C;

$R^{21}$ is, independently for each occurrence, H or an optionally substituted moiety selected from the group consisting of $(C_{1-6})$alkyl and aryl$(C_{1-6})$alkyl, wherein said optionally substituted moiety is optionally substituted with one or more substituents each independently selected from the group consisting of $R^8$ and $R^{30}$;

$R^{22}$ is H, $(C_{1-6})$alkylthio, $(C_{3-6})$cycloalkylthio, $R^8-CO-$, or a substituent according to the formula

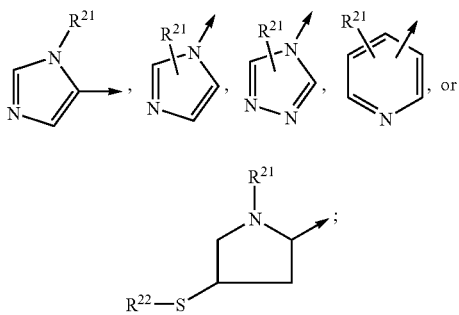

$R^{24}$ and $R^{25}$ each is, independently for each occurrence, H, $(C_{1-6})$alkyl, or aryl$(C_{1-6})$alkyl;

$R^{30}$ is, independently for each occurrence, $(C_{1-6})$alkyl, $-O-R^8$, $-S(O)_{n6}R^8$, $-S(O)_{n7}N(R^8R^9)$, $-N(R^8R^9)$, $-CN$, $-NO_2$, $-CO_2R^8$, $-CON(R^8R^9)$, $-NH-CO-R^8$, or halogen;

n6 and n7 each is, independently for each occurrence, 0, 1, or 2;

wherein said heterocyclyl is azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N—oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, or thienyl; and wherein said aryl is phenyl or naphthyl; or a pharmaceutically acceptable salt thereof.

2. A compound according to claim 1, wherein:

$R^1$ is and

X is $CH(R^{11})_{n3}(CH_2)_{n4}$ or Z, wherein Z is O, S or $N(R^{12})$;

or a pharmaceutically acceptable salt thereof.

3. A compound according to claim 2, wherein:

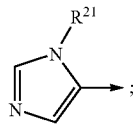

R¹ is
X is $CH(R^{11})_{n3}(CH_2)_{n4}$; and
n1 is 0;
or a pharmaceutically acceptable salt thereof.

4. A compound according to claim 2, wherein:

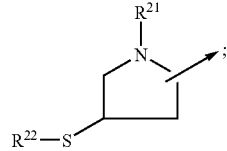

R¹ is
n3, n4, and n5 each is 0;
Z is a bond;
Y is, independently for each occurrence, CO or CS; and
n1 is 0;
or a pharmaceutically acceptable salt thereof.

5. A compound according to claim 3, wherein said compound is
- 8-butyl-7-(3-(imidazol-5-yl)-1-oxopropyl)-2-(2-methoxyphenyl)-5,6,7,8-tetrahydroimidazo[1,2a]pyrazine;
- 8-butyl-2-(2-hydroxyphenyl)-7-(imidazol-4-yl-propyl)-5,6,7,8-tetrahydroimidazo[1,2a]pyrazine;
- 8-butyl-7-(4imidazolylpropyl)-2-(2-methoxyphenyl)-5,6,7,8-tetrahydroimidazo [1, 2a]pyrazine;
- 7-(2-(imidazol-4-yl)-1-oxo-ethyl)-2-(2-methoxyphenyl)-8-(1-methylpropyl)-5,6,7,8-tetrahydroimidazo [1,2a]pyrazine;
- 2-(2-methoxyphenyl)-8-(1-methylpropyl)-7-(1-oxo-2-(1-(phenylmethyl)-imidazol-5-yl)ethyl)-5,6,7,8-tetrahydroimidazo [1,2a]pyrazine;
- 2-(2-methoxyphenyl)-8-(1-methylpropyl)-7-((2-(1-phenylmethyl)-imidazol-5-yl) ethyl)-5, 6,7, 8-tetrahydroimidazo [1,2a]pyrazine;
- 7-(2-(1-(4-cyanophenylmethyl)-imidazol-5-yl)-1-oxoethyl)-2-(2-methoxyphenyl)-8-(1-methylpropyl)-5,6,7,8-tetrahydroimidazo [1,2a]pyrazine;
- 7-((1H-imidazol-4-yl)methyl)-2-(2-methoxyphenyl)-8-(1-methylpropyl)-5,6,7,8-tetrahydroimidazo [1,2a] pyrazine;
- 7-((4-imidazolyl)carbonyl)-2-(2-methoxyphenyl)-8-(1-methylpropyl)-5,6,7,8-tetrahydroimidazo [1,2a]pyrazine;
- 7-(1-(4-cyanophenylmethyl)-imidazol-5-yl)methyl-2-(2-methoxyphenyl)-8-(1-methylpropyl)-5, 6,7,8-tetrahydroimidazo [1,2a]pyrazine;
- 7-((2-(4-cyanophenylmethyl)-imidazol-5-yl)-1-oxoethyl)-2-(2-methoxyphenyl)-5,6,7,8-tetrahydroimidaz [1,2-a]pyrazine;
- 5-butyl-7-(2-(4-cyanophenylmethylimidazol-5-yl)-1-oxo-ethyl)-2-phenyl-5,6,7,8-tetrahydroimidazo[1,2a] pyrazine;
- 6-butyl-7-(2-(4-cyanophenylmethylimidazol-5-yl)-1-oxo-ethyl)-2-(2-methoxyphenyl)-5,6,7,8-tetrahydroimidazo [1,2-a]pyrazine;
- 6-butyl-7-(2-(4-cyanophenylmethylimidazol-5-yl)-1-oxo-ethyl)-2-phenyl-5,6,7,8-tetrahydroimidazo[1,2-a] pyrazine;
- 5-butyl-7-(2-(1-(4-cyanopheriylmethyl)-imidazole-5-yl)-1-oxo-ethyl)-2-(2-methoxyphenyl)-5,6,7,8-tetrahydroimidazo [1,2a]pyrazine;
- 7-(2-(1-(4-cyanophenylmethyl)-imidazole-5-yl)-1-oxo-ethyl)-8-(cyclohexylmethyl)-2-(2-methoxyphenyl)-5,6,7,8-tetrahydroimidazo[1,2a]pyrazine;
- 5-butyl-7-(2-(1H-imidazole-5-yl)-1-oxo-ethyl)-2-(2-methoxyphenyl)-5,6,7,8-tetrahydroimidazo [1,2a]pyrazine;
- 7-((2-(4-cyanophenylmethyl)-imidazol-5-yl)-1-oxo-ethyl)-2-(2-(phenylmethoxy)-phenyl)-5,6,7,8-tetrahydroimidazo[1,2-a]pyrazine; or
- 2-(2-butoxyphenyl)-7-((2-(4-cyanophenylmethyl)-imidazol-5-yl)-1-oxo-ethyl)-5,6,7,8-tetrahydroimidazo[1,2-a]pyrazine;

or a pharmaceutically acceptable salt thereof.

6. A compound according to claim 2, wherein said compound is

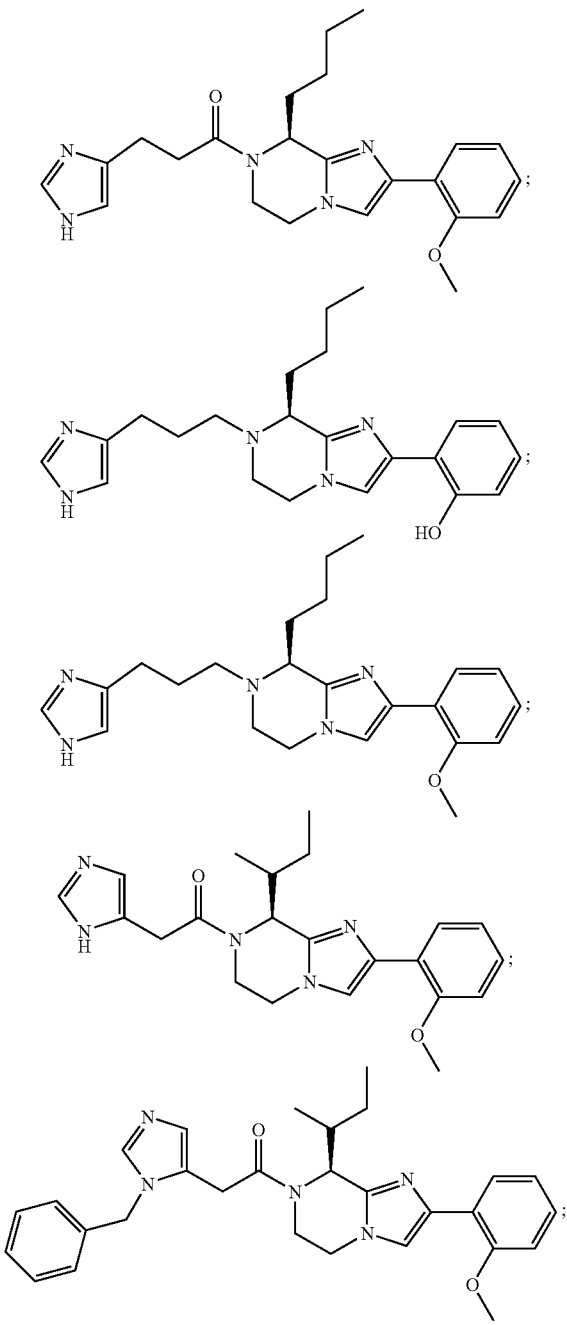

-continued
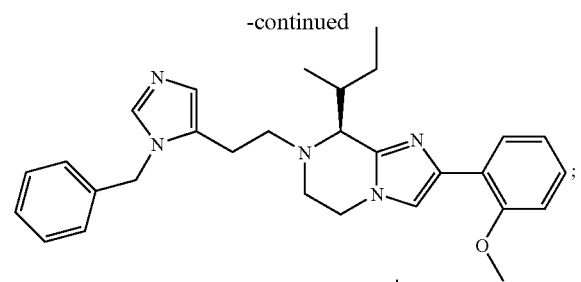
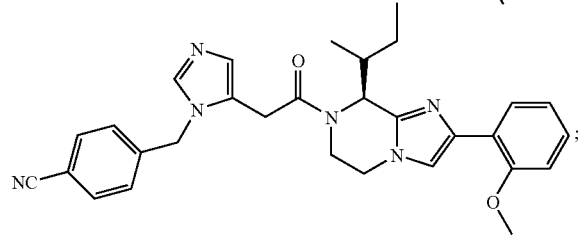
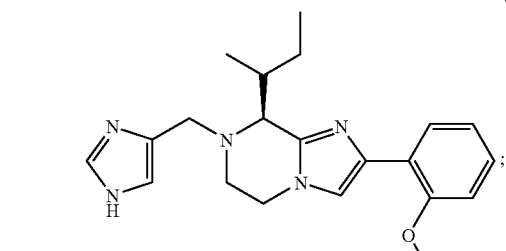
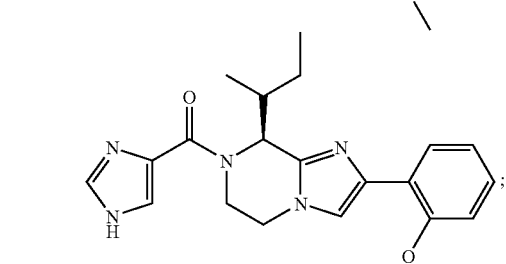
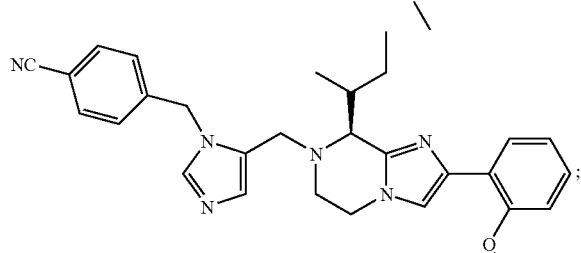
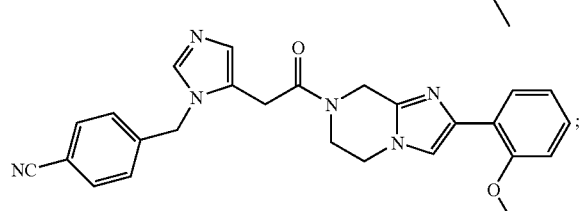
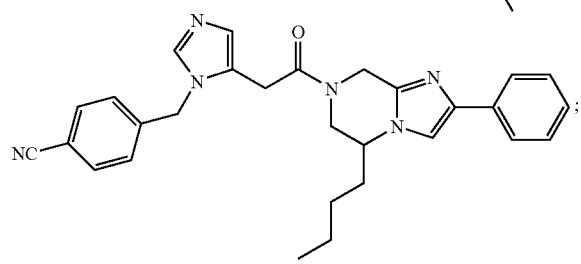
-continued
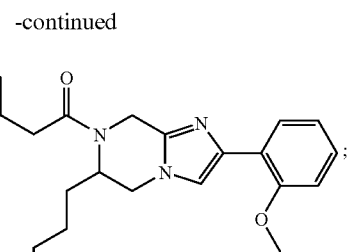
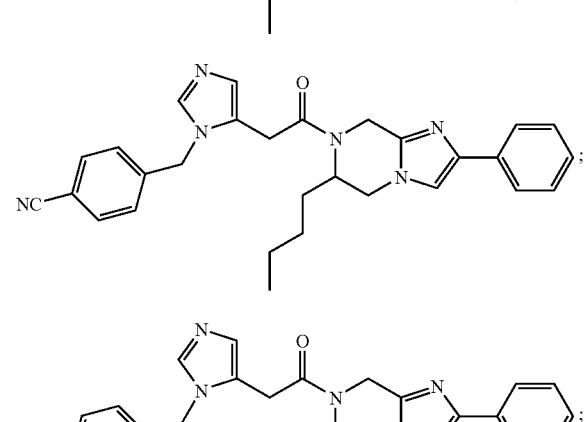
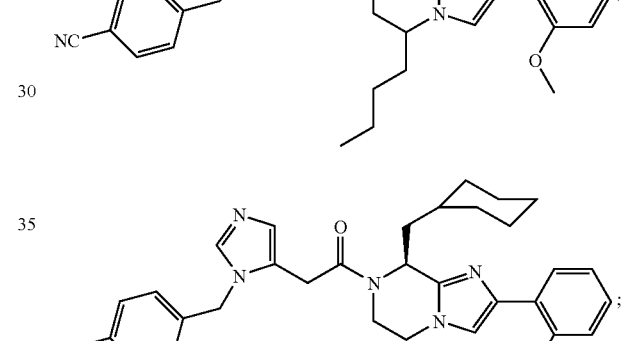
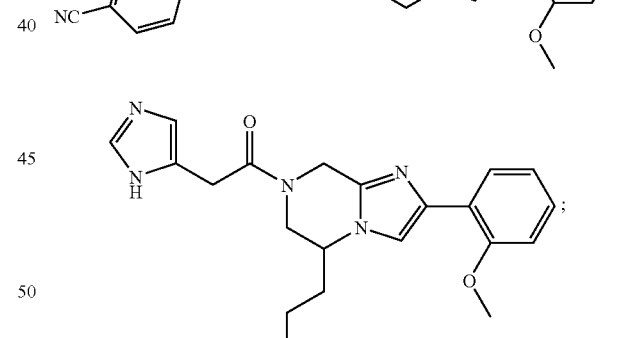
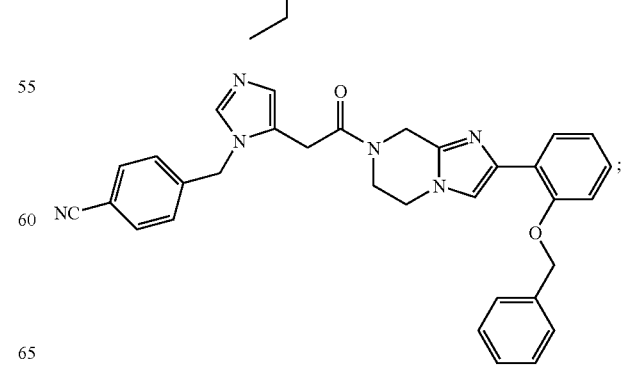

-continued
or

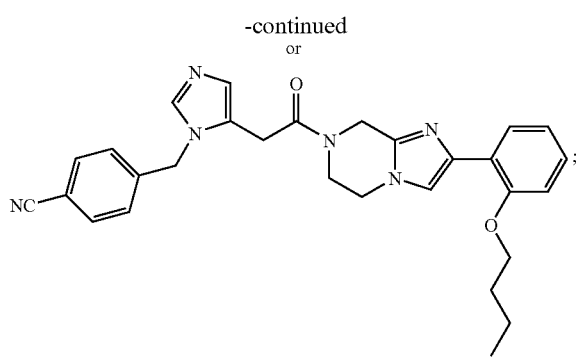

or a pharmaceutically acceptable salt thereof.

7. A pharmaceutical composition comprising an effective amount of a compound according to claim 1 or a pharmaceutically acceptable salt thereof and a pharmaceutically acceptable carrier.

8. A method of treating a disease in a subject in need thereof, said method comprising administering to said subject a therapeutically effective amount of a compound of claim 1, or a pharmaceutically acceptable salt thereof, wherein said disease is selected from the group consisting of fibrosis, benign prostatic hyperplasia, atherosclerosis, restenosis, breast cancer, colon cancer, pancreas cancer, prostate cancer, lung cancer, ovarian cancer, epidermal cancer, hematopoietic cancer, and hepatitis delta virus infection.

* * * * *